US009775895B2

(12) United States Patent
Lusso et al.

(10) Patent No.: US 9,775,895 B2
(45) Date of Patent: Oct. 3, 2017

(54) HIV THERAPEUTICS AND METHODS OF MAKING AND USING SAME

(71) Applicant: The United States of America, as represented by the Secretary, Department of Health and Human Services, Washington, DC (US)

(72) Inventors: Paolo Lusso, Rockville, MD (US); Raffaello Cimbro, North Bethesda, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/651,635

(22) PCT Filed: Dec. 12, 2013

(86) PCT No.: PCT/US2013/074801
§ 371 (c)(1),
(2) Date: Jun. 11, 2015

(87) PCT Pub. No.: WO2014/093702
PCT Pub. Date: Jun. 19, 2014

(65) Prior Publication Data

US 2015/0313990 A1 Nov. 5, 2015

Related U.S. Application Data

(60) Provisional application No. 61/736,350, filed on Dec. 12, 2012.

(51) Int. Cl.
| | |
|---|---|
| *C12Q 1/68* | (2006.01) |
| *C07H 21/04* | (2006.01) |
| *C07H 21/02* | (2006.01) |
| *C07K 14/47* | (2006.01) |
| *C12N 7/00* | (2006.01) |
| *A61K 39/21* | (2006.01) |
| *C07K 14/005* | (2006.01) |
| *A61K 45/06* | (2006.01) |
| *A61K 39/12* | (2006.01) |
| *A61K 39/00* | (2006.01) |

(52) U.S. Cl.
CPC .............. *A61K 39/21* (2013.01); *A61K 39/12* (2013.01); *A61K 45/06* (2013.01); *C07K 14/005* (2013.01); *C12N 7/00* (2013.01); *A61K 2039/5258* (2013.01); *A61K 2039/575* (2013.01); *A61K 2039/64* (2013.01); *C12N 2740/16023* (2013.01); *C12N 2740/16034* (2013.01); *C12N 2740/16051* (2013.01); *C12N 2740/16134* (2013.01); *C12N 2740/16171* (2013.01)

(58) Field of Classification Search
CPC .. C07K 14/47; C07K 14/005; C07K 2319/30; A61K 38/00; A61K 39/12
See application file for complete search history.

(56) References Cited

U.S. PATENT DOCUMENTS

| | | | |
|---|---|---|---|
| 5,541,095 | A | 7/1996 | Hirschberg et al. |
| 6,815,201 | B2 | 11/2004 | Pinter |
| 2003/0170849 | A1 | 9/2003 | Moore |
| 2006/0009631 | A1 | 1/2006 | Moore |
| 2006/0115859 | A1 | 6/2006 | Moore |
| 2009/0042738 | A1 | 2/2009 | Moore |

FOREIGN PATENT DOCUMENTS

| | | | |
|---|---|---|---|
| WO | WO01/64710 | | 9/2001 |
| WO | WO2004/072096 | | 8/2004 |
| WO | WO2013039792 | * | 3/2013 |

OTHER PUBLICATIONS

Acharya, et al. "Structure-based identification and neutralization mechanism of tyrosine sulfate mimetics that inhibit HIV-1 entry." *ACS Chemical Biology* 6, No. 10 (2011): 1069-1077.
Brower, et al. "Binding Thermodynamics of the N-Terminal Peptide of the CCR5 Coreceptor to HIV-1 Envelope Glycoprotein gp120." *Biochemistry* 48, No. 4 (2009): 779-785.

Cimbro, et al. "Tyrosine sulfation in the second variable loop (V2) of HIV-1 gp120 stabilizes V2-V3 interaction and modulates neutralization sensitivity." *Proceedings of the National Academy of Sciences* 111, No. 8 (2014): 3152-3157.

Cormier, et al. "Specific interaction of CCR5 amino-terminal domain peptides containing sulfotyrosines with HIV-1 envelope glycoprotein gp120." *Proceedings of the National Academy of Sciences* 97, No. 11 (2000): 5762-5767.

Dettin, et al. "CCR5 N-terminus peptides enhance X4 HIV-1 infection by CXCR4 up-regulation," *Biochemical and Biophysical Research Communications* 307, No. 3 (2003): 640-646.

Dorfman, et al. "A tyrosine-sulfated peptide derived from the heavy-chain CDR3 region of HIV-1-neutralizing antibody binds gp120 and inhibits HIV-1 infection." *Journal of Biological Chemistry* 281, No. 39 (2006): 28529-28535.

Farzan, et al. "A tyrosine-sulfated peptide based on the N terminus of CCR5 interacts with a CD4-enhanced epitope of the HIV-1 gp120 envelope glycoprotein and inhibits HIV-1 entry." *Journal of Biological Chemistry* 275, No. 43 (2000): 33516-33521.

(Continued)

*Primary Examiner* — Janet L Andres
*Assistant Examiner* — Barry A Chestnut
(74) *Attorney, Agent, or Firm* — Klarquist Sparkman, LLP

(57) ABSTRACT

HIV neutralizing peptides, sulfated HIV-1 envelope proteins and immunogenic fragments thereof are disclosed, as well as nucleic acids encoding these molecules and methods of producing these peptides, envelope proteins and fragments. Methods are also provided for the treatment or prevention of a human immunodeficiency type 1 (HIV-1 ) infection. The methods can include administering to a subject an HIV neutralizing peptide, sulfated HIV-1 envelope protein or immunogenic fragment thereof as disclosed herein. In several embodiments, administering the HIV neutralizing peptide, sulfated HIV-1 envelope protein or immunogenic fragment generates an immune response in a subject.

13 Claims, 25 Drawing Sheets

(56) References Cited

OTHER PUBLICATIONS

Fung, et al. "Identification and characterization of a neutralization site within the second variable region of human immunodeficiency virus type 1 gp120." *Journal of Virology* 66, No. 2 (1992): 848-856.
Lam, et al. "Tyrosine-sulfate isosteres of CCR5 N-terminus as tools for studying HIV-1 entry." *Bioorganic & Medicinal Chemistry* 16, No. 23 (2008): 10113-10120.
Lieberman-Aiden, et al. "Comprehensive mapping of long-range interactions reveals folding principles of the human genome." *Science* 326, No. 5950 (2009): 289-293.
Liu, et al. "Mutagenesis and evolution of sulfated antibodies using an expanded genetic code." *Biochemistry* 48, No. 37 (2009): 8891-8898.
Lusso, et al. "Cryptic nature of a conserved, CD4-inducible V3 loop neutralization epitope in the native envelope glycoprotein oligomer of CCR5-restricted, but not CXCR4-using, primary human immunodeficiency virus type 1 strains." *Journal of Virology* 79, No. 11 (2005): 6957-6968.
Ly, et al. "V2 loop glycosylation of the human immunodeficiency virus type 1 SF162 envelope facilitates interaction of this protein with CD4 and CCR5 receptors and protects the virus from neutralization by anti-V3 loop and anti-CD4 binding site antibodies." *Journal of Virology* 74, No. 15 (2000): 6769-6776.
Platt, et al. "Variants of human immunodeficiency virus type 1 that efficiently use CCR5 lacking the tyrosine-sulfated amino terminus have adaptive mutations in gp120, including loss of a functional N-glycan," *Journal of Virology* 79, No. 7 (2005): 4357-4368.
Walker, et al. "Broad and potent neutralizing antibodies from an African donor reveal a new HIV-1 vaccine target." *Science* 326, No. 5950 (2009): 285-289.
Xiang, et al. "Characterization of a dual-tropic human immunodeficiency virus (HIV-1) strain derived from the prototypical X4 isolate HXBc2." *Virology* 438, No. 1 (2013): 5-13.
Arthos, et al. "HIV-1 envelope protein binds to and signals through integrin α4β7, the gut mucosal homing receptor for peripheral T cells." *Nature Immunology* 9, No. 3 (2008): 301-309.
Chen, et al. "Structural basis of immune evasion at the site of CD4 attachment on HIV-1 gp120." *Science* 326, No. 5956 (2009): 1123-1127.
Choe, et al. "Tyrosine sulfation of HIV-1 coreceptors and other chemokine receptors." *Methods in Enzymology* 461 (2009): 147-170.
Choe, et al. "Tyrosine sulfation of human antibodies contributes to recognition of the CCR5 binding region of HIV-1 gp120." *Cell* 114, No. 2. (2003): 161-170.
Farzan, et al. "Tyrosine sulfation of the amino terminus of CCR5 facilitates HIV-1 entry." *Cell* 96, No. 5 (1999): 667-676.
Hu, et al. "Structural comparison of HIV-1 envelope spikes with and without the V1/V2 loop." *Journal of Virology* 85, No. 6 (2011): 2741-2750.
Huang, et al. "Structure of a V3-containing HIV-1 gp120 core." *Science* 310, No. 5750 (2005): 1025-1028.
Huang, et al. "Structures of the CCR5 N terminus and of a tyrosine-sulfated antibody with HIV-1 gp120 and CD4." *Science* 317, No. 5846 (2007): 1930-1934.
Julien, et al. "Crystal Structure of a Soluble Cleaved HIV-1 Envelope Trimer." (2013) *Science*, DOI, 1245625.
Karasavvas, et al. "The Thai Phase III HIV Type 1 Vaccine trial (RV144) regimen induces antibodies that target conserved regions within the V2 loop of gp120." *AIDS Research and Human Retroviruses* 28, No. 11 (2012): 1444-4457.
Kwong, et al. "Structure of an HIV gp120 envelope glycoprotein in complex with the CD4 receptor and a neutralizing human antibody." *Nature* 393, No. 6686 (1998): 648-659.
Kwong, et al. "Structures of HIV-1 gp120 envelope glycoproteins from laboratory-adapted and primary isolates." *Structure* 8, No. 12 (2000): 1329-1339.
Liu, et al. "Synthesis of proteins with defined posttranslational modifications using the genetic noncanonical amino acid incorporation approach," *Molecular BioSystems* 7, No. 1 (2011): 38-47.
Montefiori, et al. "Magnitude and breadth of the neutralizing antibody response in the RV144 and Vax003 HIV-1 vaccine efficacy trials." *Journal of Infectious Diseases* 206, No. 3 (2012): 431-441.
Moore, et al. "Potent and broad neutralization of HIV-1 subtype C by plasma antibodies targeting a quaternary epitope including residues in the V2 loop." *Journal of Virology* 85, No. 7 (2011): 3128-3141.
NCBI Ref. Seq. NM_001008566.1, available at: http://www.ncbi.nlm.nih.gov/nuccore/NM_001008566.1, accessed Nov. 23, 2015.
NCBI Ref. Seq. NM_001130476.2, available at: http://www.ncbi.nlm.nih.gov/nuccore/NM_001130476.2, accessed Nov. 23, 2015.
NCBI Ref. Seq. NM_003595.3, available at: http://www.ncbi.nlm.nih.gov/nuccore/NM_003595, accessed Nov. 23, 2015.
NCBI Ref. Seq. NM_003596.3, available at: http://www.ncbi.nlm.nih.gov/nuccore/NM_003596.3, accessed Nov. 23, 2015.
NCBI Ref. Seq. NM_009419.3, available at: http://www.ncbi.nlm.nih.gov/nuccore/NM_009419, accessed Nov. 23, 2015.
NCBI Ref. Seq. NP_001008566.1, available at: http://www.ncbi.nlm.nih.gov/protein/NP_001008566, accessed Nov. 23, 2015.
NCBI Ref. Seq. NP_001123948.1, available at: http://www.ncbi.nlm.nih.gov/protein/NP_001123948.1, accessed Nov. 23, 2015.
NCBI Ref. Seq. NP_003586.3, available at: http://www.ncbi.nlm.nih.gov/protein/NP_003586.3, accessed Nov. 23, 2015.
NCBI Ref. Seq. NP_003587.1, available at: http://www.ncbi.nlm.nih.gov/protein/4507665, accessed Nov. 23, 2015.
NCBI Ref. Seq. NP_033445.2, available at: http://www.ncbi.nlm.nih.gov/protein/NP_033445.2, accessed Nov. 23, 2015.
Pancera, et al. "Structure of HIV-1 gp120 with gp41-interactive region reveals layered envelope architecture and basis of conformational mobility." *Proceedings of the National Academy of Sciences* 107, No. 3, (2010): 1166-1171.
Sakihama, et al. "Oligomerization of CD4 is required for stable binding to class II major histocompatibility complex proteins but not for interaction with human immunodeficiency virus gp120." *Proceedings of the National Academy of Sciences* 92, No. 14 (1995): 6444-6448.
Walker, et al. "Broad neutralization coverage of HIV by multiple highly potent antibodies." *Nature* 477, No. 7365 (2011): 466-470.
Zolla-Pazner, et al. "Structure—function relationships of HIV-1 envelope sequence-variable regions refocus vaccine design." *Nature Reviews Immunology* 10, No. 7 (2010): 527-535.

* cited by examiner

FIG. 1A

```
              157                                           196
Subtype A  CSFNMTTELRDKKQKVYSLFYRLDVVQIN-x(9±3)-YRLINC
Subtype B  CSFNITTSIRDKVQKEYALFYKLDVVPID-x(7±4)-YRLISC
Subtype C  CSFNATTEIRDKKKKEYALFYRLDIVPLN-x(9±4)-YRLINC
Subtype D  CSFNITTEVRDKKKQVHALFYKLDVVQID-x(8±3)-YRLINC
Subtype E  CSFNMTTELRDKKQKVHALFYKLDIVQIE-x(7±4)-YRLINC
Subtype F  CSFNMTTEVRDKKKKVHALFYRLDIVPIN-x(8±3)-YRLINC
           ****  **.;***   ;; ;;***;**;*   ;;         ****,*
```

FIG. 1B

Intra-subtype conservation: ▢ >80%   ▢ 60-80%   ▢ <60%

```
           157                                           196
Agadir    CSFKITTN IRGKVQKEYALFY ELDIVPIDNNSNNRYRLISC
GOR V     CSFKITTN IRGKVQKEYALFY ELDIVPIDNNSNNRYRLISC
Jufo 9    CSFKITTNIRG KVQKEYAL FYELDIVPIDNNSNNRYRLISC
Psi Pred  CSFKITTNIR GKVQKEYALFY ELDIVPIDNNSNNRYRLISC
NNPred    CSFKITTNIRGKV QKEYALFY YELDIVPIDNNSNNRYRLISC
```

▨ Helix prediction

FIG. 1C

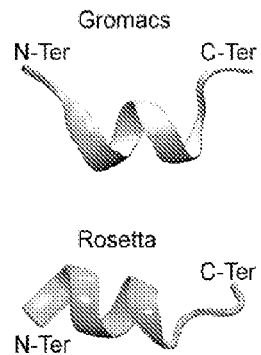

Gromacs

Rosetta

FIG. 1D

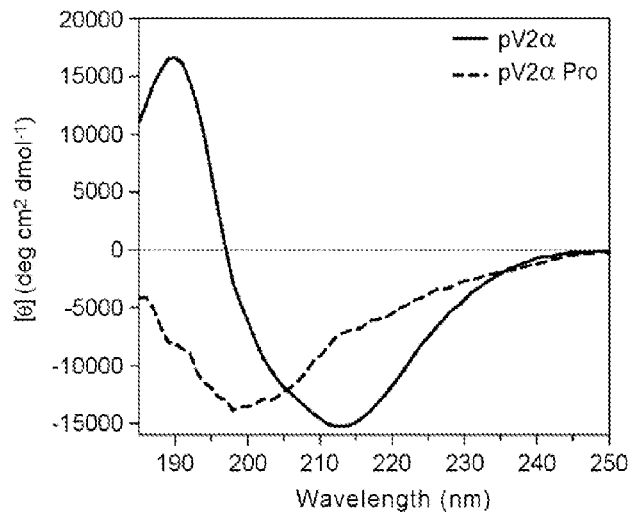

FIG. 2A
CCR5 N-Ter → S P I Y D I N Y Y T S E
                       10      14
V2 α-helix → Q K E Y A L F Y E L D I
                        173     177
FIG. 2B
FIG. 2C
FIG. 2AD
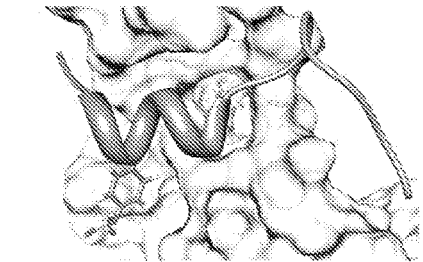
FIG. 2E
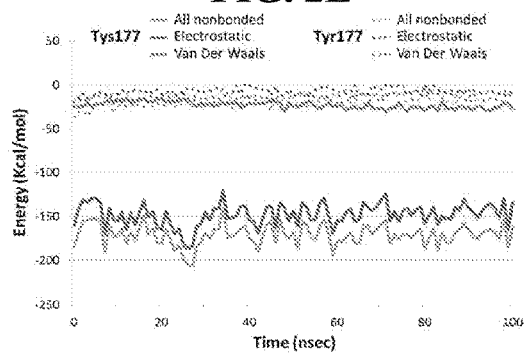
FIG. 2F
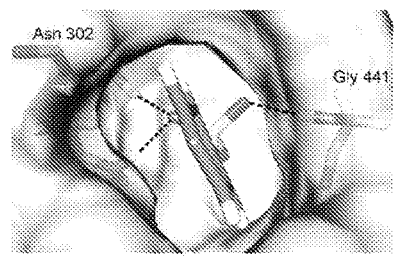
FIG. 2I
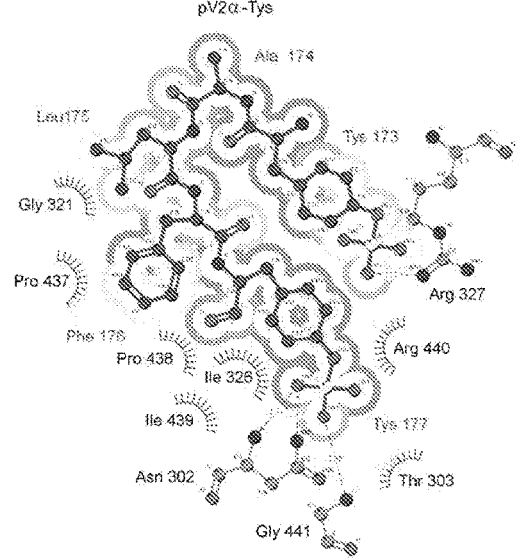
FIG. 2G
FIG. 2H
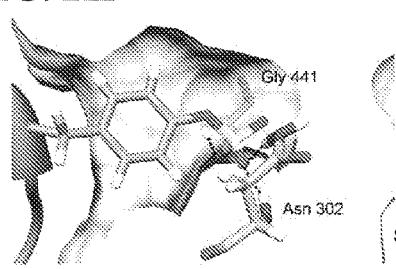
Residues of first surface
Residues of second surface
Hydrogen bond and its length
Solvent accessibility shading: ◉ Buried ● Highly accessible
His 53 Residues involved in hydrophobic contact(s)
Corresponding atoms involved in hydrophobic contact(s)

FIG. 3G
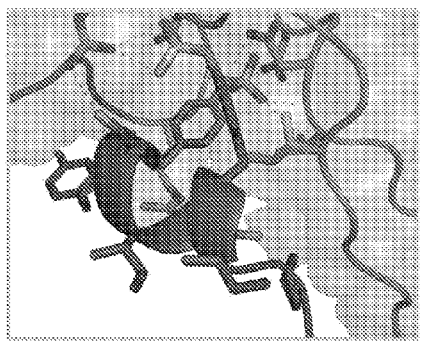 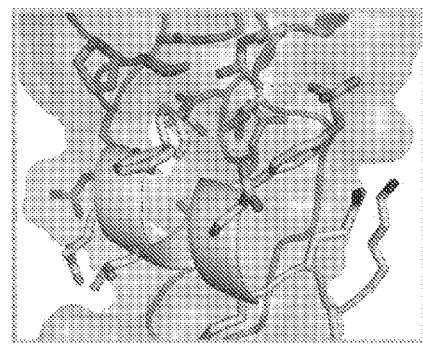
FIG. 3H
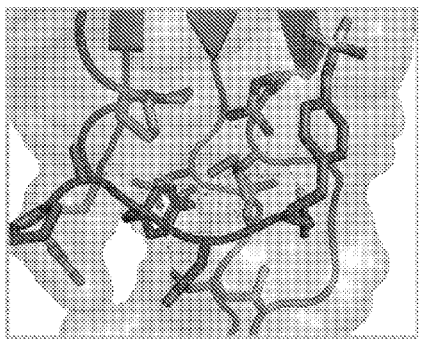 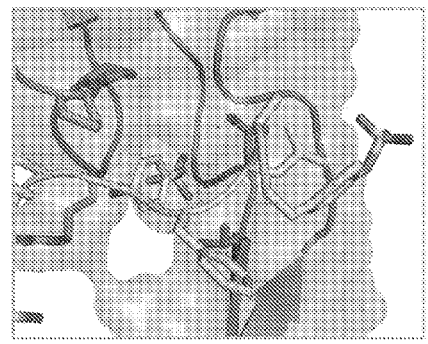

FIG. 11
Exposure of a sCD4-Induced Epitope (48d) in V2 Mutants of gp160 Treated with sCD4

Soluble CD4 interferes with mAb PG9 binding to native HIV-1 gp120

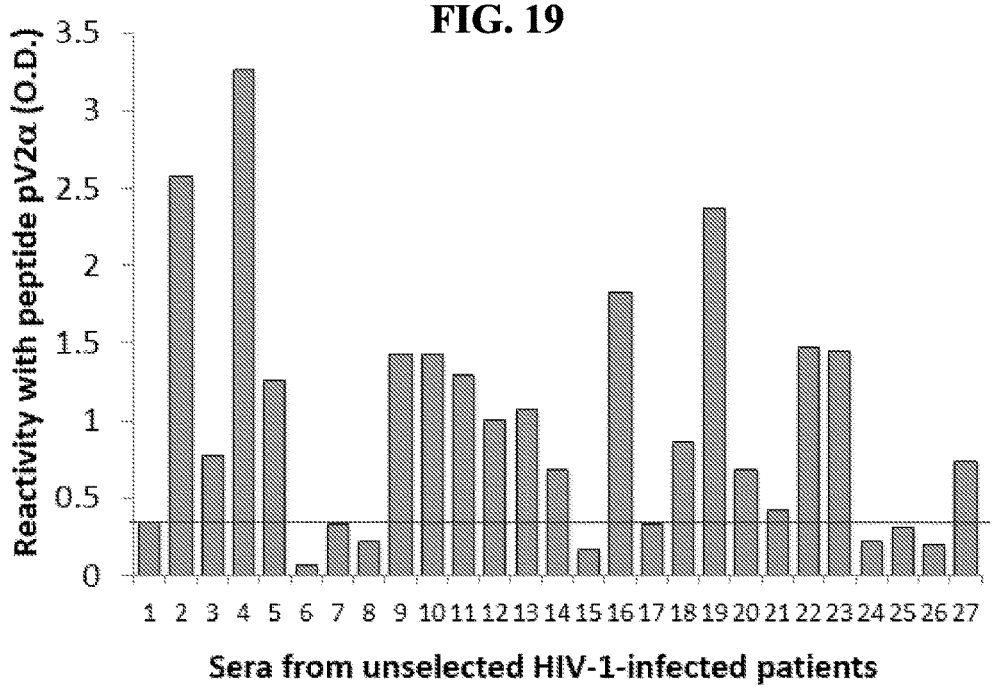
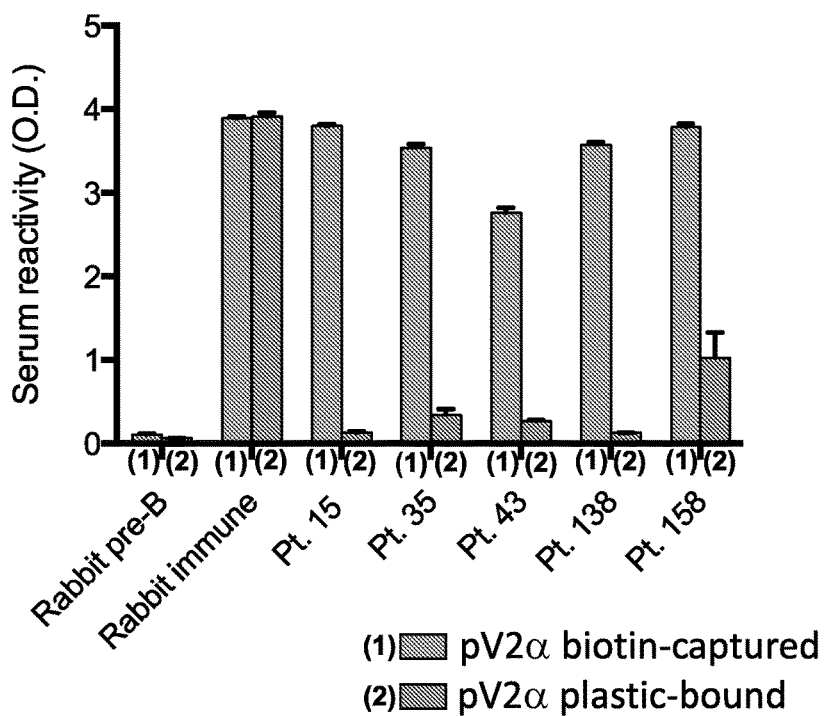

SEQUENCE LISTING

```
<160> NUMBER OF SEQ ID NOS: 43

<210> SEQ ID NO 1
<211> LENGTH: 511
<212> TYPE: PRT
<213> ORGANISM: Human immunodeficiency virus type 1

<400> SEQUENCE: 1

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190
```

```
Leu Thr Ser Cys Asn Thr Ser Val Ile Thr Gln Ala Cys Pro Lys Val
            195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
                260                 265                 270

Arg Ser Val Asn Phe Thr Asp Asn Ala Lys Thr Ile Ile Val Gln Leu
            275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
    355                 360                 365

Pro Glu Ile Val Thr His Ser Phe Asn Cys Gly Gly Glu Phe Phe Tyr
370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415

Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
    435                 440                 445

Ile Thr Gly Leu Leu Leu Thr Arg Asp Gly Gly Asn Ser Asn Asn Glu
    450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg
            500                 505                 510

<210> SEQ ID NO 2
<211> LENGTH: 8
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X is E or V
<220> FEATURE:
<221> NAME/KEY: MISC_FEATURE
<222> LOCATION: (4)..(4)
<223> OTHER INFORMATION: X is A or S
<220> FEATURE:
<221> NAME/KEY: MISC_FEATURE
<222> LOCATION: (8)..(8)
```

```
<223> OTHER INFORMATION: X is E, K or R

<400> SEQUENCE: 2

Lys Xaa Tyr Xaa Leu Phe Tyr Xaa
1               5

<210> SEQ ID NO 3
<211> LENGTH: 8
<212> TYPE: PRT
<213> ORGANISM: Human immunodeficiency virus type 1

<400> SEQUENCE: 3

Lys Glu Tyr Ala Leu Phe Tyr Glu
1               5

<210> SEQ ID NO 4
<211> LENGTH: 8
<212> TYPE: PRT
<213> ORGANISM: Human immunodeficiency virus type 1

<400> SEQUENCE: 4

Lys Glu Tyr Ala Leu Phe Tyr Lys
1               5

<210> SEQ ID NO 5
<211> LENGTH: 8
<212> TYPE: PRT
<213> ORGANISM: Human immunodeficiency virus type 1

<400> SEQUENCE: 5

Lys Val Tyr Ser Leu Phe Tyr Arg
1               5

<210> SEQ ID NO 6
<211> LENGTH: 8
<212> TYPE: PRT
<213> ORGANISM: Human immunodeficiency virus type 1

<400> SEQUENCE: 6

Lys Glu Tyr Ala Leu Phe Tyr Arg
1               5

<210> SEQ ID NO 7
<211> LENGTH: 18
<212> TYPE: PRT
<213> ORGANISM: Artificial sequence
<220> FEATURE:
<223> OTHER INFORMATION: Consensus sequence
<220> FEATURE:
<221> NAME/KEY: MISC_FEATURE
<222> LOCATION: (2)..(2)
<223> OTHER INFORMATION: X is V or K
<220> FEATURE:
<221> NAME/KEY: MISC_FEATURE
<222> LOCATION: (3)..(3)
<223> OTHER INFORMATION: X is Q or K
<220> FEATURE:
<221> NAME/KEY: MISC_FEATURE
<222> LOCATION: (4)..(4)
<223> OTHER INFORMATION: X is K or Q
<220> FEATURE:
<221> NAME/KEY: MISC_FEATURE
<222> LOCATION: (5)..(5)
<223> OTHER INFORMATION: X is E or V
<220> FEATURE:
<221> NAME/KEY: MISC_FEATURE
<222> LOCATION: (6)..(6)
<223> OTHER INFORMATION: X is Y or H
<220> FEATURE:
```

```
<221> NAME/KEY: MISC_FEATURE
<222> LOCATION: (7)..(7)
<223> OTHER INFORMATION: X is A or S
<220> FEATURE:
<221> NAME/KEY: MISC_FEATURE
<222> LOCATION: (11)..(11)
<223> OTHER INFORMATION: X is E or K, or R
<220> FEATURE:
<221> NAME/KEY: MISC_FEATURE
<222> LOCATION: (14)..(14)
<223> OTHER INFORMATION: X is I or V
<220> FEATURE:
<221> NAME/KEY: MISC_FEATURE
<222> LOCATION: (16)..(16)
<223> OTHER INFORMATION: X is P or Q
<220> FEATURE:
<221> NAME/KEY: MISC_FEATURE
<222> LOCATION: (18)..(18)
<223> OTHER INFORMATION: X is D or N

<400> SEQUENCE: 7

Lys Xaa Xaa Xaa Xaa Xaa Leu Phe Tyr Xaa Leu Asp Xaa Val Xaa
1               5                   10                  15

Ile Xaa

<210> SEQ ID NO 8
<211> LENGTH: 18
<212> TYPE: PRT
<213> ORGANISM: Human immunodeficiency virus type 1

<400> SEQUENCE: 8

Lys Val Gln Lys Glu Tyr Ala Leu Phe Tyr Glu Leu Asp Ile Val Pro
1               5                   10                  15

Ile Asp

<210> SEQ ID NO 9
<211> LENGTH: 18
<212> TYPE: PRT
<213> ORGANISM: Human immunodeficiency virus type 1

<400> SEQUENCE: 9

Lys Val Gln Lys Glu Tyr Ala Leu Phe Tyr Lys Leu Asp Val Val Pro
1               5                   10                  15

Ile Asp

<210> SEQ ID NO 10
<211> LENGTH: 18
<212> TYPE: PRT
<213> ORGANISM: Human immunodeficiency virus type 1

<400> SEQUENCE: 10

Lys Lys Gln Lys Val Tyr Ser Leu Phe Tyr Arg Leu Asp Val Val Gln
1               5                   10                  15

Ile Asn

<210> SEQ ID NO 11
<211> LENGTH: 18
<212> TYPE: PRT
<213> ORGANISM: Human immunodeficiency virus type 1

<400> SEQUENCE: 11

Lys Lys Lys Lys Glu Tyr Ala Leu Phe Tyr Arg Leu Asp Ile Val Pro
1               5                   10                  15

Leu Asn
```

<210> SEQ ID NO 12
<211> LENGTH: 18
<212> TYPE: PRT
<213> ORGANISM: Human immunodeficiency virus type 1

<400> SEQUENCE: 12

Lys Lys Lys Gln Val His Ala Leu Phe Tyr Lys Leu Asp Val Val Gln
1               5                   10                  15

Ile Asp

<210> SEQ ID NO 13
<211> LENGTH: 18
<212> TYPE: PRT
<213> ORGANISM: Human immunodeficiency virus type 1

<400> SEQUENCE: 13

Lys Lys Gln Lys Val His Ala Leu Phe Tyr Lys Leu Asp Ile Val Gln
1               5                   10                  15

Ile Glu

<210> SEQ ID NO 14
<211> LENGTH: 18
<212> TYPE: PRT
<213> ORGANISM: Human immunodeficiency virus type 1

<400> SEQUENCE: 14

Lys Lys Lys Lys Val His Ala Leu Phe Tyr Arg Leu Asp Ile Val Pro
1               5                   10                  15

Ile Asn

<210> SEQ ID NO 15
<211> LENGTH: 29
<212> TYPE: PRT
<213> ORGANISM: Human immunodeficiency virus type 1

<400> SEQUENCE: 15

Cys Ser Phe Asn Met Thr Thr Glu Leu Arg Asp Lys Lys Gln Lys Val
1               5                   10                  15

Tyr Ser Leu Phe Tyr Arg Leu Asp Val Val Gln Ile Asn
            20                  25

<210> SEQ ID NO 16
<211> LENGTH: 29
<212> TYPE: PRT
<213> ORGANISM: Human immunodeficiency virus type 1

<400> SEQUENCE: 16

Cys Ser Phe Asn Ile Thr Thr Ser Ile Arg Asp Lys Val Gln Lys Glu
1               5                   10                  15

Tyr Ala Leu Phe Tyr Lys Leu Asp Val Val Pro Ile Asp
            20                  25

<210> SEQ ID NO 17
<211> LENGTH: 29
<212> TYPE: PRT
<213> ORGANISM: Human immunodeficiency virus type 1

<400> SEQUENCE: 17

Cys Ser Phe Asn Ala Thr Thr Glu Ile Arg Asp Lys Lys Lys Lys Glu
1               5                   10                  15

Tyr Ala Leu Phe Tyr Arg Leu Asp Ile Val Pro Leu Asn

<210> SEQ ID NO 18
<211> LENGTH: 29
<212> TYPE: PRT
<213> ORGANISM: Human immunodeficiency virus type 1

<400> SEQUENCE: 18

Cys Ser Phe Asn Ile Thr Thr Glu Val Arg Asp Lys Lys Gln Val
1               5                   10                  15

His Ala Leu Phe Tyr Lys Leu Asp Val Val Gln Ile Asp
            20                  25

<210> SEQ ID NO 19
<211> LENGTH: 29
<212> TYPE: PRT
<213> ORGANISM: Human immunodeficiency virus type 1

<400> SEQUENCE: 19

Cys Ser Phe Asn Met Thr Thr Glu Leu Arg Asp Lys Lys Gln Lys Val
1               5                   10                  15

His Ala Leu Phe Tyr Lys Leu Asp Ile Val Gln Ile Glu
            20                  25

<210> SEQ ID NO 20
<211> LENGTH: 29
<212> TYPE: PRT
<213> ORGANISM: Human immunodeficiency virus type 1

<400> SEQUENCE: 20

Cys Ser Phe Asn Met Thr Thr Glu Val Arg Asp Lys Lys Lys Val
1               5                   10                  15

His Ala Leu Phe Tyr Arg Leu Asp Ile Val Pro Ile Asn
            20                  25

<210> SEQ ID NO 21
<211> LENGTH: 41
<212> TYPE: PRT
<213> ORGANISM: Human immunodeficiency virus type 1

<400> SEQUENCE: 21

Cys Ser Phe Lys Ile Thr Thr Asn Ile Arg Gly Lys Val Gln Lys Glu
1               5                   10                  15

Tyr Ala Leu Phe Tyr Glu Leu Asp Ile Val Pro Ile Asp Asn Asn Ser
            20                  25                  30

Asn Asn Arg Tyr Arg Leu Ile Ser Cys
            35                  40

<210> SEQ ID NO 22
<211> LENGTH: 12
<212> TYPE: PRT
<213> ORGANISM: Human immunodeficiency virus type 1

<400> SEQUENCE: 22

Ser Pro Ile Tyr Asp Ile Asn Tyr Tyr Thr Ser Glu
1               5                   10

<210> SEQ ID NO 23
<211> LENGTH: 845
<212> TYPE: PRT
<213> ORGANISM: Human immunodeficiency virus type 1

<400> SEQUENCE: 23

-continued

```
Met Arg Val Met Gly Ile Gln Arg Asn Cys Gln His Leu Leu Arg Trp
1               5                   10                  15

Gly Thr Met Ile Leu Gly Met Ile Ile Cys Ser Ala Ala Glu Asn
            20                  25                  30

Leu Trp Val Thr Val Tyr Tyr Gly Val Pro Val Trp Lys Asp Ala Glu
        35                  40                  45

Thr Thr Leu Phe Cys Ala Ser Asp Ala Lys Ala Tyr Glu Thr Glu Met
    50                  55                  60

His Asn Val Trp Ala Thr His Ala Cys Val Pro Thr Asp Pro Asn Pro
65                  70                  75                  80

Gln Glu Ile His Leu Glu Asn Val Thr Glu Glu Phe Asn Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Ser Asn Val Asn Val Thr Asn Asn Thr Thr Asn Thr His Glu
    130                 135                 140

Glu Ile Lys Asn Cys Ser Phe Asn Met Thr Thr Glu Leu Arg Asp
145                 150                 155                 160

Lys Lys Gln Lys Val Tyr Ser Leu Phe Tyr Arg Leu Asp Val Val Gln
                165                 170                 175

Ile Asn Glu Asn Asn Ser Asn Ser Ser Tyr Arg Leu Ile Asn Cys Asn
            180                 185                 190

Thr Ser Ala Ile Thr Gln Ala Cys Pro Lys Val Ser Phe Glu Pro Ile
        195                 200                 205

Pro Ile His Tyr Cys Ala Pro Ala Gly Phe Ala Ile Leu Lys Cys Lys
    210                 215                 220

Asp Lys Glu Phe Asn Gly Thr Gly Pro Cys Lys Asn Val Ser Thr Val
225                 230                 235                 240

Gln Cys Thr His Gly Ile Lys Pro Val Val Ser Thr Gln Leu Leu Leu
                245                 250                 255

Asn Gly Ser Leu Ala Glu Glu Val Ile Ile Arg Ser Glu Asn Ile
            260                 265                 270

Thr Asn Asn Ala Lys Thr Ile Ile Val Gln Leu Thr Lys Pro Val Lys
        275                 280                 285

Ile Asn Cys Thr Arg Pro Asn Asn Thr Arg Lys Ser Ile Arg Ile
    290                 295                 300

Gly Pro Gly Gln Ala Phe Tyr Ala Thr Gly Asp Ile Ile Gly Asp Ile
305                 310                 315                 320

Arg Gln Ala His Cys Asn Val Ser Arg Ser Glu Trp Asn Lys Thr Leu
                325                 330                 335

Gln Lys Val Ala Lys Gln Leu Arg Lys Tyr Phe Lys Asn Lys Thr Ile
            340                 345                 350

Ile Phe Thr Asn Ser Ser Gly Gly Asp Leu Glu Ile Thr Thr His Ser
        355                 360                 365

Phe Asn Cys Gly Gly Glu Phe Phe Tyr Cys Asn Thr Ser Gly Leu Phe
    370                 375                 380

Asn Ser Thr Trp Asn Asn Gly Thr Met Lys Asn Thr Ile Thr Leu Pro
385                 390                 395                 400

Cys Arg Ile Lys Gln Ile Ile Asn Met Trp Gln Arg Ala Gly Gln Ala
                405                 410                 415
```

```
Met Tyr Ala Pro Pro Ile Gln Gly Val Ile Arg Cys Glu Ser Asn Ile
                420                 425                 430

Thr Gly Leu Leu Leu Thr Arg Asp Gly Asn Asn Asn Thr Asn Glu
            435                 440                 445

Thr Phe Arg Pro Gly Gly Asp Met Arg Asp Asn Trp Arg Ser Glu
        450                 455                 460

Leu Tyr Lys Tyr Lys Val Val Lys Ile Glu Pro Leu Gly Val Ala Pro
465                 470                 475                 480

Thr Arg Ala Lys Arg Arg Val Val Glu Arg Glu Lys Arg Ala Val Gly
                485                 490                 495

Ile Gly Ala Val Phe Leu Gly Phe Leu Gly Ala Ala Gly Ser Thr Met
            500                 505                 510

Gly Ala Ala Ser Ile Thr Leu Thr Val Gln Ala Arg Gln Leu Leu Ser
            515                 520                 525

Gly Ile Val Gln Gln Gln Ser Asn Leu Leu Arg Ala Ile Glu Ala Gln
            530                 535                 540

Gln His Leu Leu Lys Leu Thr Val Trp Gly Ile Lys Gln Leu Gln Ala
545                 550                 555                 560

Arg Val Leu Ala Val Glu Arg Tyr Leu Lys Asp Gln Gln Leu Leu Gly
                565                 570                 575

Ile Trp Gly Cys Ser Gly Lys Leu Ile Cys Thr Thr Asn Val Pro Trp
            580                 585                 590

Asn Ser Ser Trp Ser Asn Lys Ser Gln Asn Glu Ile Trp Asp Asn Met
            595                 600                 605

Thr Trp Leu Gln Trp Asp Lys Glu Ile Ser Asn Tyr Thr His Ile Ile
            610                 615                 620

Tyr Asn Leu Ile Glu Glu Ser Gln Asn Gln Gln Glu Lys Asn Glu Gln
625                 630                 635                 640

Asp Leu Leu Ala Leu Asp Lys Trp Ala Asn Leu Trp Asn Trp Phe Asp
                645                 650                 655

Ile Ser Asn Trp Leu Trp Tyr Ile Lys Ile Phe Ile Met Ile Val Gly
            660                 665                 670

Gly Leu Ile Gly Leu Arg Ile Val Phe Ala Val Leu Ser Val Ile Asn
            675                 680                 685

Arg Val Arg Gln Gly Tyr Ser Pro Leu Ser Phe Gln Thr His Thr Pro
            690                 695                 700

Asn Pro Arg Gly Leu Asp Arg Pro Gly Arg Ile Glu Glu Glu Gly Gly
705                 710                 715                 720

Glu Gln Gly Arg Asp Arg Ser Ile Arg Leu Val Ser Gly Phe Leu Ala
                725                 730                 735

Leu Ala Trp Asp Asp Leu Arg Ser Leu Cys Leu Phe Ser Tyr His Arg
            740                 745                 750

Leu Arg Asp Phe Ile Leu Ile Ala Ala Arg Thr Val Glu Leu Leu Gly
            755                 760                 765

His Ser Ser Leu Lys Gly Leu Arg Leu Gly Trp Glu Gly Leu Lys Tyr
            770                 775                 780

Leu Trp Asn Leu Leu Leu Tyr Trp Gly Arg Glu Leu Lys Ile Ser Ala
785                 790                 795                 800

Ile Asn Leu Val Asp Thr Ile Ala Ile Ala Val Ala Gly Trp Thr Asp
                805                 810                 815

Arg Val Ile Glu Ile Gly Gln Arg Ile Gly Arg Ala Ile Leu His Ile
            820                 825                 830

Pro Arg Arg Ile Arg Gln Gly Leu Glu Arg Ala Leu Leu
```

<210> SEQ ID NO 24
<211> LENGTH: 843
<212> TYPE: PRT
<213> ORGANISM: Human immunodeficiency virus type 1

<400> SEQUENCE: 24

```
Met Arg Val Met Gly Thr Gln Arg Asn Tyr Gln His Leu Trp Arg Trp
1               5                   10                  15
Gly Ile Leu Ile Leu Gly Met Leu Ile Met Cys Lys Ala Thr Asp Leu
            20                  25                  30
Trp Val Thr Val Tyr Tyr Gly Val Pro Val Trp Lys Asp Ala Asp Thr
        35                  40                  45
Thr Leu Phe Cys Ala Ser Asp Ala Lys Ala Tyr Asp Thr Glu Val His
    50                  55                  60
Asn Val Trp Ala Thr His Ala Cys Val Pro Thr Asp Pro Asn Pro Gln
65                  70                  75                  80
Glu Val Asn Leu Glu Asn Val Thr Glu Asp Phe Asn Met Trp Lys Asn
                85                  90                  95
Asn Met Val Glu Gln Met His Glu Asp Ile Ile Ser Leu Trp Asp Gln
            100                 105                 110
Ser Leu Lys Pro Cys Val Lys Leu Thr Pro Leu Cys Val Thr Leu Asn
        115                 120                 125
Cys Ser Asn Ala Asn Thr Thr Asn Ser Thr Met Glu Glu Ile Lys
    130                 135                 140
Asn Cys Ser Tyr Asn Ile Thr Thr Glu Leu Arg Asp Lys Thr Gln Lys
145                 150                 155                 160
Val Tyr Ser Leu Phe Tyr Lys Leu Asp Val Val Gln Leu Asp Glu Ser
                165                 170                 175
Asn Lys Ser Glu Tyr Tyr Arg Leu Ile Asn Cys Asn Thr Ser Ala
            180                 185                 190
Ile Thr Gln Ala Cys Pro Lys Val Ser Phe Glu Pro Ile Pro Ile His
        195                 200                 205
Tyr Cys Ala Pro Ala Gly Phe Ala Ile Leu Lys Cys Lys Asp Pro Arg
    210                 215                 220
Phe Asn Gly Thr Gly Ser Cys Asn Asn Val Ser Ser Val Gln Cys Thr
225                 230                 235                 240
His Gly Ile Lys Pro Val Ala Ser Thr Gln Leu Leu Leu Asn Gly Ser
                245                 250                 255
Leu Ala Glu Gly Lys Val Met Ile Arg Ser Glu Asn Ile Thr Asn Asn
            260                 265                 270
Ala Lys Asn Ile Ile Val Gln Phe Asn Lys Pro Val Pro Ile Thr Cys
        275                 280                 285
Ile Arg Pro Asn Asn Asn Thr Arg Lys Ser Ile Arg Phe Gly Pro Gly
    290                 295                 300
Gln Ala Phe Tyr Thr Asn Asp Ile Ile Gly Asp Ile Arg Gln Ala His
305                 310                 315                 320
Cys Asn Ile Asn Lys Thr Lys Trp Asn Ala Thr Leu Gln Lys Val Ala
                325                 330                 335
Glu Gln Leu Arg Glu His Phe Pro Asn Lys Thr Ile Ile Phe Thr Asn
            340                 345                 350
Ser Ser Gly Gly Asp Leu Glu Ile Thr Thr His Ser Phe Asn Cys Gly
        355                 360                 365
```

```
Gly Glu Phe Phe Tyr Cys Asn Thr Thr Gly Leu Phe Asn Ser Thr Trp
    370                 375                 380

Lys Asn Gly Thr Thr Asn Asn Thr Glu Gln Met Ile Thr Leu Pro Cys
385                 390                 395                 400

Arg Ile Lys Gln Ile Ile Asn Met Trp Gln Arg Val Gly Arg Ala Met
                405                 410                 415

Tyr Ala Pro Pro Ile Ala Gly Val Ile Lys Cys Thr Ser Asn Ile Thr
                420                 425                 430

Gly Ile Ile Leu Thr Arg Asp Gly Gly Asn Asn Glu Thr Glu Thr Phe
            435                 440                 445

Arg Pro Gly Gly Gly Asp Met Arg Asp Asn Trp Arg Ser Glu Leu Tyr
450                 455                 460

Lys Tyr Lys Val Val Lys Ile Glu Pro Leu Gly Val Ala Pro Thr Arg
465                 470                 475                 480

Ala Lys Arg Arg Val Val Glu Arg Glu Lys Arg Ala Val Gly Met Gly
                485                 490                 495

Ala Val Phe Leu Gly Phe Leu Gly Ala Ala Gly Ser Thr Met Gly Ala
            500                 505                 510

Ala Ser Ile Thr Leu Thr Val Gln Ala Arg Gln Leu Leu Ser Gly Ile
            515                 520                 525

Val Gln Gln Gln Ser Asn Leu Leu Lys Ala Ile Glu Ala Gln Gln His
530                 535                 540

Leu Leu Lys Leu Thr Val Trp Gly Ile Lys Gln Leu Gln Ala Arg Val
545                 550                 555                 560

Leu Ala Leu Glu Arg Tyr Leu Gln Asp Gln Gln Leu Leu Gly Ile Trp
                565                 570                 575

Gly Cys Ser Gly Lys Leu Ile Cys Ala Thr Thr Val Pro Trp Asn Ser
            580                 585                 590

Ser Trp Ser Asn Lys Thr Gln Glu Glu Ile Trp Asn Asn Met Thr Trp
            595                 600                 605

Leu Gln Trp Asp Lys Glu Ile Ser Asn Tyr Thr Asn Ile Ile Tyr Lys
            610                 615                 620

Leu Leu Glu Glu Ser Gln Asn Gln Gln Glu Lys Asn Glu Gln Asp Leu
625                 630                 635                 640

Leu Ala Leu Asp Lys Trp Ala Asn Leu Trp Asn Trp Phe Asn Ile Thr
                645                 650                 655

Asn Trp Leu Trp Tyr Ile Arg Ile Phe Ile Met Ile Val Gly Gly Leu
                660                 665                 670

Ile Gly Leu Arg Ile Val Ile Ala Ile Ile Ser Val Val Asn Arg Val
            675                 680                 685

Arg Gln Gly Tyr Ser Pro Leu Ser Phe Gln Ile Pro Thr Pro Asn Pro
690                 695                 700

Glu Gly Leu Asp Arg Pro Gly Arg Ile Glu Glu Gly Gly Glu Gln
705                 710                 715                 720

Gly Arg Asp Arg Ser Ile Arg Leu Val Ser Gly Phe Leu Ala Leu Ala
                725                 730                 735

Trp Asp Asp Leu Arg Ser Leu Cys Leu Phe Ser Tyr His Arg Leu Arg
            740                 745                 750

Asp Cys Ile Leu Ile Ala Ala Arg Thr Val Glu Leu Leu Gly His Ser
            755                 760                 765

Ser Leu Lys Gly Leu Arg Leu Gly Trp Glu Gly Leu Lys Tyr Leu Trp
770                 775                 780

Asn Leu Leu Leu Tyr Trp Gly Arg Glu Leu Lys Asn Ser Ala Ile Ser
```

```
                  785                 790                 795                 800
Leu Leu Asp Thr Ile Ala Val Ala Val Ala Glu Trp Thr Asp Arg Val
                805                 810                 815
Ile Glu Ile Gly Gln Arg Ala Cys Arg Ala Ile Leu Asn Ile Pro Arg
                820                 825                 830
Arg Ile Arg Gln Gly Phe Glu Arg Ala Leu Leu
                835                 840

<210> SEQ ID NO 25
<211> LENGTH: 841
<212> TYPE: PRT
<213> ORGANISM: Human immunodeficiency virus type 1

<400> SEQUENCE: 25

Met Arg Val Lys Gly Ile Arg Lys Asn Tyr Gln His Leu Trp Arg Trp
1               5                   10                  15
Gly Thr Met Leu Leu Gly Met Leu Met Ile Cys Ser Ala Ala Glu Lys
                20                  25                  30
Leu Trp Val Thr Val Tyr Tyr Gly Val Pro Val Trp Lys Glu Ala Thr
            35                  40                  45
Thr Thr Leu Phe Cys Ala Ser Asp Ala Lys Ala Tyr Asp Thr Glu Val
        50                  55                  60
His Asn Val Trp Ala Thr His Ala Cys Val Pro Thr Asp Pro Asn Pro
65                  70                  75                  80
Gln Glu Val Val Leu Glu Asn Val Thr Glu Asn Phe Asn Met Trp Lys
                85                  90                  95
Asn Asn Met Val Glu Gln Met His Glu Asp Ile Ile Ser Leu Trp Asp
                100                 105                 110
Gln Ser Leu Lys Pro Cys Val Lys Leu Thr Pro Leu Cys Val Thr Leu
            115                 120                 125
Asn Cys Thr Asp Leu Met Asn Ala Thr Asn Thr Asn Thr Thr Ile Ile
        130                 135                 140
Tyr Arg Trp Arg Gly Glu Ile Lys Asn Cys Ser Phe Asn Ile Thr Thr
145                 150                 155                 160
Ser Ile Arg Asp Lys Val Gln Lys Glu Tyr Ala Leu Phe Tyr Lys Leu
                165                 170                 175
Asp Val Val Pro Ile Asp Asn Asp Asn Thr Ser Tyr Arg Leu Ile Ser
                180                 185                 190
Cys Asn Thr Ser Val Ile Thr Gln Ala Cys Pro Lys Val Ser Phe Glu
            195                 200                 205
Pro Ile Pro Ile His Tyr Cys Ala Pro Ala Gly Phe Ala Ile Leu Lys
        210                 215                 220
Cys Asn Asp Lys Lys Phe Asn Gly Thr Gly Pro Cys Thr Asn Val Ser
225                 230                 235                 240
Thr Val Gln Cys Thr His Gly Ile Arg Pro Val Val Ser Thr Gln Leu
                245                 250                 255
Leu Leu Asn Gly Ser Leu Ala Glu Glu Val Val Ile Arg Ser Glu
                260                 265                 270
Asn Phe Thr Asp Asn Ala Lys Thr Ile Ile Val Gln Leu Asn Glu Ser
            275                 280                 285
Val Glu Ile Asn Cys Thr Arg Pro Asn Asn Asn Thr Arg Lys Ser Ile
        290                 295                 300
His Ile Gly Pro Gly Arg Ala Phe Tyr Thr Thr Gly Glu Ile Ile Gly
305                 310                 315                 320
```

Asp Ile Arg Gln Ala His Cys Asn Ile Ser Arg Ala Lys Trp Asn Asn
            325                 330                 335

Thr Leu Lys Gln Ile Val Lys Lys Leu Arg Glu Gln Phe Gly Asn Lys
            340                 345                 350

Thr Ile Val Phe Asn Gln Ser Ser Gly Gly Asp Pro Glu Ile Val Met
            355                 360                 365

His Ser Phe Asn Cys Gly Gly Glu Phe Phe Tyr Cys Asn Thr Thr Gln
            370                 375                 380

Leu Phe Asn Ser Thr Trp Asn Gly Thr Trp Asn Asn Thr Glu Gly Asn
385                 390                 395                 400

Ile Thr Leu Pro Cys Arg Ile Lys Gln Ile Ile Asn Met Trp Gln Glu
            405                 410                 415

Val Gly Lys Ala Met Tyr Ala Pro Pro Ile Arg Gly Gln Ile Arg Cys
            420                 425                 430

Ser Ser Asn Ile Thr Gly Leu Leu Leu Thr Arg Asp Gly Gly Asn Asn
            435                 440                 445

Glu Thr Glu Ile Phe Arg Pro Gly Gly Gly Asp Met Arg Asp Asn Trp
            450                 455                 460

Arg Ser Glu Leu Tyr Lys Tyr Lys Val Val Lys Ile Glu Pro Leu Gly
465                 470                 475                 480

Val Ala Pro Thr Lys Ala Lys Arg Arg Val Val Gln Arg Glu Lys Arg
            485                 490                 495

Ala Val Gly Ile Gly Ala Met Phe Leu Gly Phe Leu Gly Ala Ala Gly
            500                 505                 510

Ser Thr Met Gly Ala Ala Ser Met Thr Leu Thr Val Gln Ala Arg Gln
            515                 520                 525

Leu Leu Ser Gly Ile Val Gln Gln Gln Asn Asn Leu Leu Arg Ala Ile
            530                 535                 540

Glu Ala Gln Gln His Leu Leu Gln Leu Thr Val Trp Gly Ile Lys Gln
545                 550                 555                 560

Leu Gln Ala Arg Val Leu Ala Val Glu Arg Tyr Leu Lys Asp Gln Gln
            565                 570                 575

Leu Leu Gly Ile Trp Gly Cys Ser Gly Lys Leu Ile Cys Thr Thr Ala
            580                 585                 590

Val Pro Trp Asn Ala Ser Trp Ser Asn Lys Ser Leu Asp Glu Ile Trp
            595                 600                 605

Asp Asn Met Thr Trp Met Glu Trp Glu Arg Glu Ile Asp Asn Tyr Thr
            610                 615                 620

Ser Leu Ile Tyr Thr Leu Ile Glu Glu Ser Gln Asn Gln Gln Glu Lys
625                 630                 635                 640

Asn Glu Gln Glu Leu Leu Glu Leu Asp Lys Trp Ala Ser Leu Trp Asn
            645                 650                 655

Trp Phe Asp Ile Thr Asn Trp Leu Trp Tyr Ile Lys Ile Phe Ile Met
            660                 665                 670

Ile Val Gly Gly Leu Val Gly Leu Arg Ile Val Phe Ala Val Leu Ser
            675                 680                 685

Ile Val Asn Arg Val Arg Gln Gly Tyr Ser Pro Leu Ser Phe Gln Thr
            690                 695                 700

Arg Leu Pro Ala Pro Arg Gly Pro Asp Arg Pro Glu Gly Ile Glu Glu
705                 710                 715                 720

Glu Gly Gly Glu Arg Asp Arg Asp Arg Ser Gly Arg Leu Val Asp Gly
            725                 730                 735

Phe Leu Ala Leu Ile Trp Asp Asp Leu Arg Ser Leu Cys Leu Phe Ser

```
                  740                 745                 750
Tyr His Arg Leu Arg Asp Leu Leu Ile Val Thr Arg Ile Val Glu
            755                 760                 765

Leu Leu Gly Arg Arg Gly Trp Glu Val Leu Lys Tyr Trp Trp Asn Leu
        770                 775                 780

Leu Gln Tyr Trp Ser Gln Glu Leu Lys Asn Ser Ala Val Ser Leu Leu
785                 790                 795                 800

Asn Ala Thr Ala Ile Ala Val Ala Glu Gly Thr Asp Arg Val Ile Glu
            805                 810                 815

Val Val Gln Arg Ala Cys Arg Ala Ile Leu His Ile Pro Arg Arg Ile
        820                 825                 830

Arg Gln Gly Leu Glu Arg Ala Leu Leu
        835                 840

<210> SEQ ID NO 26
<211> LENGTH: 835
<212> TYPE: PRT
<213> ORGANISM: Human immunodeficiency virus type 1

<400> SEQUENCE: 26

Met Arg Val Arg Gly Ile Leu Arg Asn Cys Gln Gln Trp Trp Ile Trp
1               5                   10                  15

Gly Ile Leu Gly Phe Trp Met Leu Met Ile Cys Asn Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Ala Ser Asp Ala Lys Ala Tyr Glu Lys Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asn Ala Thr Asn Ala Thr Asn Thr Met Gly Glu Ile Lys
    130                 135                 140

Asn Cys Ser Phe Asn Ile Thr Thr Glu Leu Arg Asp Lys Lys Gln Lys
145                 150                 155                 160

Val Tyr Ala Leu Phe Tyr Arg Leu Asp Ile Val Pro Leu Asn Glu Asn
                165                 170                 175

Asn Ser Tyr Arg Leu Ile Asn Cys Asn Thr Ser Ala Ile Thr Gln Ala
            180                 185                 190

Cys Pro Lys Val Ser Phe Asp Pro Ile Pro Ile His Tyr Cys Ala Pro
        195                 200                 205

Ala Gly Tyr Ala Ile Leu Lys Cys Asn Asn Lys Thr Phe Asn Gly Thr
    210                 215                 220

Gly Pro Cys Asn Asn Val Ser Thr Val Gln Cys Thr His Gly Ile Lys
225                 230                 235                 240

Pro Val Val Ser Thr Gln Leu Leu Leu Asn Gly Ser Leu Ala Glu Glu
                245                 250                 255

Glu Ile Ile Ile Arg Ser Glu Asn Leu Thr Asn Asn Ala Lys Thr Ile
            260                 265                 270
```

```
Ile Val His Leu Asn Glu Ser Glu Ile Val Cys Thr Arg Pro Asn
            275                 280                 285
Asn Asn Thr Arg Lys Ser Ile Arg Ile Gly Pro Gly Gln Thr Phe Tyr
290                 295                 300
Ala Thr Gly Asp Ile Ile Gly Asp Ile Arg Gln Ala His Cys Asn Ile
305                 310                 315                 320
Ser Glu Asp Lys Trp Asn Lys Thr Leu Gln Lys Val Ser Lys Lys Leu
                325                 330                 335
Lys Glu His Phe Pro Asn Lys Thr Ile Lys Phe Glu Pro Ser Ser Gly
            340                 345                 350
Gly Asp Leu Glu Ile Thr Thr His Ser Phe Asn Cys Arg Gly Glu Phe
        355                 360                 365
Phe Tyr Cys Asn Thr Ser Lys Leu Phe Asn Ser Thr Tyr Asn Ser Thr
    370                 375                 380
Asn Ser Thr Ile Thr Leu Pro Cys Arg Ile Lys Gln Ile Ile Asn Met
385                 390                 395                 400
Trp Gln Glu Val Gly Arg Ala Met Tyr Ala Pro Pro Ile Ala Gly Asn
                405                 410                 415
Ile Thr Cys Lys Ser Asn Ile Thr Gly Leu Leu Leu Thr Arg Asp Gly
            420                 425                 430
Gly Lys Asn Asn Thr Glu Thr Phe Arg Pro Gly Gly Gly Asp Met Arg
        435                 440                 445
Asp Asn Trp Arg Ser Glu Leu Tyr Lys Tyr Lys Val Val Glu Ile Lys
    450                 455                 460
Pro Leu Gly Ile Ala Pro Thr Lys Ala Lys Arg Arg Val Val Glu Arg
465                 470                 475                 480
Glu Lys Arg Ala Val Gly Ile Gly Ala Val Phe Leu Gly Phe Leu Gly
                485                 490                 495
Ala Ala Gly Ser Thr Met Gly Ala Ala Ser Ile Thr Leu Thr Val Gln
            500                 505                 510
Ala Arg Gln Leu Leu Ser Gly Ile Val Gln Gln Ser Asn Leu Leu
        515                 520                 525
Arg Ala Ile Glu Ala Gln Gln His Met Leu Gln Leu Thr Val Trp Gly
    530                 535                 540
Ile Lys Gln Leu Gln Thr Arg Val Leu Ala Ile Glu Arg Tyr Leu Lys
545                 550                 555                 560
Asp Gln Gln Leu Leu Gly Ile Trp Gly Cys Ser Gly Lys Leu Ile Cys
                565                 570                 575
Thr Thr Ala Val Pro Trp Asn Ser Ser Trp Ser Asn Lys Ser Gln Glu
            580                 585                 590
Asp Ile Trp Asp Asn Met Thr Trp Met Gln Trp Asp Arg Glu Ile Ser
        595                 600                 605
Asn Tyr Thr Asp Thr Ile Tyr Arg Leu Leu Glu Asp Ser Gln Asn Gln
    610                 615                 620
Gln Glu Lys Asn Glu Lys Asp Leu Leu Ala Leu Asp Ser Trp Lys Asn
625                 630                 635                 640
Leu Trp Asn Trp Phe Asp Ile Thr Asn Trp Leu Trp Tyr Ile Lys Ile
                645                 650                 655
Phe Ile Met Ile Val Gly Gly Leu Ile Gly Leu Arg Ile Ile Phe Ala
            660                 665                 670
Val Leu Ser Ile Val Asn Arg Val Arg Gln Gly Tyr Ser Pro Leu Ser
        675                 680                 685
Phe Gln Thr Leu Thr Pro Asn Pro Arg Gly Pro Asp Arg Leu Gly Arg
```

```
                    690                 695                 700
Ile Glu Glu Gly Gly Glu Gln Asp Arg Asp Arg Ser Ile Arg Leu
705                 710                 715                 720

Val Ser Gly Phe Leu Ala Leu Ala Trp Asp Asp Leu Arg Ser Leu Cys
                725                 730                 735

Leu Phe Ser Tyr His Arg Leu Arg Asp Phe Ile Leu Ile Ala Ala Arg
                740                 745                 750

Ala Val Glu Leu Leu Gly Arg Ser Ser Leu Arg Gly Leu Gln Arg Gly
                755                 760                 765

Trp Glu Ala Leu Lys Tyr Leu Gly Ser Leu Val Gln Tyr Trp Gly Leu
770                 775                 780

Glu Leu Lys Lys Ser Ala Ile Ser Leu Leu Asp Thr Ile Ala Ile Ala
785                 790                 795                 800

Val Ala Glu Gly Thr Asp Arg Ile Ile Glu Leu Ile Gln Arg Ile Cys
                805                 810                 815

Arg Ala Ile Arg Asn Ile Pro Arg Arg Ile Arg Gln Gly Phe Glu Ala
                820                 825                 830

Ala Leu Gln
        835

<210> SEQ ID NO 27
<211> LENGTH: 840
<212> TYPE: PRT
<213> ORGANISM: Human immunodeficiency virus type 1

<400> SEQUENCE: 27

Met Arg Val Arg Gly Ile Gln Arg Asn Tyr Gln His Leu Trp Arg Trp
1               5                   10                  15

Gly Ile Met Leu Leu Gly Met Leu Met Ile Cys Ser Val Ala Glu Asn
                20                  25                  30

Leu Trp Val Thr Val Tyr Tyr Gly Val Pro Val Trp Lys Glu Ala Thr
                35                  40                  45

Thr Thr Leu Phe Cys Ala Ser Asp Ala Lys Ser Tyr Lys Thr Glu Ala
            50                  55                  60

His Asn Ile Trp Ala Thr His Ala Cys Val Pro Thr Asp Pro Asn Pro
65              70                  75                  80

Gln Glu Ile Glu Leu Glu Asn Val Thr Glu Asn Phe Asn Met Trp Lys
                85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
            115                 120                 125

Asn Cys Thr Asp Val Lys Arg Asn Asn Thr Ser Asn Asp Thr Asn Glu
130                 135                 140

Gly Glu Met Lys Asn Cys Ser Phe Asn Ile Thr Thr Glu Ile Arg Asp
145                 150                 155                 160

Lys Lys Lys Gln Val His Ala Leu Phe Tyr Lys Leu Asp Val Val Pro
                165                 170                 175

Ile Asp Asp Asn Asn Ser Asn Thr Ser Tyr Arg Leu Ile Asn Cys Asn
                180                 185                 190

Thr Ser Ala Ile Thr Gln Ala Cys Pro Lys Val Thr Phe Glu Pro Ile
            195                 200                 205

Pro Ile His Tyr Cys Ala Pro Ala Gly Phe Ala Ile Leu Lys Cys Lys
            210                 215                 220
```

```
Asp Lys Lys Phe Asn Gly Thr Gly Pro Cys Lys Asn Val Ser Thr Val
225                 230                 235                 240

Gln Cys Thr His Gly Ile Arg Pro Val Val Ser Thr Gln Leu Leu Leu
            245                 250                 255

Asn Gly Ser Leu Ala Glu Glu Ile Ile Ile Arg Ser Glu Asn Leu
        260                 265                 270

Thr Asn Asn Ala Lys Ile Ile Ile Val Gln Leu Asn Glu Ser Val Thr
    275                 280                 285

Ile Asn Cys Thr Arg Pro Tyr Asn Asn Thr Arg Gln Arg Thr Pro Ile
    290                 295                 300

Gly Pro Gly Gln Ala Leu Tyr Thr Thr Arg Ile Lys Gly Asp Ile Arg
305                 310                 315                 320

Gln Ala His Cys Asn Ile Ser Arg Ala Glu Trp Asn Lys Thr Leu Gln
                325                 330                 335

Gln Val Ala Lys Lys Leu Gly Asp Leu Leu Asn Lys Thr Thr Ile Ile
            340                 345                 350

Phe Lys Pro Ser Ser Gly Gly Asp Pro Glu Ile Thr Thr His Ser Phe
        355                 360                 365

Asn Cys Gly Gly Glu Phe Phe Tyr Cys Asn Thr Ser Arg Leu Phe Asn
370                 375                 380

Ser Thr Trp Asn Asn Thr Lys Trp Asn Ser Thr Gly Lys Ile Thr Leu
385                 390                 395                 400

Pro Cys Arg Ile Lys Gln Ile Ile Asn Met Trp Gln Gly Val Gly Lys
                405                 410                 415

Ala Met Tyr Ala Pro Pro Ile Glu Gly Leu Ile Lys Cys Ser Ser Asn
            420                 425                 430

Ile Thr Gly Leu Leu Leu Thr Arg Asp Gly Gly Ala Asn Asn Ser His
        435                 440                 445

Asn Glu Thr Phe Arg Pro Gly Gly Gly Asp Met Arg Asp Asn Trp Arg
    450                 455                 460

Ser Glu Leu Tyr Lys Tyr Lys Val Val Lys Ile Glu Pro Leu Gly Val
465                 470                 475                 480

Ala Pro Thr Arg Ala Lys Arg Arg Val Val Glu Arg Glu Lys Arg Ala
            485                 490                 495

Ile Gly Leu Gly Ala Met Phe Leu Gly Phe Leu Gly Ala Ala Gly Ser
        500                 505                 510

Thr Met Gly Ala Ala Ser Met Thr Leu Thr Val Gln Ala Arg Gln Leu
    515                 520                 525

Leu Ser Gly Ile Val Gln Gln Asn Asn Leu Leu Arg Ala Ile Glu
530                 535                 540

Ala Gln Gln His Leu Leu Gln Leu Thr Val Trp Gly Ile Lys Gln Leu
545                 550                 555                 560

Gln Ala Arg Ile Leu Ala Val Glu Arg Tyr Leu Lys Asp Gln Gln Leu
                565                 570                 575

Leu Gly Ile Trp Gly Cys Ser Gly Lys His Ile Cys Thr Thr Thr Val
            580                 585                 590

Pro Trp Asn Ser Ser Trp Ser Asn Lys Ser Leu Asp Glu Ile Trp Asn
        595                 600                 605

Asn Met Thr Trp Met Glu Trp Glu Arg Glu Ile Asp Asn Tyr Thr Gly
    610                 615                 620

Leu Ile Tyr Ser Leu Ile Glu Glu Ser Gln Asn Gln Gln Glu Lys Asn
625                 630                 635                 640

Glu Gln Glu Leu Leu Glu Leu Asp Lys Trp Ala Ser Leu Trp Asn Trp
```

-continued

```
                          645                 650                 655
Phe Ser Ile Thr Gln Trp Leu Trp Tyr Ile Lys Ile Phe Ile Met Ile
                660                 665                 670

Val Gly Gly Leu Ile Gly Leu Arg Ile Val Phe Ala Val Leu Ser Leu
            675                 680                 685

Val Asn Arg Val Arg Gln Gly Tyr Ser Pro Leu Ser Phe Gln Thr Leu
        690                 695                 700

Leu Pro Ala Pro Arg Gly Pro Asp Arg Pro Glu Gly Ile Glu Glu
705                 710                 715                 720

Gly Gly Glu Gln Gly Arg Gly Arg Ser Ile Arg Leu Val Asn Gly Phe
                725                 730                 735

Ser Ala Leu Ile Trp Asp Asp Leu Arg Asn Leu Cys Leu Phe Ser Tyr
            740                 745                 750

His Arg Leu Arg Asp Leu Ile Leu Ile Ala Ala Arg Ile Val Glu Leu
        755                 760                 765

Leu Gly Arg Arg Gly Trp Glu Ala Leu Lys Tyr Leu Trp Asn Leu Leu
    770                 775                 780

Gln Tyr Trp Ile Gln Glu Leu Lys Asn Ser Ala Ile Ser Leu Phe Asp
785                 790                 795                 800

Thr Thr Ala Ile Ala Val Ala Glu Gly Thr Asp Arg Val Ile Glu Ile
                805                 810                 815

Val Gln Arg Ala Cys Arg Ala Ile Leu Asn Ile Pro Thr Arg Ile Arg
            820                 825                 830

Gln Gly Leu Glu Arg Ala Leu Leu
        835                 840

<210> SEQ ID NO 28
<211> LENGTH: 832
<212> TYPE: PRT
<213> ORGANISM: Human immunodeficiency virus type 1

<400> SEQUENCE: 28

Met Arg Val Arg Gly Met Gln Arg Asn Trp Gln His Leu Gly Lys Trp
1               5                   10                  15

Gly Leu Leu Phe Leu Gly Ile Leu Ile Ile Cys Asn Ala Ala Glu Asn
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ser Tyr Glu Lys Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asp Met Trp Lys
                85                  90                  95

Asn Asn Met Val Glu Gln Met His Thr Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Val Asn Ala Thr Asn Asn Asp Thr Asn Asp Asn Lys
    130                 135                 140

Thr Gly Ala Ile Gln Asn Cys Ser Phe Asn Met Thr Thr Glu Val Arg
145                 150                 155                 160

Asp Lys Lys Leu Lys Val His Ala Leu Phe Tyr Lys Leu Asp Ile Val
                165                 170                 175
```

```
Pro Ile Ser Asn Asn Ser Lys Tyr Arg Leu Ile Asn Cys Asn Thr
            180                 185                 190

Ser Thr Ile Thr Gln Ala Cys Pro Lys Val Ser Trp Asp Pro Ile Pro
        195                 200                 205

Ile His Tyr Cys Ala Pro Ala Gly Tyr Ala Ile Leu Lys Cys Asn Asp
    210                 215                 220

Lys Arg Phe Asn Gly Thr Gly Pro Cys Lys Asn Val Ser Thr Val Gln
225                 230                 235                 240

Cys Thr His Gly Ile Lys Pro Val Val Ser Thr Gln Leu Leu Leu Asn
                245                 250                 255

Gly Ser Leu Ala Glu Glu Asp Ile Ile Ile Arg Ser Gln Asn Ile Ser
            260                 265                 270

Asp Asn Ala Lys Thr Ile Ile Val His Leu Asn Glu Ser Val Gln Ile
        275                 280                 285

Asn Cys Thr Arg Pro Asn Asn Asn Thr Arg Lys Ser Ile His Leu Gly
    290                 295                 300

Pro Gly Gln Ala Phe Tyr Ala Thr Gly Glu Ile Ile Gly Asp Ile Arg
305                 310                 315                 320

Lys Ala His Cys Asn Ile Ser Gly Thr Gln Trp Asn Lys Thr Leu Glu
                325                 330                 335

Gln Val Lys Ala Lys Leu Lys Ser His Phe Pro Asn Lys Thr Ile Lys
            340                 345                 350

Phe Asn Ser Ser Ser Gly Gly Asp Leu Glu Ile Thr Met His Ser Phe
        355                 360                 365

Asn Cys Arg Gly Glu Phe Phe Tyr Cys Asn Thr Ser Gly Leu Phe Asn
    370                 375                 380

Asp Thr Gly Ser Asn Gly Thr Ile Thr Leu Pro Cys Arg Ile Lys Gln
385                 390                 395                 400

Ile Val Asn Met Trp Gln Glu Val Gly Arg Ala Met Tyr Ala Ala Pro
                405                 410                 415

Ile Ala Gly Asn Ile Thr Cys Asn Ser Asn Ile Thr Gly Leu Leu Leu
            420                 425                 430

Thr Arg Asp Gly Gly Gln Asn Asn Thr Glu Thr Phe Arg Pro Gly Gly
        435                 440                 445

Gly Asn Met Lys Asp Asn Trp Arg Ser Glu Leu Tyr Lys Tyr Lys Val
    450                 455                 460

Val Glu Ile Glu Pro Leu Gly Val Ala Pro Thr Lys Ala Lys Arg Gln
465                 470                 475                 480

Val Val Lys Arg Glu Arg Arg Ala Val Gly Ile Gly Ala Val Phe Leu
                485                 490                 495

Gly Phe Leu Gly Ala Ala Gly Ser Thr Met Gly Ala Ala Ser Ile Thr
            500                 505                 510

Leu Thr Val Gln Ala Arg Gln Leu Leu Ser Gly Ile Val Gln Gln Gln
        515                 520                 525

Asn Asn Leu Leu Arg Ala Ile Glu Ala Gln Gln His Leu Leu Gln Leu
    530                 535                 540

Thr Val Trp Gly Ile Lys Gln Leu Gln Ala Arg Val Leu Ala Val Glu
545                 550                 555                 560

Arg Tyr Leu Lys Asp Gln Gln Leu Leu Gly Leu Trp Gly Cys Ser Gly
                565                 570                 575

Lys Leu Ile Cys Thr Thr Asn Val Pro Trp Asn Ser Ser Trp Ser Asn
            580                 585                 590

Lys Ser Gln Asp Glu Ile Trp Asn Asn Met Thr Trp Met Glu Trp Glu
```

```
            595                 600                 605
Lys Glu Ile Ser Asn Tyr Ser Asn Ile Ile Tyr Arg Leu Ile Glu Glu
            610                 615                 620
Ser Gln Asn Gln Gln Glu Lys Asn Glu Gln Glu Leu Leu Ala Leu Asp
625                 630                 635                 640
Lys Trp Ala Ser Leu Trp Asn Trp Phe Asp Ile Ser Asn Trp Leu Trp
                    645                 650                 655
Tyr Ile Lys Ile Phe Ile Met Ile Val Gly Gly Leu Ile Gly Leu Arg
                660                 665                 670
Ile Val Phe Ala Val Leu Ser Ile Val Asn Arg Val Arg Lys Gly Tyr
            675                 680                 685
Ser Pro Leu Ser Leu Gln Thr Leu Ile Pro Ser Pro Arg Glu Pro Asp
        690                 695                 700
Arg Pro Glu Gly Ile Glu Glu Gly Gly Gly Glu Gln Gly Lys Asp Arg
705                 710                 715                 720
Ser Val Arg Leu Val Asn Gly Phe Leu Ala Leu Val Trp Asp Asp Leu
                    725                 730                 735
Arg Asn Leu Cys Leu Phe Ser Tyr Arg His Leu Arg Asp Phe Ile Leu
                740                 745                 750
Ile Ala Ala Arg Ile Val Asp Arg Gly Leu Arg Arg Gly Trp Glu Ala
            755                 760                 765
Leu Lys Tyr Leu Gly Asn Leu Thr Gln Tyr Trp Ser Gln Glu Leu Lys
        770                 775                 780
Asn Ser Ala Ile Ser Leu Leu Asn Thr Thr Ala Ile Val Val Ala Glu
785                 790                 795                 800
Gly Thr Asp Arg Val Ile Glu Ala Leu Gln Arg Ala Gly Arg Ala Val
                    805                 810                 815
Leu Asn Ile Pro Arg Arg Ile Arg Gln Gly Leu Glu Arg Ala Leu Leu
                820                 825                 830

<210> SEQ ID NO 29
<211> LENGTH: 831
<212> TYPE: PRT
<213> ORGANISM: Human immunodeficiency virus type 1

<400> SEQUENCE: 29

Met Arg Val Arg Glu Met Gln Arg Asn Trp Gln His Leu Gly Lys Trp
1               5                   10                  15
Gly Leu Leu Phe Leu Gly Ile Leu Ile Ile Cys Asn Ala Ala Asp Asn
                20                  25                  30
Leu Trp Val Thr Val Tyr Tyr Gly Val Pro Val Trp Lys Glu Ala Thr
            35                  40                  45
Thr Thr Leu Phe Cys Ala Ser Asp Ala Lys Ala Tyr Glu Arg Glu Val
        50                  55                  60
His Asn Val Trp Ala Thr Tyr Ala Cys Val Pro Thr Asp Pro Ser Pro
65                  70                  75                  80
Gln Glu Leu Val Leu Gly Asn Val Thr Glu Asn Phe Asn Met Trp Lys
                85                  90                  95
Asn Asn Met Val Asp Gln Met His Glu Asp Ile Ile Ser Leu Trp Asp
                100                 105                 110
Gln Ser Leu Lys Pro Cys Val Lys Leu Thr Pro Leu Cys Val Thr Leu
            115                 120                 125
Asn Cys Thr Asp Val Asn Val Thr Ile Asn Thr Thr Asn Val Thr Leu
        130                 135                 140
```

-continued

```
Gly Glu Ile Lys Asn Cys Ser Phe Asn Ile Thr Thr Glu Ile Lys Asp
145                 150                 155                 160

Lys Lys Lys Lys Glu Tyr Ala Leu Phe Tyr Arg Leu Asp Val Val Pro
                165                 170                 175

Ile Asn Asn Ser Ile Val Tyr Arg Leu Ile Ser Cys Asn Thr Ser Thr
                180                 185                 190

Val Thr Gln Ala Cys Pro Lys Val Ser Phe Glu Pro Ile Pro Ile His
            195                 200                 205

Tyr Cys Ala Pro Ala Gly Phe Ala Ile Leu Lys Cys Asn Asp Lys Lys
        210                 215                 220

Phe Asn Gly Thr Gly Leu Cys Arg Asn Val Ser Thr Val Gln Cys Thr
225                 230                 235                 240

His Gly Ile Arg Pro Val Val Ser Thr Gln Leu Leu Leu Asn Gly Ser
                245                 250                 255

Leu Ala Glu Glu Asp Ile Ile Ile Arg Ser Glu Asn Ile Ser Asp Asn
            260                 265                 270

Thr Lys Thr Ile Ile Val Gln Phe Asn Arg Ser Val Glu Ile Asn Cys
        275                 280                 285

Thr Arg Pro Asn Asn Asn Thr Arg Lys Ser Ile Arg Ile Gly Pro Gly
290                 295                 300

Arg Ala Phe Tyr Ala Thr Gly Asp Ile Ile Gly Asp Ile Arg Lys Ala
305                 310                 315                 320

Tyr Cys Asn Ile Asn Arg Thr Leu Trp Asn Glu Thr Leu Lys Lys Val
                325                 330                 335

Ala Glu Glu Phe Lys Asn His Phe Asn Ile Thr Val Thr Phe Asn Pro
            340                 345                 350

Ser Ser Gly Gly Asp Leu Glu Ile Thr Thr His Ser Phe Asn Cys Arg
        355                 360                 365

Gly Glu Phe Phe Tyr Cys Asn Thr Ser Asp Leu Phe Asn Asn Thr Glu
        370                 375                 380

Val Asn Asn Thr Lys Thr Ile Thr Leu Pro Cys Arg Ile Arg Gln Phe
385                 390                 395                 400

Val Asn Met Trp Gln Arg Val Gly Arg Ala Met Tyr Ala Pro Pro Ile
                405                 410                 415

Ala Gly Gln Ile Gln Cys Asn Ser Asn Ile Thr Gly Leu Leu Leu Thr
            420                 425                 430

Arg Asp Gly Gly Lys Asn Gly Ser Glu Thr Leu Arg Pro Gly Gly Gly
        435                 440                 445

Asp Met Arg Asp Asn Trp Arg Ser Glu Leu Tyr Lys Tyr Lys Val Val
450                 455                 460

Lys Ile Glu Pro Leu Gly Val Ala Pro Thr Lys Ala Lys Arg Gln Val
465                 470                 475                 480

Val Gln Arg Glu Lys Arg Ala Val Gly Ile Gly Ala Val Leu Leu Gly
                485                 490                 495

Phe Leu Gly Ala Ala Gly Ser Thr Met Gly Ala Ala Ser Ile Thr Leu
            500                 505                 510

Thr Val Gln Ala Arg Gln Leu Leu Ser Gly Ile Val Gln Gln Gln Ser
        515                 520                 525

Asn Leu Leu Lys Ala Ile Glu Ala Gln Gln His Leu Leu Gln Leu Thr
        530                 535                 540

Val Trp Gly Ile Lys Gln Leu Gln Ala Arg Ile Leu Ala Val Glu Arg
545                 550                 555                 560

Tyr Leu Lys Asp Gln Gln Leu Leu Gly Ile Trp Gly Cys Ser Gly Lys
```

```
                    565                 570                 575
Leu Ile Cys Thr Thr Asn Val Pro Trp Asn Ser Ser Trp Ser Asn Lys
            580                 585                 590

Ser Gln Asp Glu Ile Trp Asp Asn Met Thr Trp Met Gln Trp Glu Lys
        595                 600                 605

Glu Ile Ser Asn Tyr Thr Asp Thr Ile Tyr Arg Leu Ile Glu Asp Ala
    610                 615                 620

Gln Asn Gln Gln Glu Lys Asn Glu Gln Asp Leu Leu Ala Leu Asp Lys
625                 630                 635                 640

Trp Asp Asn Leu Trp Ser Trp Phe Thr Ile Thr Asn Trp Leu Trp Tyr
                645                 650                 655

Ile Lys Ile Phe Ile Met Ile Val Gly Gly Leu Ile Gly Leu Arg Ile
            660                 665                 670

Val Phe Ala Val Leu Ser Val Val Asn Arg Val Arg Gln Gly Tyr Ser
        675                 680                 685

Pro Leu Ser Leu Gln Thr Leu Ile Pro Asn Pro Arg Gly Pro Glu Arg
    690                 695                 700

Pro Gly Gly Ile Glu Glu Gly Gly Glu Gln Asp Arg Asp Arg Ser
705                 710                 715                 720

Ile Arg Leu Val Ser Gly Phe Leu Ala Leu Ala Trp Asp Asp Leu Arg
                725                 730                 735

Ser Leu Cys Leu Phe Ser Tyr Arg His Leu Arg Asp Phe Ile Leu Ile
            740                 745                 750

Ala Ala Arg Thr Val Asp Met Gly Leu Lys Arg Gly Trp Glu Ala Leu
        755                 760                 765

Lys Tyr Leu Trp Asn Leu Pro Gln Tyr Trp Gly Gln Glu Leu Lys Asn
    770                 775                 780

Ser Ala Ile Ser Leu Leu Asp Thr Thr Ala Ile Ala Val Ala Glu Gly
785                 790                 795                 800

Thr Asp Arg Ile Ile Glu Val Leu Gln Arg Ala Gly Arg Ala Val Leu
                805                 810                 815

His Ile Pro Arg Arg Ile Arg Gln Gly Phe Glu Arg Ala Leu Leu
            820                 825                 830

<210> SEQ ID NO 30
<211> LENGTH: 370
<212> TYPE: PRT
<213> ORGANISM: Homo sapiens

<400> SEQUENCE: 30

Met Val Gly Lys Leu Lys Gln Asn Leu Leu Leu Ala Cys Leu Val Ile
1               5                   10                  15

Ser Ser Val Thr Val Phe Tyr Leu Gly Gln His Ala Met Glu Cys His
            20                  25                  30

His Arg Ile Glu Glu Arg Ser Gln Pro Val Lys Leu Glu Ser Thr Arg
        35                  40                  45

Thr Thr Val Arg Thr Gly Leu Asp Leu Lys Ala Asn Lys Thr Phe Ala
    50                  55                  60

Tyr His Lys Asp Met Pro Leu Ile Phe Ile Gly Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
            100                 105                 110
```

Met Trp Ser Arg Ser Ser Lys Glu Lys Ile Arg Leu Asp Glu Ala Gly
            115                 120                 125

Val Thr Asp Glu Val Leu Asp Ser Ala Met Gln Ala Phe Leu Leu Glu
        130                 135                 140

Ile Ile Val Lys His Gly Glu Pro Ala Pro Tyr Leu Cys Asn Lys Asp
145                 150                 155                 160

Pro Phe Ala Leu Lys Ser Leu Thr Tyr Leu Ser Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
        195                 200                 205

Arg Asp Cys Leu Thr Lys Trp Asn Arg Ala Ile Glu Thr Met Tyr Asn
210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu Gln Ile Pro Trp Asn His Ser Val Leu His His Glu Glu Met Ile
            260                 265                 270

Gly Lys Ala Gly Gly Val Ser Leu Ser Lys Val Glu Arg Ser Thr Asp
        275                 280                 285

Gln Val Ile Lys Pro Val Asn Val Gly Ala Leu Ser Lys Trp Val Gly
        290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Pro Asn Tyr Gly
                325                 330                 335

Lys Pro Asp Pro Lys Ile Ile Glu Asn Thr Arg Arg Val Tyr Lys Gly
            340                 345                 350

Glu Phe Gln Leu Pro Asp Phe Leu Lys Glu Lys Pro Gln Thr Glu Gln
        355                 360                 365

Val Glu
    370

<210> SEQ ID NO 31
<211> LENGTH: 2062
<212> TYPE: DNA
<213> ORGANISM: Homo sapiens

<400> SEQUENCE: 31
agatgtgtga tcccgccacc tccccggacc ctggcggttg tcgctgagtt ggcgaccgcg      60
ggagacgctg ctgaggcggc ttcggttgcg ggtcggaacg gcgctgctct gcggggccgg     120
tccaggctgg cagctgccgg cgcttggcgg tgagggcggg ctcccgagtg gcccccacc      180 gaaggcggtg ggaccagcgg ctgaggccag gatgccgtcc aggcggcgcg gcggctcctc     240
actcatccca gatgttggtt atctttctga gtagactgt ccatggcctg aacattttcc      300
gaaaatcatt ttgagcaaaa tatctgttta ataacaagat aaccacatca agatggttgg     360
aaagctgaag cagaacttac tattggcatg tctggtgatt agttctgtga ctgtgtttta     420
cctgggccag catgccatgg aatgccatca ccggatagag aacgtagcc agccagtcaa      480 attggagagc acaaggacca ctgtgagaac tggcctggac ctcaaagcca acaaaacctt     540
tgcctatcac aaagatatgc ctttaatatt tattggaggt gtgcctcgga gtggaaccac     600

```
actcatgagg gccatgctgg acgcacatcc tgacattcgc tgtggagagg aaaccagggt    660
cattccccga atcctggccc tgaagcagat gtggtcacgg tcaagtaaag agaagatccg    720
cctggatgag gctggtgtta ctgatgaagt gctggattct gccatgcaag ccttcttact    780
agaaattatc gttaagcatg gggagccagc cccttattta tgtaataaag atcctttgc     840
cctgaaatct ttaacttacc tttctaggtt attccccaat gccaaatttc tcctgatggt    900
ccgagatggc cgggcatcag tacattcaat gatttctcga aaagttacta tagctggatt    960
tgatctgaac agctataggg actgtttgac aaagtggaat cgtgctatag agaccatgta    1020
taaccagtgt atggaggttg gttataaaaa gtgcatgttg gttcactatg aacaacttgt    1080
cttacatcct gaacggtgga tgagaacact cttaaagttc ctccagattc catggaacca    1140
ctcagtattg caccatgaag agatgattgg gaaagctggg ggagtgtctc tgtcaaaagt    1200
ggagagatct acagaccaag taatcaagcc agtcaatgta ggagctctat caaaatgggt    1260
tgggaagata ccgccagatg ttttacaaga catggcagtg attgctccta tgcttgccaa    1320
gcttggatat gacccatatg ccaacccacc taactacgga aaacctgatc ccaaaattat    1380
tgaaaacact cgaagggtct ataagggaga attccaacta cctgactttc ttaaagaaaa    1440
accacagact gagcaagtgg agtagcagaa ccaggagcct cttccataca tgaggaagaa    1500
ttgctgcctt tcagcagaa gggaaattcc taggattggc tgtcccctgc caagcttggt     1560
ggagcgtctg caccttggct cgccgcctg tgcatttgcc agtttcctcc cactgagagg     1620
atggaggtgt ccgcacagct ttgggcctcg tgagggatct gcctcctgag caaagagctc    1680
ttgatcccga tttcatgcac agccctgcag taaggagccc agaaggaaca tgtgtttcct    1740
gttaaaactc ctcttgttct cttttcttac attatgacgt tgttttcaa ggagagggtt     1800
taaaaatggg atcctgtaag cagacttggg cagtctcctt ttgaaatagg ttgtctgtac    1860
atgttctaat gttttgtaga acacgtgtgc ctgtttaagt gtattgatgt gaataatatt    1920
aaatatccta attatttaat tcattgtatt gtttctgaga agttgggaaa ttaccattat    1980
acatttacaa cctaatgact tttgtatttt attttcaaa ataaaagctt tcaatgtgaa     2040
gcattctggt aaaaaaaaaa aa                                              2062
```

<210> SEQ ID NO 32
<211> LENGTH: 370
<212> TYPE: PRT
<213> ORGANISM: Mus musculus

<400> SEQUENCE: 32

```
Met Val Gly Lys Leu Lys Gln Asn Leu Leu Ala Cys Leu Val Ile
1               5                   10                  15

Ser Ser Val Thr Val Phe Tyr Leu Gly Gln His Ala Met Glu Cys His
                20                  25                  30

His Arg Ile Glu Glu Arg Ser Gln Pro Ala Arg Leu Glu Asn Pro Lys
        35                  40                  45

Ala Thr Val Arg Ala Gly Leu Asp Ile Lys Ala Asn Lys Thr Phe Thr
    50                  55                  60

Tyr His Lys Asp Met Pro Leu Ile Phe Ile Gly Gly Val Pro Arg Ser
65                  70                  75                  80

Gly Thr Thr Leu Met Arg Ala Met Leu Asp Ala His Pro Asp Ile Arg
                85                  90                  95

Cys Gly Glu Glu Thr Arg Val Ile Pro Arg Ile Leu Ala Leu Lys Gln
            100                 105                 110
```

```
Met Trp Ser Arg Ser Ser Lys Glu Lys Ile Arg Leu Asp Glu Ala Gly
            115                 120                 125

Val Thr Asp Glu Val Leu Asp Ser Ala Met Gln Ala Phe Leu Leu Glu
    130                 135                 140

Val Ile Val Lys His Gly Glu Pro Ala Pro Tyr Leu Cys Asn Lys Asp
145                 150                 155                 160

Pro Phe Ala Leu Lys Ser Leu Thr Tyr Leu Ala Arg Leu Phe Pro Asn
                165                 170                 175

Ala Lys Phe Leu Leu Met Val Arg Asp Gly Arg Ala Ser Val His Ser
            180                 185                 190

Met Ile Ser Arg Lys Val Thr Ile Ala Gly Phe Asp Leu Asn Ser Tyr
        195                 200                 205

Arg Asp Cys Leu Thr Lys Trp Asn Arg Ala Ile Glu Thr Met Tyr Asn
    210                 215                 220

Gln Cys Met Glu Val Gly Tyr Lys Lys Cys Met Leu Val His Tyr Glu
225                 230                 235                 240

Gln Leu Val Leu His Pro Glu Arg Trp Met Arg Thr Leu Leu Lys Phe
                245                 250                 255

Leu His Ile Pro Trp Asn His Ser Val Leu His His Glu Glu Met Ile
            260                 265                 270

Gly Lys Ala Gly Gly Val Ser Leu Ser Lys Val Glu Arg Ser Thr Asp
        275                 280                 285

Gln Val Ile Lys Pro Val Asn Val Gly Ala Leu Ser Lys Trp Val Gly
    290                 295                 300

Lys Ile Pro Pro Asp Val Leu Gln Asp Met Ala Val Ile Ala Pro Met
305                 310                 315                 320

Leu Ala Lys Leu Gly Tyr Asp Pro Tyr Ala Asn Pro Asn Tyr Gly
                325                 330                 335

Lys Pro Asp Pro Lys Ile Leu Glu Asn Thr Arg Arg Val Tyr Lys Gly
            340                 345                 350

Glu Phe Gln Leu Pro Asp Phe Leu Lys Glu Lys Pro Gln Thr Glu Gln
        355                 360                 365

Val Glu
    370

<210> SEQ ID NO 33
<211> LENGTH: 2054
<212> TYPE: DNA
<213> ORGANISM: Mus musculus

<400> SEQUENCE: 33
aaatcagaga ggcggacaca tcgcgcggcc cggctgcggg tagcctatgg cggcgtgcgt    60
gagatcccgc ggccacgcgg cggcgggagg caggagctga ggcggcgacc gcggccagtc   120
gctgctgagg cggccgcggg tgcgcttctc ggcggggccg ggcagggccg tcgcctggcg   180
gtgaggacgc gctcccgggg cgggcgctat ggccaccaac tagggcggcc ggagaagcgg   240
ccgaagccca agatgccgga gcgacggcac ggctgcgcct ccgccatcgt aggtgccgat   300
ccccttgcca cagtcgagtc tccatggcct gaccgtgtct tgacaataat tttgagcaaa   360
atctatgtct aataagaaga taaccacatc aagatggttg ggaagctgaa gcagaactta   420
ctcttggcgt gtctggtgat tagttctgtg accgtgtttt acctgggcca gcatgccatg   480
gagtgccatc accgaataga ggaacgtagc cagccagccc gactgcagaa ccccaaggcg   540
actgtgcgag ctggcctcga catcaaagcc aacaaaacat tcacctatca caaagatatg   600
```

```
cctttaatat tcatcggggg tgtgcctcgg agcggcacca cactcatgag ggctatgctg    660
gacgcacatc ctgacatccg ctgtggagag gaaaccaggg tcatccctcg aatcctggcc    720
ctgaagcaga tgtggtcccg gtccagtaaa gagaagatcc gcttggatga ggcgggtgtc    780
acagatgaag tgctagattc tgccatgcaa gccttccttc tggaggtcat tgttaaacat    840
ggggagccgg cacttatttt atgtaacaaa gatccgtttg ccctgaaatc cttgacttac    900
cttgctaggt tatttcccaa tgccaaattt ctcctgatgg tccgagatgg ccgggcgtca    960
gtacattcaa tgatttctcg gaaagttact atagctggct ttgacctgaa cagctaccgg   1020
gactgtctga ccaagtggaa ccgggccata gaaaccatgt acaaccagtg tatggaagtt   1080
ggttataaga aatgcatgtt ggttcactat gaacagctcg tcttacaccc tgaacggtgg   1140
atgagaacgc tcttaaagtt cctccatatt ccatggaacc attccgtttt gcaccatgaa   1200
gaaatgatcg ggaaagctgg gggagtttct ctgtcaaagg tggaaagatc aacagaccaa   1260
gtcatcaaac ccgtcaacgt gggggcgcta tcgaagtggg ttgggaagat accccggac   1320
gtcttacaag acatggccgt gattgcaccc atgctcgcca agcttggata tgacccatac   1380
gccaatcctc ctaactacgg aaaacctgac cccaagatcc ttgaaaacac caggagggtc   1440
tataaaggag aatttcagct ccctgacttt ctgaaagaaa acccccagac ggagcaagtg   1500
gagtaactga gcccgtaact tcccacaggg acgactgctg ccttgtctac agaagggaaa   1560
tctcgggaac ggctgtctgc tgcgacaagg agtgtctgtg cccatcgctc ctgttcacct   1620
gccagcctcc tgtccccagg gggggtgtca cacacccggg cctccccaag tgatggctct   1680
tgagcccagg aacatgcatg gccctcagga tgaggagccc agcagggaca cagttctgtc   1740
acagctcctc ttgtccttgt ctttccttcc caggttccag tctttaattt caaggaaagg   1800
agagtttgaa gttggcattc tgttaacaaa atcaggcagt ctcattccga ataggttcta   1860
tgtacacgtt ccgatgtttt gtagaacact cgtgcctgtt gaaacgtatc gatgtggata   1920
atagtaaata ccttaattat ttaaataatt cattgtattg tttcagagac gtttggaaat   1980
tactgtatac atttacaacc taatgacttt tgtatttat ttttcaaaat aaaagcttaa   2040
atgtgaagca ctca                                                    2054
```

<210> SEQ ID NO 34
<211> LENGTH: 377
<212> TYPE: PRT
<213> ORGANISM: Homo sapiens

<400> SEQUENCE: 34

```
Met Arg Leu Ser Val Arg Arg Val Leu Leu Ala Ala Gly Cys Ala Leu
1               5                   10                  15

Val Leu Val Leu Ala Val Gln Leu Gly Gln Gln Val Leu Glu Cys Arg
            20                  25                  30

Ala Val Leu Ala Gly Leu Arg Ser Pro Arg Gly Ala Met Arg Pro Glu
        35                  40                  45

Gln Glu Glu Leu Val Met Val Gly Thr Asn His Val Glu Tyr Arg Tyr
    50                  55                  60

Gly Lys Ala Met Pro Leu Ile Phe Val Gly Val Pro Arg Ser Gly
65                  70                  75                  80

Thr Thr Leu Met Arg Ala Met Leu Asp Ala His Pro Glu Val Arg Cys
                85                  90                  95

Gly Glu Glu Thr Arg Ile Ile Pro Arg Val Leu Ala Met Arg Gln Ala
            100                 105                 110
```

Trp Ser Lys Ser Gly Arg Glu Lys Leu Arg Leu Asp Glu Ala Gly Val
            115                 120                 125

Thr Asp Glu Val Leu Asp Ala Ala Met Gln Ala Phe Ile Leu Glu Val
        130                 135                 140

Ile Ala Lys His Gly Glu Pro Ala Arg Val Leu Cys Asn Lys Asp Pro
145                 150                 155                 160

Phe Thr Leu Lys Ser Ser Val Tyr Leu Ser Arg Leu Phe Pro Asn Ser
                165                 170                 175

Lys Phe Leu Leu Met Val Arg Asp Gly Arg Ala Ser Val His Ser Met
            180                 185                 190

Ile Thr Arg Lys Val Thr Ile Ala Gly Phe Asp Leu Ser Ser Tyr Arg
        195                 200                 205

Asp Cys Leu Thr Lys Trp Asn Lys Ala Ile Glu Val Met Tyr Ala Gln
210                 215                 220

Cys Met Glu Val Gly Lys Glu Lys Cys Leu Pro Val Tyr Tyr Glu Gln
225                 230                 235                 240

Leu Val Leu His Pro Arg Arg Ser Leu Lys Leu Ile Leu Asp Phe Leu
                245                 250                 255

Gly Ile Ala Trp Ser Asp Ala Val Leu His His Glu Asp Leu Ile Gly
            260                 265                 270

Lys Pro Gly Gly Val Ser Leu Ser Lys Ile Glu Arg Ser Thr Asp Gln
        275                 280                 285

Val Ile Lys Pro Val Asn Leu Glu Ala Leu Ser Lys Trp Thr Gly His
    290                 295                 300

Ile Pro Gly Asp Val Val Arg Asp Met Ala Gln Ile Ala Pro Met Leu
305                 310                 315                 320

Ala Gln Leu Gly Tyr Asp Pro Tyr Ala Asn Pro Asn Tyr Gly Asn
                325                 330                 335

Pro Asp Pro Phe Val Ile Asn Asn Thr Gln Arg Val Leu Lys Gly Asp
            340                 345                 350

Tyr Lys Thr Pro Ala Asn Leu Lys Gly Tyr Phe Gln Val Asn Gln Asn
        355                 360                 365

Ser Thr Ser Ser His Leu Gly Ser Ser
    370                 375

<210> SEQ ID NO 35
<211> LENGTH: 2018
<212> TYPE: DNA
<213> ORGANISM: Homo sapiens

<400> SEQUENCE: 35
gagaggcagg cccatcgcaa ggctgactga tccttcaaag gagcctccca gctaaaagcc      60
agcaggagag agaccttggc caccaagggt ctgccagctc tggtggtcc ccactccagc      120 cacctgccag ctcgagcctg accctcgcct ccaccctggc tgctgcctgt accgctctca     180
gggctctgcc agcagacagc cttggcacac aggcacaagg gctggagccc agagatgaga    240
gtgcccaagg gagatgtgag cctggcgggc tgcccgctaa cctgtcgctg aagccccaga    300
agcgggccct caggccaggc ctaccctgcc tccggcccag catgcgcctg tcggtgcgga    360
gggtgctgct ggcagccggc tgcgcccctgg tcctggtgct ggcggttcag ctgggacagc    420
aggtgctaga gtgccgggcg gtgctggcgg gcctgcggag ccccggggg gccatgcggc     480 ctgagcagga ggagctggtg atggtgggca ccaaccacgt ggaataccgc tatggcaagg    540
ccatgccgct catcttcgtg ggtggcgtgc ctcgcagtgg caccacgttg atgcgcgcca    600

```
tgctggacgc gcaccccgag gtgcgctgcg gcgaggagac ccgcatcatc ccgcgcgtgc    660
tggccatgcg ccaggcctgg tccaagtctg gccgtgagaa gctgcggctg gatgaggcgg    720
gggtgacgga tgaggtgctg gacgccgcca tgcaggcctt catcctggag gtgattgcca    780
agcacggaga gccggcccgc gtgctctgca caaggaccc  atttacgctc aagtcctcgg    840
tctacctgtc gcgcctgttc cccaactcca agttcctgct gatggtgcgg gacggccggg    900
cctccgtgca ctccatgatc acgcgcaaag tcaccattgc gggctttgac ctcagcagct    960
accgtgactg cctcaccaag tggaacaagg ccatcgaggt gatgtacgcc cagtgcatgg   1020
aggtaggcaa ggagaagtgc ctgcctgtgt actacgagca gctggtgctg cacccccagg   1080
gctcactcaa gctcatcctc gacttcctcg gcatcgcctg gagcgacgct gtcctccacc   1140
atgaagacct cattggcaag cccggtggtg tctccctgtc caagatcgag cggtccacgg   1200
accaggtcat caagcctgtt aacctggaag cgctctccaa gtggactggc cacatccctg   1260
gggatgtggt gcgggacatg gcccagatcg cccccatgct ggctcagctc ggctatgacc   1320
cttatgcaaa ccccccaac  tatggcaacc ctgaccccett cgtcatcaac aacacacagc   1380
gggtcttgaa aggggactat aaaacaccag ccaatctgaa aggatatttt caggtgaacc   1440
agaacagcac ctcctcccac ttaggaagct cgtgatttcc agatctccgc aaatgacttc   1500
attgccaaga agaagaaa atgcatttaa gtggaaatcg dacctctaat ccaagcatat   1560
tgcttgctat taatcgccaa acaggactg ctgatgagga atgtatttgc atatgtttgc   1620
aaaagctgaa tcattgaaaa cgtaccttga aactctctat ctctggacac tccagggtag   1680
agaatgaagg gtatggaagt agtccggctt ttgaaactta ggtattttat atttttcccc   1740
tcaagaactt tttttaaga gacagatttg ccatcctcct taatttgcag gactgccttg   1800
gtggctttgt ttgctgggac aaggcccaca acctgtgcct ctcctattga cccttacttt   1860
gaattcaaag aatctatta agagtttaat atatgaggct ttctttgatt cctcctcagt   1920
tctacctagt ttcacagagg aaaaaaatac tctttgaata aagtgaacag aggctcattt   1980
gtttgtgcct tactttactg aaaaaaaaa aaaaaaa                              2018
```

<210> SEQ ID NO 36
<211> LENGTH: 377
<212> TYPE: PRT
<213> ORGANISM: Homo sapiens

<400> SEQUENCE: 36

```
Met Arg Leu Ser Val Arg Arg Val Leu Leu Ala Ala Gly Cys Ala Leu
1               5                   10                  15

Val Leu Val Leu Ala Val Gln Leu Gly Gln Gln Val Leu Glu Cys Arg
            20                  25                  30

Ala Val Leu Ala Gly Leu Arg Ser Pro Arg Gly Ala Met Arg Pro Glu
        35                  40                  45

Gln Glu Glu Leu Val Met Val Gly Thr Asn His Val Glu Tyr Arg Tyr
    50                  55                  60

Gly Lys Ala Met Pro Leu Ile Phe Val Gly Val Pro Arg Ser Gly
65                  70                  75                  80

Thr Thr Leu Met Arg Ala Met Leu Asp Ala His Pro Glu Val Arg Cys
                85                  90                  95

Gly Glu Glu Thr Arg Ile Ile Pro Arg Val Leu Ala Met Arg Gln Ala
            100                 105                 110

Trp Ser Lys Ser Gly Arg Glu Lys Leu Arg Leu Asp Glu Ala Gly Val
        115                 120                 125
```

```
Thr Asp Glu Val Leu Asp Ala Ala Met Gln Ala Phe Ile Leu Glu Val
    130                 135                 140
Ile Ala Lys His Gly Glu Pro Ala Arg Val Leu Cys Asn Lys Asp Pro
145                 150                 155                 160
Phe Thr Leu Lys Ser Ser Val Tyr Leu Ser Arg Leu Phe Pro Asn Ser
                165                 170                 175
Lys Phe Leu Leu Met Val Arg Asp Gly Arg Ala Ser Val His Ser Met
                180                 185                 190
Ile Thr Arg Lys Val Thr Ile Ala Gly Phe Asp Leu Ser Ser Tyr Arg
                195                 200                 205
Asp Cys Leu Thr Lys Trp Asn Lys Ala Ile Glu Val Met Tyr Ala Gln
    210                 215                 220
Cys Met Glu Val Gly Lys Glu Lys Cys Leu Pro Val Tyr Tyr Glu Gln
225                 230                 235                 240
Leu Val Leu His Pro Arg Arg Ser Leu Lys Leu Ile Leu Asp Phe Leu
                245                 250                 255
Gly Ile Ala Trp Ser Asp Ala Val Leu His His Glu Asp Leu Ile Gly
                260                 265                 270
Lys Pro Gly Gly Val Ser Leu Ser Lys Ile Glu Arg Ser Thr Asp Gln
                275                 280                 285
Val Ile Lys Pro Val Asn Leu Glu Ala Leu Ser Lys Trp Thr Gly His
    290                 295                 300
Ile Pro Gly Asp Val Val Arg Asp Met Ala Gln Ile Ala Pro Met Leu
305                 310                 315                 320
Ala Gln Leu Gly Tyr Asp Pro Tyr Ala Asn Pro Asn Tyr Gly Asn
                325                 330                 335
Pro Asp Pro Phe Val Ile Asn Asn Thr Gln Arg Val Leu Lys Gly Asp
                340                 345                 350
Tyr Lys Thr Pro Ala Asn Leu Lys Gly Tyr Phe Gln Val Asn Gln Asn
                355                 360                 365
Ser Thr Ser Ser His Leu Gly Ser Ser
    370                 375

<210> SEQ ID NO 37
<211> LENGTH: 1910
<212> TYPE: DNA
<213> ORGANISM: Homo sapiens

<400> SEQUENCE: 37
cttccccggc tggggcggct ggagagccgg gagtcgctgg gtgcgtgggg ctgcctcgcc    60
gcgtctcgcc acgggctctg ccagcagaca gccttggcac acaggcacaa gggctggagc   120
ccagagatga gagtgcccaa gggagatgtg agcctggcgg gctgcccgct aacctgtcgc   180
tgaagcccca gaagcgggcc ctcaggccag gcctaccctg cctccggccc agcatgcgcc   240
tgtcggtgcg gagggtgctg ctggcagccg gctgcgccct ggtcctggtg ctggcggttc   300
agctgggaca gcaggtgcta gagtgccggg cggtgctggc gggcctgcgg agccccgggt   360
gggccatgcg gcctgagcag gaggagctgg tgatggtggg caccaaccac gtggaatacc   420
gctatggcaa ggccatgccg ctcatcttcg tgggtggcgt gcctcgcagt ggcaccacgt   480
tgatgcgcgc catgctggac gcgcaccccg aggtgcgctg cggcgaggag acccgcatca   540
tcccgcgcgt gctggccatg cgccaggcct ggtccaagtc tggccgtgag aagctgcggc   600
tggatgaggc gggggtgacg gatgaggtgc tggacgccgc catgcaggcc ttcatcctgg   660
```

```
aggtgattgc caagcacgga gagccggccc gcgtgctctg caacaaggac ccatttacgc    720
tcaagtcctc ggtctacctg tcgcgcctgt tccccaactc caagttcctg ctgatggtgc    780
gggacggccg ggcctccgtg cactccatga tcacgcgcaa agtcaccatt gcgggctttg    840
acctcagcag ctaccgtgac tgcctcacca gtggaacaa ggccatcgag gtgatgtacg     900
cccagtgcat ggaggtaggc aaggagaagt gcctgcctgt gtactacgag cagctggtgc    960
tgcaccccag cgctcactc aagctcatcc tcgacttcct cggcatcgcc tggagcgacg    1020
ctgtcctcca ccatgaagac ctcattggca agcccggtgg tgtctccctg tccaagatcg   1080
agcggtccac ggaccaggtc atcaagcctg ttaacctgga agcgctctcc aagtggactg   1140
gccacatccc tggggatgtg gtgcgggaca tggcccagat cgcccccatg ctggctcagc   1200
tcggctatga cccttatgca accccccca actatggcaa ccctgacccc ttcgtcatca    1260
acaacacaca gcgggtcttg aaaggggact ataaaacacc agccaatctg aaaggatatt   1320
ttcaggtgaa ccagaacagc acctcctccc acttaggaag ctcgtgattt ccagatctcc   1380
gcaaatgact tcattgccaa gaagagaaga aaatgcattt aagtggaaat cggacctcta   1440
atccaagcat attgcttgct attaatcgcc aaaacaggac tgctgatgag gaatgtattt   1500
gcatatgttt gcaaaagctg aatcattgaa acgtaccttt gaaactctct atctctggac   1560
actccagggt agagaatgaa gggtatggaa gtagtccggc ttttgaaact taggtatttt   1620
atatttttcc cctcaagaac ttttttttaa gagacagatt tgccatcctc cttaatttgc   1680
aggactgcct tggtggcttt gtttgctggg acaaggccca caacctgtgc ctctcctatt   1740
gaccccttact ttgaattcaa agaatctatt taagagttta atatatgagg ctttctttga   1800
ttcctcctca gttctaccta gtttcacaga ggaaaaaaat actctttgaa taaagtgaac   1860
agaggctcat tgtttgtgc cttactttac tgaaaaaaaa aaaaaaaaaa              1910
```

<210> SEQ ID NO 38
<211> LENGTH: 390
<212> TYPE: PRT
<213> ORGANISM: Mus musculus

<400> SEQUENCE: 38

Met Arg Arg Ala Pro Trp Leu Gly Leu Arg Pro Trp Leu Gly Met Arg
1               5                   10                  15

Leu Ser Val Arg Lys Val Leu Leu Ala Ala Gly Cys Ala Leu Ala Leu
            20                  25                  30

Val Leu Ala Val Gln Leu Gly Gln Gln Val Leu Glu Cys Arg Ala Val
        35                  40                  45

Leu Gly Gly Thr Arg Asn Pro Arg Arg Met Arg Pro Glu Gln Glu Glu
    50                  55                  60

Leu Val Met Leu Gly Ala Asp His Val Glu Tyr Arg Tyr Gly Lys Ala
65                  70                  75                  80

Met Pro Leu Ile Phe Val Gly Val Pro Arg Ser Gly Thr Thr Leu
                85                  90                  95

Met Arg Ala Met Leu Asp Ala His Pro Glu Val Arg Cys Gly Glu Glu
            100                 105                 110

Thr Arg Ile Ile Pro Arg Val Leu Ala Met Arg Gln Ala Trp Thr Lys
        115                 120                 125

Ser Gly Arg Glu Lys Leu Arg Leu Asp Glu Ala Gly Val Thr Asp Glu
    130                 135                 140

Val Leu Asp Ala Ala Met Gln Ala Phe Ile Leu Glu Val Ile Ala Lys
145                 150                 155                 160

His Gly Glu Pro Ala Arg Val Leu Cys Asn Lys Asp Pro Phe Thr Leu
            165                 170                 175

Lys Ser Ser Val Tyr Leu Ala Arg Leu Phe Pro Asn Ser Lys Phe Leu
        180                 185                 190

Leu Met Val Arg Asp Gly Arg Ala Ser Val His Ser Met Ile Thr Arg
            195                 200                 205

Lys Val Thr Ile Ala Gly Phe Asp Leu Ser Ser Tyr Arg Asp Cys Leu
        210                 215                 220

Thr Lys Trp Asn Lys Ala Ile Glu Val Met Tyr Ala Gln Cys Met Glu
225                 230                 235                 240

Val Gly Arg Asp Lys Cys Leu Pro Val Tyr Tyr Glu Gln Leu Val Leu
                245                 250                 255

His Pro Arg Arg Ser Leu Lys Arg Ile Leu Asp Phe Leu Gly Ile Ala
            260                 265                 270

Trp Ser Asp Thr Val Leu His His Glu Asp Leu Ile Gly Lys Pro Gly
        275                 280                 285

Gly Val Ser Leu Ser Lys Ile Glu Arg Ser Thr Asp Gln Val Ile Lys
        290                 295                 300

Pro Val Asn Leu Glu Ala Leu Ser Lys Trp Thr Gly His Ile Pro Arg
305                 310                 315                 320

Asp Val Val Arg Asp Met Ala Gln Ile Ala Pro Met Leu Ala Arg Leu
                325                 330                 335

Gly Tyr Asp Pro Tyr Ala Asn Pro Pro Asn Tyr Gly Asn Pro Asp Pro
            340                 345                 350

Ile Val Ile Asn Asn Thr His Arg Val Leu Lys Gly Asp Tyr Lys Thr
        355                 360                 365

Pro Ala Asn Leu Lys Gly Tyr Phe Gln Val Asn Gln Asn Ser Thr Ser
    370                 375                 380

Pro His Leu Gly Ser Ser
385                 390

<210> SEQ ID NO 39
<211> LENGTH: 1830
<212> TYPE: DNA
<213> ORGANISM: Mus musculus

<400> SEQUENCE: 39
cctcgcggcg cctccctggc ggccggcagg gagccggagt ctgcgcgggc gccgatttgg      60
gcacggactg tcagggcagg aagccgtggt gaccaggctc gaggactggt gcttgaaaat     120
gagggcgccc aggggagatg tataccaggt gggcctgctg acccgtccat gaggcgggcc     180
ccctggctgg gcctgcgacc ctggctgggc atgcgcctgt cggtgcgtaa ggtgctgctg     240
gccgccggct gtgctctggc cctggtgctc gctgtgcagc ttgggcagca agtactggag     300
tgccgggcgg tgctcggggg cacacggaac ccacggagga tgcggccgga gcaggaggaa     360
ctggtgatgc tcggcgccga ccacgtggag taccgctatg caaggccat gccactcatc      420 tttgtgggcg gcgtgccacg cagtggcacc acgctcatgc gcgccatgtt ggacgcacac     480
ccagaggtgc gctgtgggga ggagacgcgc atcatccctc gtgtgctggc catgcggcag     540
gcctggacca agtctggccg tgagaagctg cggctggacg aggcaggtgt gacggatgag     600
gtgctggacg cggccatgca ggccttcatt ctggaggtga tcgccaagca cggcgaacca     660
gcccgcgtgc tgtgtaacaa ggacccttc acactcaagt catccgtcta cctggcacgc      720
ctgttcccca actccaaatt cctgctaatg gtgcgtgacg gccgggcgtc cgtgcactcc     780

```
atgatcacgc gcaaggtcac catcgcgggc tttgacctca gcagctaccg agactgcctc    840
accaagtgga acaaggccat cgaggtgatg tacgcacagt gcatggaggt gggcagggac    900
aagtgcctgc ccgtgtacta tgagcagttg gtgctgcacc cccggcgctc actcaaacgc    960
atcctggact tcctgggcat cgcctggagt gacacagtcc tgcaccacga ggacctcatt   1020
ggcaagcctg ggggcgtctc cttgtccaag atcgagcggt ccacggacca ggtcatcaaa   1080
ccggtgaact tggaagctct ctccaagtgg acgggccaca tccctagaga cgtggtgagg   1140
gatatggccc agattgcccc catgctggcc cggcttggct atgacccgta tgcgaatcca   1200
cccaactatg gaaccccga ccccattgtc atcaacaaca cacaccgggt cttgaaagga   1260
gactataaaa cgccagccaa tctgaaagga tattttcagg tgaaccagaa cagcacctcc   1320
ccacacctag gaagttcgtg atttccagtc cctgcagggc tcagacgcct cagtcctcga   1380
cctgcacacg gaagctggac taacccaagc acatggcttg ctctcagtca cgccgggcgg   1440
ggcctgccgg gttggagcat tcatacatct cggccaaagc gggcttggaa cctccgctcc   1500
aggacaacac taaggaggga gagactactt ccgcttcaga aacttggaga ttttctaatt   1560
tttctctcct tgggaacttt tttttttaaag aattgaattt gctatcttcc ctaacggaca   1620
gaccccttgg tgacctcatc tcctgggaca agaccggaga cccgtgcctc tccttgactg   1680
gacgttgaac tcaaaggatc tatttaagag tttaatatat gggctctcct tgctctagtc   1740
ctactcagtt tcacagagaa aagaaattaa ttatttgaat aaagtagaca ggctgctgtc   1800
tgtgccttac ttcaaaaaaa aaaaaaaaaa                                    1830
```

<210> SEQ ID NO 40
<211> LENGTH: 173
<212> TYPE: PRT
<213> ORGANISM: Helicobacter pylori

<400> SEQUENCE: 40

```
Glu Ser Gln Val Arg Gln Gln Phe Ser Lys Asp Ile Glu Lys Leu Leu
1               5                   10                  15

Asn Glu Gln Val Asn Lys Glu Met Gln Ser Ser Asn Leu Tyr Met Ser
            20                  25                  30

Met Ser Ser Trp Cys Tyr Thr His Ser Leu Asp Gly Ala Gly Leu Phe
        35                  40                  45

Leu Phe Asp His Ala Ala Glu Glu Tyr Glu His Ala Lys Lys Leu Ile
    50                  55                  60

Ile Phe Leu Asn Glu Asn Asn Val Pro Val Gln Leu Thr Ser Ile Ser
65                  70                  75                  80

Ala Pro Glu His Lys Phe Glu Gly Leu Thr Gln Ile Phe Gln Lys Ala
                85                  90                  95

Tyr Glu His Glu Gln His Ile Ser Glu Ser Ile Asn Asn Ile Val Asp
            100                 105                 110

His Ala Ile Lys Ser Lys Asp His Ala Thr Phe Asn Phe Leu Gln Trp
        115                 120                 125

Tyr Val Ala Glu Gln His Glu Glu Val Leu Phe Lys Asp Ile Leu
    130                 135                 140

Asp Lys Ile Glu Leu Ile Gly Asn Glu Asn His Gly Leu Tyr Leu Ala
145                 150                 155                 160

Asp Gln Tyr Val Lys Gly Ile Ala Lys Ser Arg Lys Ser
                165                 170
```

<210> SEQ ID NO 41
<211> LENGTH: 154
<212> TYPE: PRT
<213> ORGANISM: Aquifex pyrophilus

<400> SEQUENCE: 41

Met Gln Ile Tyr Glu Gly Lys Leu Thr Ala Glu Gly Leu Arg Phe Gly
1               5                   10                  15

Ile Val Ala Ser Arg Phe Asn His Ala Leu Val Asp Arg Leu Val Glu
            20                  25                  30

Gly Ala Ile Asp Ala Ile Val Arg His Gly Gly Arg Glu Glu Asp Ile
        35                  40                  45

Thr Leu Val Arg Val Pro Gly Ser Trp Glu Ile Pro Val Ala Ala Gly
    50                  55                  60

Glu Leu Ala Arg Lys Glu Asp Ile Asp Ala Val Ile Ala Ile Gly Val
65                  70                  75                  80

Leu Ile Arg Gly Ala Thr Pro His Phe Asp Tyr Ile Ala Ser Glu Val
                85                  90                  95

Ser Lys Gly Leu Ala Asp Leu Ser Leu Glu Leu Arg Lys Pro Ile Thr
            100                 105                 110

Phe Gly Val Ile Thr Ala Asp Thr Leu Glu Gln Ala Ile Glu Arg Ala
        115                 120                 125

Gly Thr Lys His Gly Asn Lys Gly Trp Glu Ala Ala Leu Ser Ala Ile
    130                 135                 140

Glu Met Ala Asn Leu Phe Lys Ser Leu Arg
145                 150

<210> SEQ ID NO 42
<211> LENGTH: 265
<212> TYPE: PRT
<213> ORGANISM: Thermotoga sp. RQ2

<400> SEQUENCE: 42

Met Glu Phe Leu Lys Arg Ser Phe Ala Pro Leu Thr Glu Lys Gln Trp
1               5                   10                  15

Gln Glu Ile Asp Asn Arg Ala Arg Glu Ile Phe Lys Thr Gln Leu Tyr
            20                  25                  30

Gly Arg Lys Phe Val Asp Val Glu Gly Pro Tyr Gly Trp Glu Tyr Ala
        35                  40                  45

Ala His Pro Leu Gly Glu Val Glu Val Leu Ser Asp Glu Asn Glu Val
    50                  55                  60

Val Lys Trp Gly Leu Arg Lys Ser Leu Pro Leu Ile Glu Leu Arg Ala
65                  70                  75                  80

Thr Phe Thr Leu Asp Leu Trp Glu Leu Asp Asn Leu Glu Arg Gly Lys
                85                  90                  95

Pro Asn Val Asp Leu Ser Ser Leu Glu Glu Thr Val Arg Lys Val Ala
            100                 105                 110

Glu Phe Glu Asp Glu Val Ile Phe Arg Gly Cys Glu Lys Ser Gly Val
        115                 120                 125

Lys Gly Leu Leu Ser Phe Glu Glu Arg Lys Ile Glu Cys Gly Ser Thr
    130                 135                 140

Pro Lys Asp Leu Leu Glu Ala Ile Val Arg Ala Leu Ser Ile Phe Ser
145                 150                 155                 160

Lys Asp Gly Ile Glu Gly Pro Tyr Thr Leu Val Ile Asn Thr Asp Arg
                165                 170                 175

Trp Ile Asn Phe Leu Lys Glu Glu Ala Gly His Tyr Pro Leu Glu Lys

```
            180                 185                 190
Arg Val Glu Glu Cys Leu Arg Gly Gly Lys Ile Ile Thr Thr Pro Arg
            195                 200                 205

Ile Glu Asp Ala Leu Val Val Ser Glu Arg Gly Gly Asp Phe Lys Leu
            210                 215                 220

Ile Leu Gly Gln Asp Leu Ser Ile Gly Tyr Glu Asp Arg Glu Lys Asp
225                 230                 235                 240

Ala Val Arg Leu Phe Ile Thr Glu Thr Phe Thr Phe Gln Val Val Asn
                245                 250                 255

Pro Glu Ala Leu Ile Leu Leu Lys Phe
            260                 265

<210> SEQ ID NO 43
<211> LENGTH: 309
<212> TYPE: PRT
<213> ORGANISM: Acidianus Tengchongensis

<400> SEQUENCE: 43

Tyr Leu Phe Arg Leu Cys Tyr Ser Cys Ala Ser Gln Met Val Trp Gly
1               5                   10                  15

Pro Trp Glu Pro Ile Tyr Glu Ile Lys Tyr Ala Asp Met Pro Ile Asn
            20                  25                  30

Thr Glu Met Thr Asp Phe Thr Ala Val Val Gly Lys Lys Phe Ala Glu
        35                  40                  45

Gly Lys Pro Leu Glu Ile Pro Val Ile Ser Gln Pro Tyr Gly Lys Arg
    50                  55                  60

Val Val Ala Phe Gly Glu His Thr Val Ile Pro Gly Lys Glu Glu Gln
65                  70                  75                  80

Phe Glu Asp Ala Ile Ile Lys Thr Leu Glu Met Phe Lys Arg Ala Pro
                85                  90                  95

Gly Phe Leu Gly Ala Met Leu Leu Lys Glu Ile Gly Val Ser Gly Ile
            100                 105                 110

Gly Ser Phe Gln Phe Gly Ser Lys Gly Phe His Gln Leu Leu Glu Ser
        115                 120                 125

Pro Gly Ser Leu Glu Pro Asp Pro Asn Asn Val Met Tyr Gln Ala Pro
    130                 135                 140

Glu Ala Lys Pro Thr Pro Pro Gln Tyr Ile Val His Val Glu Trp Ala
145                 150                 155                 160

Asn Leu Asp Ala Leu Gln Phe Gly Met Gly Arg Val Leu Leu Ser Pro
                165                 170                 175

Glu Tyr Arg Glu Val His Asp Glu Ala Leu Asp Thr Leu Ile Tyr Gly
            180                 185                 190

Pro Tyr Ile Arg Ile Ile Asn Pro Val Met Glu Gly Thr Phe Trp Arg
        195                 200                 205

Glu Tyr Leu Asn Glu Gly Ser Gly Pro Lys Pro Tyr Ile Ala Ile Asn
    210                 215                 220

Met Ala Asp Leu Lys Asn Glu Pro Lys Thr Phe Glu Met Phe Ser Ala
225                 230                 235                 240

Val Gly Pro Lys Val Cys Met Val Thr Ala Arg His Pro Gly Phe Val
                245                 250                 255

Gly Phe Gln Asn His Val Gln Ile Gly Val Leu Pro Phe Gly Glu Arg
            260                 265                 270

Phe Gly Gly Ala Lys Met Asp Met Thr Lys Glu Ser Thr Val Arg
        275                 280                 285
```

-continued

```
Val Leu Gln Tyr Thr Met Trp Lys Asp Trp Lys Asp His Glu Glu Met
    290                 295                 300
His Arg Gln Asn Trp
305
```

HIV THERAPEUTICS AND METHODS OF MAKING AND USING SAME

CROSS REFERENCE TO RELATED APPLICATIONS

This is the U.S. National Stage of International Application No. PCT/US2013/074801, filed Dec. 12, 2013, which was published in English under PCT Article 21(2), which in turn claims the benefit of U.S. Provisional Application No. 61/736,350, filed Dec. 12, 2012. The provisional application is incorporated by reference herein in its entirety.

FIELD

This disclosure relates to HIV neutralizing peptides, sulfated HIV-1 envelope proteins and immunogenic fragments thereof, for treatment and prevention of Human Immunodeficiency Virus (HIV) infection and disease.

BACKGROUND

Over 30 million people are infected with HIV worldwide, and 2.5 to 3 million new infections have been estimated to occur yearly. Although effective antiretroviral therapies are available, millions succumb to AIDS every year, especially in sub-Saharan Africa, underscoring the need to develop measures to prevent the spread of this disease.

An enveloped virus, HIV-1 hides from humoral recognition behind a wide array of protective mechanisms. The major envelope protein of HIV-1 is a glycoprotein of approximately 160 kD (gp160). During infection proteases of the host cell cleave gp160 into gp120 and gp41. gp41 is an integral membrane protein, while gp120 protrudes from the mature virus. Together gp120 and gp41 make up the HIV envelope spike, which is a target for neutralizing antibodies. Further, HIV envelope binds to CD4 and CC chemokine receptor 5 (CCR5) as co-receptors required for cellular entry and infection.

It is believed that immunization with an effective immunogen based on the HIV-1 envelope glycoprotein can elicit a neutralizing response, which may be protective against HIV infection. Further, it is believed that peptide therapeutics based on gp120 can neutralize gp120, and thus HIV. However, despite extensive effort, a need remains for immunogens and peptide therapeutics capable of such action.

SUMMARY

Disclosed herein is the surprising discovery that the second variable loop (V2) of gp120 contains previously unrecognized sulfated tyrosines that bolster its intramolecular interaction with the third variable loop (V3) loop, thereby constraining the HIV-1 envelope in its native, antibody-shielded conformation. Further, the sulfated region of V2 molecularly mimics the CCR5 N-terminal domain because both regions can adopt an α-helix conformation and lock onto the conserved base of V3. Upon binding to V3, a peptide including the tyrosine-sulfated region of V2 competes with CCR5 binding to gp120, thereby inhibiting HIV infection. Surprisingly, this V2 peptide also binds to CD4, further contributing to inhibition of HIV infection. These discoveries led to the identification of novel HIV-1 therapeutic peptides, as well as sulfated HIV-1 envelope proteins, fragments thereof containing gp120 positions 173 and/or 177, and methods of making and using such molecules.

In some embodiments, a method of making a sulfated HIV-1 envelope protein or immunogenic fragment thereof is provided. The method can include providing a plurality of HIV-1 envelope proteins or immunogenic fragments thereof comprising tyrosine residues at gp120 positions 173, 177, or 173 and 177, and sulfating the tyrosine residues at gp120 positions 173, 177, or 173 and 177 on at least 90% of the HIV-1 envelope proteins or immunogenic fragments in the plurality of HIV-1 envelope proteins or immunogenic fragments. The method can further include purifying the plurality of HIV-1 envelope proteins or immunogenic fragments.

In some embodiments, a method of making a sulfated HIV-1 envelope protein or immunogenic fragment thereof is provided, including co-expression of a first and a second heterologous nucleic acid molecule in a cell. The first heterologous nucleic acid molecule encodes a HIV-1 envelope protein or immunogenic fragment thereof, wherein the HIV-1 envelope protein or immunogenic fragment thereof comprises tyrosine residues at gp120 positions, 173, 177, or 173 and 177. The second heterologous nucleic acid molecule encodes a tyrosine sulfotransferase. The first and second nucleic acid molecules are expressed in the cell under conditions sufficient for efficient sulfation of the tyrosine residues at gp120 positions 173, 177, or 173 and 177 of the HIV envelope protein or immunogenic fragment thereof. Following expression, the sulfated HIV-1 envelope protein or immunogenic fragment thereof can be purified.

In some embodiments, a method of making a sulfated HIV-1 envelope protein or immunogenic fragment thereof is provided, including incubating a HIV-1 envelope protein or immunogenic fragment thereof comprising tyrosine residues at gp120 positions 173, 177, or 173 and 177 with a purified tyrosine sulfotransferase under conditions sufficient for sulfation of the tyrosine residues. Following incubation, the sulfated HIV-1 envelope protein or immunogenic fragment thereof can be purified.

In several embodiments, the HIV-1 envelope protein or immunogenic fragment comprises gp160, gp140, or gp120.

In some embodiments, the HIV-1 envelope protein or immunogenic fragment comprises both the V2 and the V3 loop combined or complexed within the same preparation. Thus, the sulfated tyrosine residues at gp120 positions 173, 177, or 173 and 177, can bind to the base of the V3 loop and recreate the physiological complex that is presented in the native envelope.

Some embodiments include the sulfated HIV-1 envelope protein or immunogenic fragment thereof made by the disclosed methods.

In further embodiments, HIV neutralizing peptides are disclosed that include gp120 positions 171-178 according to the HXB2 numbering system and correspond to the amino acid positions in the amino acid sequence set forth as SEQ ID NO: 1. In some embodiments, the HIV neutralizing peptide includes gp120 positions 168-185 according to the HXB2 numbering system and corresponding to the amino acid positions in the amino acid sequence set forth as SEQ ID NO: 1. The HIV neutralizing peptides include a first sulfated tyrosine at position 173, a second sulfated tyrosine at position 177, or both a first sulfated tyrosine at position 173 and a second sulfated tyrosine at position 177, at most four additional amino acid substitutions compared to a wild-type HIV-1 gp120, and they are at most 50 amino acids in length; and neutralize HIV. In several embodiments, the HIV neutralizing peptides compete with CCR5 for binding to gp120. In several embodiments, the HIV neutralizing peptides increase the sensitivity of HIV to neutralization with antibodies directed to the V3-loop, the CD4 binding site or other neutralization epitopes.

In additional embodiments, the disclosed HIV neutralizing peptides or sulfated HIV-1 envelope proteins or immunogenic fragments are included in a pharmaceutical composition, such as an immunogenic composition. In several embodiments the composition includes an anti-retroviral agent.

Additional embodiments include a composition comprising a plurality of HIV-1 envelope proteins or immunogenic fragments thereof comprising tyrosine residues at gp120 positions 173, 177, or 173 and 177, wherein at least 90% of the tyrosine residues at gp120 positions 173, 177, or 173 and 177 on the HIV-1 envelope proteins or immunogenic fragments in the plurality of HIV-1 envelope proteins or immunogenic fragments are sulfated. The composition may be a pharmaceutical composition suitable for administration to a subject, and may also be contained in a unit dosage form. The HIV-1 envelope proteins or immunogenic fragments may also be conjugated to a carrier (such as a monomeric subunit of a protein nanoparticle) to facilitate presentation to the immune system.

Methods of generating an immune response in a subject are disclosed, as are methods of treating, inhibiting or preventing a HIV-1 infection in a subject. In such methods a subject, such as a human subject, is administered an effective amount of a disclosed HIV neutralizing peptide or sulfated HIV-1 envelope protein or immunogenic fragment. Several embodiments also include administering to the subject a therapeutically effective amount of an anti-retroviral agent in combination with the disclosed HIV neutralizing peptide.

The foregoing and other objects, features, and advantages of the invention will become more apparent from the following detailed description, which proceeds with reference to the accompanying figures.

BRIEF DESCRIPTION OF THE DRAWINGS

FIGS. 1A-1D depict a sequence alignment, a ribbon diagram and a graph illustrating the conservation and predicted structure within the V2 loop of HIV-1 gp120. (A) Consensus sequences of the V2 domain of gp120 in different HIV-1 genetic subtypes (A to F; SEQ ID NOs: 15-20, respectively). Within each subtype, amino acid (aa) conservation greater than 80% is shown by a grey background, between 60% and 80% by a light grey background, and less than 60% by a white background. Conservative substitutions were considered as conserved residues according to standard Clustal parameters. Identical residues in all subtype consensus sequences are indicated by an asterisk; conserved substitutions by a colon; semi-conserved substitutions by a period. Residues are numbered using the HXB2 reference sequence. Since no consensus sequence was obtained for the C-terminal variable region, the average number of aa (±SD) is indicated in parenthesis for each subtype. (B) Prediction of the secondary structure of the V2 loop of HIV-1 BaL (SEQ ID NO: 21) using 5 different algorithms (Agadir, GOR V, Jufo 9, Psi-Pred, NNPred). The grey background indicates a predicted α-helix. Residue numbering follows the HXB2 reference sequence. (C) Prediction of the three-dimensional structure of the V2 segment spanning aa 168-178 using Gromacs (grey) and ROSETTA (cyan). (D) Circular dichroism analysis of V2-derived peptides pV2α and pV2α-Pro spanning amino acids 168-185.

FIGS. 2A-2K depict digital images and diagrams illustrating that the V2 domain of HIV-1 gp120 contains sulfated tyrosines and is predicted to interact with the CCR5-binding site at the base of V3. (A) Sequence alignment of the CCR5 N-terminal domain (SEQ ID NO: 22) and the V2 α-helix (residues 14-24 of SEQ ID NO: 21). The grey background highlights two conserved tyrosine residues in both sequences. The V2 residue numbering follows the HXB2 reference sequence. (B) Detection of sulfated tyrosines in gp120 from HIV-1 virions produced in primary human CD4$^+$ T cells. gp120 was immunoprecipitated from whole HIV-1 virions produced in primary CD4$^+$ T cells and analyzed by Western blot with a monoclonal antibody specific for sulfated tyrosines; an anti-gp120 antibody (IgG1-b12) was tested in parallel as a control. (C) Detection of sulfated tyrosines in cells expressing either wild-type HIV-1 BaL gp160 or a ΔV2 (Δ164-190) mutant using a vaccinia virus system. The protein was immunoprecipitated from the cell surface and analyzed by Western blot as described for (B). (D) Detection of sulfated tyrosines in cells expressing either wild-type HIV-1 BaL gp160 or phenylalanine-substituted mutants BaL Y173F, BaL Y177F, BaL Y173F/Y177F using a vaccinia virus system. The protein was immunoprecipitated from the cell surface and analyzed by Western blot as described for (B). (E) Interaction energy between sulfated (Tys) or non-sulfated (Tyr) tyrosine 177 and gp120. Non-bonded interaction energy, separated into van der Waals (vdW) and electrostatic terms, was measured in molecular dynamics simulations of 100 nsec. As expected, the presence of the sulfo-group leads to a large increase in the electrostatic component of the interaction energy. (F to H) Predicted interaction of the V2 α-helix with the conserved base of the V3 loop. Three-dimensional representations of tyrosine-sulfated peptide pV2α-Tys interacting with the base of V3 after docking followed by molecular dynamics analysis. (F) Panoramic view of the interaction between the helix-containing peptides and the base of V3. (G) Top view of H-bond interactions of Tys177 inside the cavity at the base of V3. (H) Sectional view of H-bond interactions of Tys177 inside the cavity. (I) Two-dimensional LigPlot representation of the interactions between the central region of pV2α-Tys (Tys173 to Tys177) with the base of V3. (J) The specificity of anti-sulfotyrosine mAb 1C-A2 used in Western blot analyses was validated in ELISA tests against a tyrosine-sulfated V2-derived synthetic peptide (pV2α-Tys) and its unsulfated counterpart (pV2α).

FIGS. 3A-3H are a series of graphs illustrating that a tyrosine-sulfated peptide containing the V2 α-helix binds to gp120, competes with an anti-CCR5-binding site antibody for HIV-1 virion binding, and blocks HIV-1 entry, infection and fusion. (A) Effect of tyrosine-sulfated V2-loop (pV2α-Tys) and CCR5 N-terminus (pCCR5-Tys) mimetic peptides on HIV-1 virion capture by mAb 412d, a sulfated mAb directed to the CCR5-binding site at the base of V3. Unsulfated homologous peptides (pV2α and pCCR5) were tested in parallel as controls. Infectious viral stocks from HIV-1 BaL were pre-treated with the peptides (each at 50 μM) and then incubated with immunomagnetic beads armed with mAb 412d; beads armed with mAb 2G12 (directed to a glycan-dependent epitope on the gp120 outer domain) were used in parallel as a control. Asterisks denote significant differences with the untreated control (p<0.05 by unpaired Student's t test). (B) Dose-dependent effect of peptides pV2α and pV2α-Tys on cell-free infection by HIV-1 BaL in primary CD4+ T cells. (C) Effect of peptides pV2α and pV2α-Tys, each used at 50 μM, on cell-free infection of purified CD4+ T cells by different strains of HIV-1. Five primary isolates minimally passaged in vitro (92US714, 92HT599, 07USLR, 07USPC, subtype B; 97ZA009, subtype C) and 4 laboratory-expanded strains (BaL, JR-FL, ADA, IIIB, all subtype B) were tested. (D) Effect of peptide pV2α-Tys, used at 50 μM, on HIV-1 BaL entry into activated primary human CD4+ T cells. Peptide T20 was used as a control at 50 μg/mL. The asterisks denote significant differences with the untreated control (p<0.05 by unpaired Student's t-test). (E) Inhibition of soluble CD4-activated fusion between HIV-1 BaL envelope-expressing cells and CCR5+ CD4− cells by peptide pV2α-Tys used at 50 μM. The asterisks denote significant differences with the untreated control (p<0.05 by unpaired Student's t test). (F) Binding of gp120 to immobilized peptide pV2α as assessed by surface plasmon resonance analysis. (G) Comparison between modeled V3 interactions of tyrosine-sulfated peptides derived from the N-terminal region of CCR5 and the central region of V2. A representative snapshot from a molecular dynamics (MD) simulation of the V2 peptide in the CCR5-like helical fold was used. (H) Comparison between the experimentally determined V3 interaction of the tyrosine sulfated CDRH3 region of mAb 412d and the modeled V3 interaction of a tyrosine sulfated peptide derived from the central region of V2. A representative snapshot from an MD simulation of the V2 peptide in the 412d-like extended conformation was used.

(FIG. 7) Funnel plot of ROSETTA FlexPepDock simulations with the V2 α-helix docked to the base of V3. The backbone RMSD of decoys from the ROSETTA FlexPepDock simulation to the starting V2 α-helix model are plotted against the side-chain energies at the peptide-protein interface (I_sc). The data points represent individual decoys resulting from independent simulations; light grey dots indicate decoys in which the sidechain atoms of Tys177 are superposed within 3 Å to the corresponding atoms of the mAb 412d Tys in the gp120 co-crystal structure (PDB ID: 2QAD); dark grey dots indicate decoys with a distance greater than 3 Å. (FIG. 8) Three-dimensional representation of the lowest-energy model of the tyrosine-sulfated V2 α-helix (dark grey ribbon) docked to the V3 base (lighter grey surface) obtained from ROSETTA FlexPepDock showing Tys177 (analogous to Tys14 in CCR5) positioned inside a cavity at the base of V3.

FIG. 11 is a set of graphs illustrating exposure of CD4-induced epitope (48d) in V2 mutants of gp160 treated with soluble CD4. Disruption of V2 alpha-helix reduces binding of 48d. Wild-type and mutated gp160 envelope glycoproteins of HIV-1 BaL were expressed by recombinant vaccinia vectors on the surface of HeLa. BaL Pro 2.0 contain a proline inserted between Tyr 173 and Ala 174, while BaL Pro 2.8 contains a single proline insertion upstream of the α-helix (between Val169 and Gln170). Binding of soluble 48d was evaluated by flow cytometry in the presence or absence of sCD4, incubating the gp160 expressing cells with 48d at the indicated concentration at room temperature in PBS. After 20 minutes the excess of 48d was removed and the binding was evaluated using an anti-human IgG polyclonal sera.

(A) Modulation of V2 tyrosine sulfation affects gp120 epitope accessibility. Hypersulfation of V2 was achieved by overexpression of the sulfating enzyme TPST2 in HeLa cells expressing HIV-1 BaL gp160; inhibition of sulfation by treatment with the sulfotransferase inhibitor sodium chlorate (NaClO$_3$; 30 mM). The exposure of various gp120 and gp41 epitopes was tested by flow cytometry using a panel of specific human mAb directed to the indicated domains of gp120 or 2-domain soluble CD4 (sCD4) (all at 5 µg/ml). Mean fluorescence intensity (MFI) for the reference mAb 2G12 were used to confirm that gp120 was expressed at similar levels in the three cultures. (B,C) Modulation of V2 tyrosine sulfation affects HIV-1 neutralization sensitivity. The same reagents as in A. were used at different concentrations to neutralize HIV-1 envelope-mediated fusion. The fusion assay was performed using vaccinia technology with HeLa cells expressing HIV-1 BaL gp160 as effectors and NIH3T3 cells expressing human CD4 and CCR5 as target cells.

Figure 18:
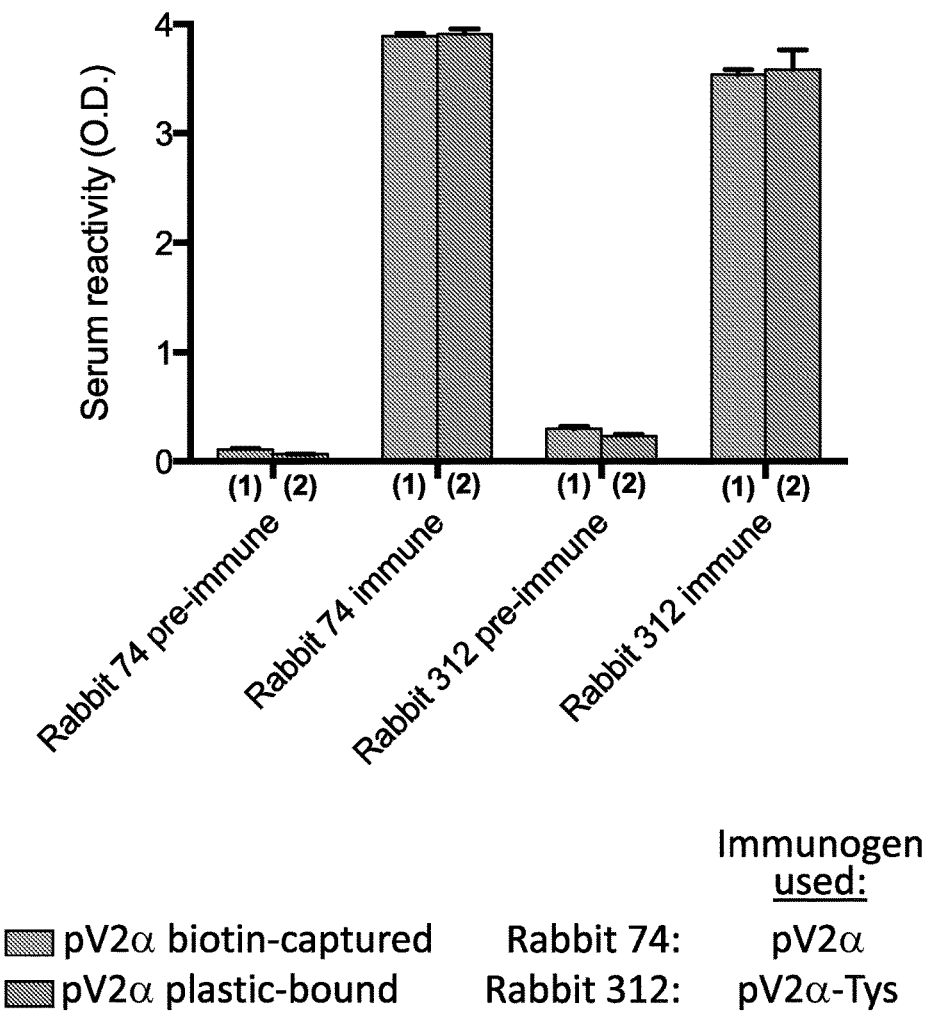

FIG. 18 is a graph illustrating that the pV2α and pV2α-Tys peptides are immunogenic. Rabbits were immunized with the pV2α or pV2α-Tys peptide and the resulting sera collected for testing for binding to the pV2α or pV2α-Tys peptide. All sera were heat-inactivated and tested in standard ELISA tests at 1:200 final dilution.

FIG. 19 is a graph illustrating that antibodies against the V2α-helix are present in sera from HIV-1-infected individuals. Sera from HIV patients was collected and tested for binding to the pV2α peptide. All sera were heat-inactivated and tested in standard ELISA tests at 1:50 final dilution.

FIG. 20 is a graph illustrating that sera from HIV-1-infected individuals contain antibodies that recognize the folded V2 peptide but have limited reactivity with the linear peptide bound to plastic. Serum from five different HIV-1 patients was tested for binding to the pV2α peptide in folded (pV2α-biotin-captured) or linear (unfolded; pV2α plastic-bound) form. Human sera were heat-inactivated and tested in standard ELISA tests at 1:50 final dilution.

Figure 21A:
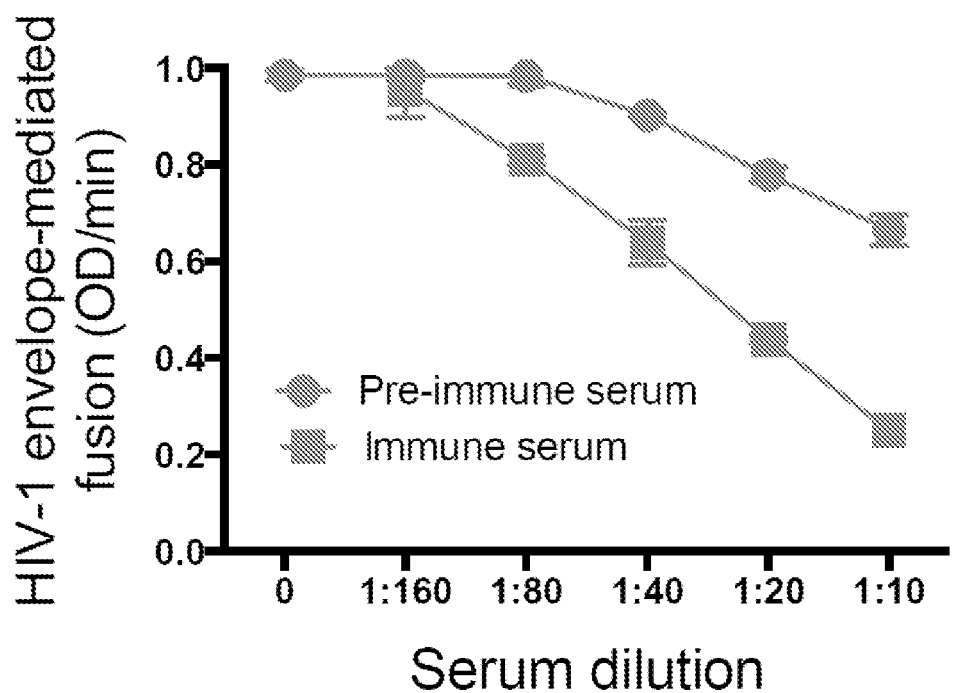
Figure 21B:
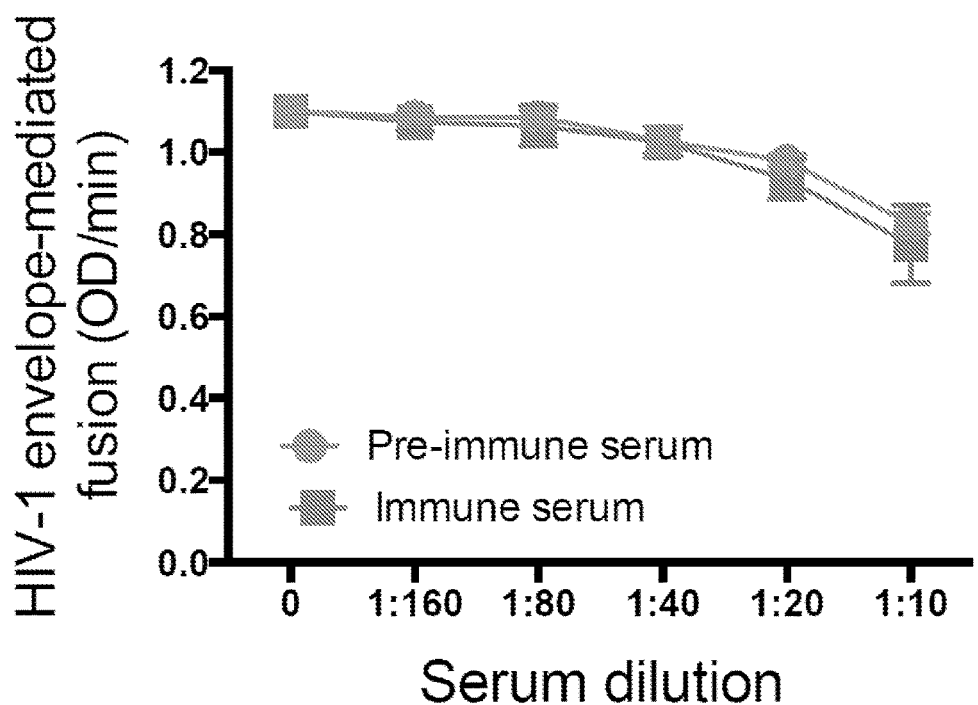

FIGS. 21A-21B are a set of graphs illustrating the neutralization of HIV-1 envelope mediated fusion by serially diluted sera from a rabbit immunized with KLH-conjugated peptide pV2α-Tys. Immunization was carried out using the mighty quick protocol by Pocono Farms and Laboratory. The immune serum tested was obtained from the 3rd bled performed 8 weeks after the first inoculation (FIG. 21A). The pre-immune serum from the same animal was tested in parallel as a control (FIG. 21B). Sera were heat-inactivated prior to use. The fusion assay was performed using HEK293 cells expressing WT HIV-1 BaL gp160as effectors and NIH3T3 cells expressing human CD4 and CCR5 as targets. The effector cells were pre-incubated with rabbit sera at the indicated dilutions for 20 min at room temperature prior to co-culture with target cells for 2 hours at 37° C. The extent of fusion was detected by colorimetric assay for beta-galactosidase activity.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named "Sequence.txt" (~1.0 mb), which was created on Jun. 9, 2015, and is incorporated by reference herein. In the accompanying Sequence Listing:

SEQ ID NO: 1 is the amino acid sequence of gp120 from HIV-1 strain HXB2 (GENBANK® Accession No. K03455, incorporated by reference herein as present in the database on Jul. 27, 2012).

SEQ ID NO: 2 is a consensus amino acid sequence for a HIV neutralizing peptide.

SEQ ID NOs: 3-6 are the amino acid sequences of HIV neutralizing peptides.

SEQ ID NO: 7 is a consensus amino acid sequence for a HIV neutralizing peptide.

SEQ ID NOs: 8-14 are the amino acid sequences of HIV neutralizing peptides.

SEQ ID NOs: 15-21 are amino acid sequences of the V2 loop of gp120.

SEQ ID NO: 22 is the amino acid sequence of the N-terminus of CCR5.

SEQ ID NOs: 23-29 are the amino acid sequences of gp160 proteins.

SEQ ID NOs: 30-39 are protein and exemplary nucleotide sequences encoding human and mouse TPST1 and TPST2 proteins.

SEQ ID NOs: 40-43 are protein nanoparticle monomer sequences.

DETAILED DESCRIPTION

I. Terms

Unless otherwise noted, technical terms are used according to conventional usage. Definitions of common terms in molecular biology can be found in Benjamin Lewin, *Genes VII*, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen."

As used herein, the term "comprises" means "includes." Thus, "comprising an antigen" means "including an antigen" without excluding other elements.

It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments, the following explanations of terms are provided:

412d Antibody: A monoclonal antibody that specifically binds to gp120 and competes with CCR5 binding to gp120. 412d antibody was shown by crystallography to interact with the CCR5-binding site at the V3 loop of gp120 (Huang et al., *Science* 317, 1930-1934, 2007). The person of ordinary skill in the art is familiar with 412d antibody.

Adjuvant: A vehicle used to enhance antigenicity. Adjuvants include a suspension of minerals (alum, aluminum hydroxide, or phosphate) on which antigen is adsorbed; or water-in-oil emulsion, for example, in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunostimulatory oligonucleotides (such as those including a CpG motif) can also be used as adjuvants. Adjuvants include biological molecules (a "biological adjuvant"), such as costimulatory molecules. Exemplary adjuvants include IL-2, RANTES, GM-CSF, TNF-α, IFN-γ, G-CSF, LFA-3, CD72, B7-1, B7-2, OX-40L, 4-1BBL and toll-like receptor (TLR) agonists, such as TLR-9 agonists. The person of ordinary skill in the art is familiar with adjuvants (see, e.g., Singh (ed.) Vaccine Adjuvants and Delivery Systems. Wiley-Interscience, 2007).

Administration: The introduction of a composition into a subject by a chosen route. Administration can be local or systemic. For example, if the chosen route is intravenous, the composition (such as a composition including a disclosed immunogen) is administered by introducing the composition into a vein of the subject.

Agent: Any substance or any combination of substances that is useful for achieving an end or result; for example, a substance or combination of substances useful for inhibiting HIV infection in a subject. Agents include proteins, nucleic acid molecules, compounds, small molecules, organic compounds, inorganic compounds, or other molecules of interest. An agent can include a therapeutic agent (such as an anti-retroviral agent), a diagnostic agent or a pharmaceutical agent. In some embodiments, the agent is a protein agent (such as a HIV-1 neutralizing peptide or sulfated HIV-1 envelope protein or immunogenic fragment thereof), or an anti-viral agent. The skilled artisan will understand that particular agents may be useful to achieve more than one result.

Alpha Helix: A particular helical folding of a polypeptide backbone in protein molecules, in which the carbonyl oxygens are hydrogen bonded to amide nitrogen atoms three residues along the chain. In a typical alpha helix, the translation of amino acid residues along the long axis of the helix is 0.15 nm and the rotation per residue is 100°; accordingly, there are 3.6 residues per turn. Side chains of helix-resident amino acids are arranged at the outside of the helix.

Amino acid substitutions: The replacement of one amino acid in a peptide with a different amino acid. In some examples, an amino acid in a peptide is substituted with an amino acid from a homologous antigen.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide substantially encoded by an immunoglobulin gene or immunoglobulin genes, or antigen binding fragments thereof, which specifically binds and recognizes an analyte (antigen) such as gp120 or an antigenic fragment of gp120 Immunoglobulin genes include the kappa, lambda, alpha, gamma, delta, epsilon and mu constant region genes, as well as the myriad immunoglobulin variable domain genes. The term "antibody," as used herein, also includes antigen binding fragments either produced by the modification of whole antibodies or those synthesized de novo using recombinant DNA methodologies. See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

Examples of antigen binding fragments include: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) (Fab')$_2$, the fragment of the antibody obtained by treating whole antibody with the enzyme pepsin without subsequent reduction; (4) F(ab')$_2$, a dimer of two Fab' fragments held together by two disulfide bonds; (5) Fv, a genetically engineered fragment containing the variable domain of the light chain and the variable domain of the heavy chain expressed as two chains; and (6) single chain antibody ("SCA"), a genetically engineered molecule containing the variable domain of the light chain, the variable domain of the heavy chain, linked by a suitable polypeptide linker as a genetically fused single chain molecule.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region (the regions are also known as "domains"). In several embodiments, the heavy and the light chain variable domains combine to specifically bind the antigen. In additional embodiments, only the heavy chain variable domain is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996). Light and heavy chain variable domains contain a "framework" region interrupted by three hypervariable regions, also called "complementarity-determining regions" or "CDRs" (see, e.g., Kabat et al., *Sequences of Proteins of Immunological Interest*, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, Md., 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a $V_H$ CDR3 is the CDR3 from the variable domain of the heavy chain of the antibody in which it is found, whereas a $V_L$ CDR1 is the CDR1 from the variable domain of the light chain of the antibody in which it is found. Light chain CDRs are sometimes referred to as LCDR1, LCDR2, and LCDR3. Heavy chain CDRs are sometimes referred to as LCDR1, LCDR2, and LCDR3.

References to "$V_H$" or "VH" refer to the variable domain of an immunoglobulin heavy chain, including that of an antigen binding fragment, such as Fv, scFv, dsFv or Fab. References to "$V_L$" or "VL" refer to the variable domain of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected, or a progeny thereof. Monoclonal antibodies are produced by methods known to those of skill in the art, for instance by making hybrid antibody-forming cells from a fusion of myeloma cells with immune spleen cells. These fused cells and their progeny are termed "hybridomas." Monoclonal antibodies include humanized and fully human monoclonal antibodies. In some examples monoclonal antibodies are isolated from a subject. The amino acid sequences of such isolated monoclonal antibodies can be determined Monoclonal antibodies can have conservative amino acid substitutions which have substantially no effect on antigen binding or other immunoglobulin functions. (See, for example, Harlow & Lane, *Antibodies, A Laboratory Manual*, Cold Spring Harbor Publications, New York (1988).)

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous antigens, such as the disclosed antigens. Examples of antigens include, but are not limited to, polypeptides, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. In specific examples, an antigen is derived from HIV, such as a gp120 polypeptide, gp41 polypeptide, or antigenic fragment thereof, such as a gp120 outer domain or fragment thereof.

Anti-retroviral agent: An agent that specifically inhibits a retrovirus from replicating or infecting cells. Non-limiting examples of antiretroviral drugs include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon).

Anti-retroviral therapy (ART): A therapeutic treatment for HIV infection involving administration of at least one anti-retroviral agents (e.g., one, two, three or four anti-retroviral agents) to an HIV infected individual during a course of treatment. Non-limiting examples of antiretroviral agents include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon). One example of an ART regimen includes treatment with a combination of tenofovir, emtricitabine and efavirenz. In some examples, ART include Highly Active Anti-Retroviral Therapy (HAART).

B cell: A subset of lymphocytes, that is, white blood cells (leukocytes). Mature B cells differentiate into plasma cells, which produces antibodies, and memory B cells. Mature B cells have acquired surface IgM and IgD, are capable of responding to antigen, and express characteristic markers such as CD21 and CD23. Plasma cells are terminally differentiated B cells that are the predominant antibody-secreting cells.

CC chemokine receptor 5 (CCR5): A chemokine receptor which binds members of the C—C group of chemokines, and functions as a co-receptor for HIV-1 required for HIV-1 viral entry. The V3 loop of HIV-1 is known to interact with an alpha-helical structure on the extracellular domain of CCR5. Exemplary protein and nucleic acid sequences for CCR5 are known to the person of ordinary skill in the art, see, e.g., GENBANK® Acc. No. 1705896, Oppermann et al., *Cell Signal*. (2004) 16:1201-10).

CD4: Cluster of differentiation factor 4 polypeptide; a T-cell surface protein that mediates interaction with the MHC class II molecule. CD4 also serves as the primary receptor site for HIV on T-cells during HIV-I infection. CD4 is known to bind to gp120 from HIV. The known sequence of the CD4 precursor has a hydrophobic signal peptide, an extracellular region of approximately 370 amino acids, a highly hydrophobic stretch with significant identity to the membrane-spanning domain of the class II MHC beta chain, and a highly charged intracellular sequence of 40 resides (Maddon, *Cell* 42:93, 1985).

The term "CD4" includes polypeptide molecules that are derived from CD4 include fragments of CD4, generated either by chemical (for example enzymatic) digestion or genetic engineering means. Such a fragment may be one or more entire CD4 protein domains. The extracellular domain of CD4 consists of four contiguous immunoglobulin-like regions (D1, D2, D3, and D4, see Sakihama et al., *Proc. Natl. Acad. Sci.* 92:6444, 1995; U.S. Pat. No. 6,117,655), and amino acids 1 to 183 have been shown to be involved in gp120 binding. For instance, a binding molecule or binding domain derived from CD4 would comprise a sufficient portion of the CD4 protein to mediate specific and functional interaction between the binding fragment and a native or viral binding site of CD4. One such binding fragment includes both the D1 and D2 extracellular domains of CD4 (D1D2 is also a fragment of soluble CD4 or sCD4 which is comprised of D1 D2 D3 and D4), although smaller fragments may also provide specific and functional CD4-like binding. The gp120-binding site has been mapped to D1 of CD4.

CD4 polypeptides also include "CD4-derived molecules" which encompasses analogs (non-protein organic molecules), derivatives (chemically functionalized protein molecules obtained starting with the disclosed protein sequences) or mimetics (three-dimensionally similar chemicals) of the native CD4 structure, as well as proteins sequence variants or genetic alleles that maintain the ability to functionally bind to a target molecule.

Conservative variants: "Conservative" amino acid substitutions are those substitutions that do not substantially affect or decrease the affinity of a protein, such as a peptide, for another protein to which it specifically binds, such as gp120. For example, a peptide that specifically binds gp120 can include up to on, up to two, up to three, up to four, or up to five conservative amino acid substitutions, or at most about 1, at most about 2, at most about 5, and most about 10, or at most about 15 conservative substitutions and specifically bind the gp120 polypeptide. The term conservative variation also includes the use of a substituted amino acid in place of an unsubstituted parent amino acid, provided that the peptide specifically binds gp120.

Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that reduce an activity or binding to gp120. For instance, if an amino acid residue is essential for a function of the protein, even an otherwise conservative substitution may disrupt that activity. Thus, a conservative substitution does not alter the basic function of a protein of interest.

Contacting: Placement in direct physical association; includes both in solid and liquid form, which can take place either in vivo or in vitro. Contacting includes contact between one molecule and another molecule, for example the amino acid on the surface of one polypeptide, such as a peptide, that contacts another polypeptide. Contacting can also include contacting a cell for example by placing a polypeptide in direct physical association with a cell.

Control: A reference standard. In some embodiments, the control is a sample obtained from a healthy patient. In other embodiments, the control is a tissue sample obtained from a patient diagnosed with HIV infection. In still other embodiments, the control is a historical control or standard reference value or range of values (such as a previously tested control sample, such as a group of HIV patients with known prognosis or outcome, or group of samples that represent baseline or normal values).

A difference between a test sample and a control can be an increase or conversely a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Degenerate variant: In the context of the present disclosure, a "degenerate variant" refers to a polynucleotide encoding a peptide (such as a HIV-1 neutralizing peptide or sulfated HIV-1 envelope protein or immunogenic fragment thereof) that includes a sequence that is degenerate as a result of the genetic code. There are 20 natural amino acids, most of which are specified by more than one codon. Therefore, all degenerate nucleotide sequences encoding a peptide are included as long as the amino acid sequence of the peptide encoded by the nucleotide sequence is unchanged.

Detecting: To identify the existence, presence, or fact of something. General methods of detecting are known to the skilled artisan and may be supplemented with the protocols and reagents disclosed herein. For example, included herein are methods of detecting the level of a protein in a sample or a subject.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-gp120 antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{35}$S, $^{11}$C, $^{13}$N, $^{15}$O, $^{18}$F $^{19}$F, $^{99m}$Tc, $^{131}$I, $^{3}$H, $^{14}$C, $^{15}$N, $^{90}$Y $^{99}$Tc, $^{111}$In and $^{125}$I fluorophores, chemiluminescent agents, and enzymes.

Epitope: An antigenic determinant. These are particular chemical groups or peptide sequences on a molecule that are antigenic, such that they elicit a specific immune response, for example, an epitope is the region of an antigen to which B and/or T cells respond. An antibody binds a particular antigenic epitope, such as an epitope of an HIV-1 envelope protein.

Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or about 8-10 amino acids in a unique spatial conformation. Methods of determining spatial conformation of epitopes include, for example, x-ray crystallography and nuclear magnetic resonance. Epitopes can also include post-translation modification of amino acids, such as N-linked glycosylation.

A "target epitope" is a particular epitope on an antigen that specifically binds an antibody of interest, such as a monoclonal antibody. In some examples, a target epitope includes the amino acid residues that contact the antibody of interest, such that the target epitope can be selected by the amino acid residues determined to be in contact with the antibody of interest.

Expression: Transcription or translation of a nucleic acid sequence. For example, a gene is expressed when its DNA is transcribed into an RNA or RNA fragment, which in some examples is processed to become mRNA. A gene may also be expressed when its mRNA is translated into an amino acid sequence, such as a protein or a protein fragment. In a particular example, a heterologous gene is expressed when it is transcribed into an RNA. In another example, a heterologous gene is expressed when its RNA is translated into an amino acid sequence. The term "expression" is used herein to denote either transcription or translation. Regulation of expression can include controls on transcription, translation, RNA transport and processing, degradation of intermediary molecules such as mRNA, or through activation, inactivation, compartmentalization or degradation of specific protein molecules after they are produced.

Expression Control Sequences: Nucleic acid sequences that regulate the expression of a heterologous nucleic acid sequence to which it is operatively linked Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Heterologous: Originating from a different genetic source. A nucleic acid molecule that is heterologous to a cell originated from a genetic source other than the cell in which it is expressed. In one specific, non-limiting example, a heterologous nucleic acid molecule encoding an HIV-1 envelope protein is expressed in a cell, such as a mammalian cell. Methods for introducing a heterologous nucleic acid molecule in a cell or organism are well known in the art, for example transformation with a nucleic acid, including electroporation, lipofection, particle gun acceleration, and homologous recombination.

Highly active anti-retroviral therapy (HAART): A therapeutic treatment for HIV infection involving administration of multiple anti-retroviral agents (e.g., two, three or four anti-retroviral agents) to an HIV infected individual during a course of treatment. Non-limiting examples of antiretroviral agents include entry inhibitors (e.g., enfuvirtide), CCR5 receptor antagonists (e.g., aplaviroc, vicriviroc, maraviroc), reverse transcriptase inhibitors (e.g., lamivudine, zidovudine, abacavir, tenofovir, emtricitabine, efavirenz), protease inhibitors (e.g., lopivar, ritonavir, raltegravir, darunavir, atazanavir), maturation inhibitors (e.g., alpha interferon, bevirimat and vivecon). One example of a HAART regimen includes treatment with a combination of tenofovir, emtricitabine and efavirenz.

HIV Envelope protein (Env): The HIV envelope protein is initially synthesized as a longer precursor protein of 845-870 amino acids in size, designated gp160. gp160 forms a homotrimer and undergoes glycosylation within the Golgi apparatus. In vivo, it is then cleaved by a cellular protease into gp120 and gp41. gp120 contains most of the external, surface-exposed, domains of the HIV envelope glycoprotein complex, and it is gp120 which binds both to cellular CD4 receptors and to cellular chemokine receptors (such as CCR5). gp41 contains a transmembrane domain and remains in a trimeric configuration; it interacts with gp120 in a non-covalent manner.

HIV-1 gp120: An envelope protein from HIV. gp120 contains most of the external, surface-exposed, domains of the HIV envelope glycoprotein complex, and it is gp120 which binds both to cellular CD4 receptors and to cellular chemokine receptors (such as CCR5).

The mature gp120 wild-type polypeptides have about 500 amino acids in the primary sequence. The gp120 is heavily N-glycosylated giving rise to an apparent molecular weight of 120 kD. The polypeptide is comprised of five conserved regions (C1-C5) and five regions of high variability (V1-V5). Exemplary sequences of wild-type gp160 polypeptides are shown on GENBANK®, for example Accession Nos. AAB05604 and AAD12142, which are incorporated herein by reference in their entirety as available on Jun. 29, 2010. Exemplary sequences of gp120 polypeptides from HIV-1 DU156 are shown on GENBANK®, for example Accession Nos. ABD83635, AA050350 and AAT91997, which are incorporated herein by reference in their entirety as available on Sep. 27, 2010. Exemplary sequences of gp120 polypeptides from HIV-1 ZA012 are shown on GENBANK®, for example Accession No. ACF75939, which is incorporated herein by reference in its entirety as available on Sep. 27, 2010.

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either of these domains. The gp120 core comprises 25 beta strands, 5 alpha helices, and 10 defined loop segments.

The core gp120 comprises 25 β-strands, 5 α-helices and 10 defined loop segments. The polypeptide chain of gp120 is folded into two major domains, plus certain excursions that emanate from this body. The inner domain (inner with respect to the N and C termini) features a two-helix, two-strand bundle with a small five-stranded β-sandwich at its termini-proximal end and a projection at the distal end from which the V1/V2 stem emanates. The outer domain is a stacked double barrel that lies alongside the inner domain so that the outer barrel and inner bundle axes are approximately parallel. The bridging sheet (β3, β2, β21, β20) packs primarily over the inner domain, although some surface residues of the outer domain, such as Phenylalanine 382, reach in to form part of its hydrophobic core.

The V1 and V2 domains (the V1/V2 domain) of gp120 are comprised of ~50-90 residues which contain two of the most variable portions of HIV-1 (the V1 loop and the V2 loop), and one in ten residues of the V1/V2 domain are N-glycosylated. The V1/V2 domain includes approximately gp120 positions 128-194. The V3 region or V3 loop is critical for the binding of the co-receptor and determination of which of the co-receptors will bind, and includes approximately gp120 positions 293-334.

The numbering used in the gp120 derived antigens disclosed herein is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber et al., Eds. Theoretical Biology and Biophysics Group, Los Alamos National Laboratory, Los Alamos, N. Mex., which is incorporated by reference herein in its entirety.

HIV-1 gp140: An oligomeric form of HIV envelope protein, which contains all of gp120 and the entire gp41 ectodomain.

HIV-1 gp41: A HIV protein that contains a transmembrane domain and remains in a trimeric configuration; it interacts with gp120 in a non-covalent manner. The amino acid sequence of an example of gp41 is set forth in GENBANK® Accession No. CAD20975 (as available on Oct. 16, 2009) which is incorporated by reference herein. It is understood that the sequence of gp41 can vary from that given in GENBANK® Accession No. CAD20975.

HIV neutralizing peptide: A peptide which binds to a target, such as a HIV-1 protein, for example, gp120, and is capable of reducing the infectious titer of HIV-1 in a subject. In several embodiments, a HIV neutralizing peptide can bind to and inhibit the function of an HIV antigen, such as gp120, from more than one clade.

Homologous proteins: Proteins from two or more species that have a similar structure and function in the two or more species. For example a gp120 antigen from one species of lentivirus such as HIV-1 is a homologous antigen to a gp120 antigen from a related species such as HIV-2 or SIV. Homologous proteins often share the same protein folding and can be considered structural homologs.

Homologous proteins typically share a high degree of sequence conservation, such as at least 80%, at least 90%, at least 91%, at least 92%, at least 93%, at least 94%, or at least 95%, at least 96%, at least 97%, at least 98%, or at least 99% sequence conservation, and a high degree of sequence identity, such as at least 80%, at least 90%, at least 91%, at least 92%, at least 93%, at least 94%, or at least 95%, at least 96%, at least 97%, at least 98%, or at least 99% sequence identity.

Host cells: Cells in which a vector can be propagated and its DNA expressed, for example a disclosed antibody can be expressed in a host cell. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus (HIV): A retrovirus that causes immunosuppression in humans (HIV disease), and leads to a disease complex known as the acquired immunodeficiency syndrome (AIDS). "HIV disease" refers to a well-recognized constellation of signs and symptoms (including the development of opportunistic infections) in persons who are infected by an HIV virus, as determined by antibody or western blot studies. Laboratory findings associated with this disease include a progressive decline in T cells. HIV includes HIV type 1 (HIV-1) and HIV type 2 (HIV-2). Related viruses that are used as animal models include simian immunodeficiency virus (SIV), and feline immunodeficiency virus (FIV). Treatment of HIV-1 with HAART has been effective in reducing the viral burden and ameliorating the effects of HIV-1 infection in infected individuals.

HXB2 numbering system: A reference numbering system for HIV protein and nucleic acid sequences, using HIV-1 HXB2 strain sequences as a reference for all other HIV strain sequences. The person of ordinary skill in the art is familiar with the HXB2 numbering system, and this system is set forth in "Numbering Positions in HIV Relative to HXB2CG," Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex., which is incorporated by reference herein in its entirety. HXB2 is also known as: HXBc2, for HXB clone 2; HXB2R, in the Los Alamos HIV database, with the R for revised, as it was slightly revised relative to the original HXB2 sequence; and HXB2CG in GENBANK™, for HXB2 complete genome. The numbering used in gp120 polypeptides disclosed herein is relative to the HXB2 numbering scheme. For reference, the amino acid sequence of HXB2CG is provided as SEQ ID NO: 1:

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies. "Priming an immune response" refers to pre-treatment of a subject with an adjuvant to increase the desired immune response to a later administered immunogenic agent. "Enhancing an immune response" refers to co-administration of an adjuvant and an immunogenic agent, wherein the adjuvant increases the desired immune response to the immunogenic agent compared to administration of the immunogenic agent to the subject in the absence of the adjuvant.

Immortalized cell: Capable of undergoing at least 25, 50, 75, 90, or 95% more cell divisions than a naturally-occurring control cell of the same cell type, genus, and species as the immortalized cell or than the donor cell from which the immortalized cell was derived. Preferably, an immortalized cell is capable of undergoing at least 2, 5, 10, or 20-fold more cell divisions than the control cell. In one embodiment, the immortalized cell is capable of undergoing an unlimited number of cell divisions. Examples of immortalized cells include cells that naturally acquire a mutation in vivo or in vitro that alters their normal growth-regulating process. Other immortalized cells include cells that have been genetically modified to express an oncogene, such as ras, myc, abl, bcl2, or neu, or that have been infected with a transforming DNA or RNA virus, such as Epstein Barr virus or SV40 virus (Kumar et al., *Immunol. Lett.* 65:153 159, 1999; Knight et al., *Proc. Nat. Acad. Sci. USA* 85:3130 3134, 1988; Shammah et al., *J. Immunol. Methods* 160 19 25, 1993; Gustafsson and Hinkula, *Hum. Antibodies Hybridomas* 5:98 104, 1994; Kataoka et al., *Differentiation* 62:201 211, 1997; Chatelut et al., *Scand. J. Immunol.* 48:659 666, 1998). Cells can also be genetically modified to express the telomerase gene (Rogues et al., *Cancer Res.* 61:8405 8507, 2001). In other examples, cells are treated with a substance that makes them capable of undergoing increased numbers of cell divisions than an untreated cell of the same type.

Immunogen: A protein or a portion thereof that is capable of inducing an immune response in a mammal, such as a mammal infected or at risk of infection with a pathogen. Administration of an immunogen can lead to protective immunity and/or proactive immunity against a pathogen of interest. In some examples, an immunogen is an HIV neutralizing peptide as disclosed herein.

Immunogenic composition: A composition comprising an immunogenic polypeptide that induces a measurable CTL response against virus expressing the immunogenic polypeptide, or induces a measurable B cell response (such as production of antibodies) against the immunogenic polypeptide. In one example, an "immunogenic composition" is composition includes a disclosed HIV neutralizing peptide or sulfated HIV-1 envelope protein or immunogenic fragment thereof, that induces a measurable CTL response against virus expressing gp120 polypeptide, or induces a measurable B cell response (such as production of antibodies) against a gp120 polypeptide. It further refers to isolated nucleic acids encoding an antigen, such as a nucleic acid that can be used to express the antigen (and thus be used to elicit an immune response against this peptide).

For in vitro use, an immunogenic composition may consist of the isolated protein, peptide epitope, or nucleic acid encoding the protein, or peptide epitope. For in vivo use, the immunogenic composition will typically include the protein, immunogenic peptide or nucleic acid in pharmaceutically acceptable carriers, and/or other agents. Any particular peptide, such as a disclosed HIV neutralizing peptide or a nucleic acid encoding the antigen, can be readily tested for its ability to induce a CTL or B cell response by art-recognized assays Immunogenic compositions can include adjuvants, which are well known to one of skill in the art.

Immunogenic polypeptide: A polypeptide which comprises an allele-specific motif, an epitope or other sequence such that the peptide will bind an MHC molecule and induce an immune response, such as a cytotoxic T lymphocyte ("CTL") response, and/or a B cell response (for example, antibody production), and/or a T-helper lymphocyte response against the antigen from which the immunogenic polypeptide is derived.

Inhibiting or treating a disease: Inhibiting the full development of a disease or condition, for example, in a subject who is at risk for a disease such as acquired immunodeficiency syndrome (AIDS). "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the viral load, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a cell, for example a B cell, a nucleic acid, peptide, protein or antibody) has been substantially separated, produced apart from, or purified away from other biological components in the cell of the organism in which the component naturally occurs, such as, other chromosomal and extrachromosomal DNA and RNA, and proteins. Nucleic acids, peptides and proteins which have been "isolated" thus include nucleic acids and proteins purified by standard purification methods. The term also embraces nucleic acids, peptides, and proteins prepared by recombinant expression in a host cell as well as chemically synthesized nucleic acids. In some examples a peptide, such as a HIV neutralizing peptide that specifically binds to gp120 can be isolated.

Linker: A peptide joining two peptides. In some cases, a linker is a peptide serving to link a targeting moiety, such as an gp120 binding peptide, to an effector molecule, such as a cytotoxin or a detectable label.

The terms "conjugating," "joining," "bonding" or "linking" refer to making two peptides into one contiguous peptide molecule, or to covalently attaching a radionuclide or other molecule to a peptide. The linkage can be either by chemical or recombinant means. "Chemical means" refers to a reaction between the antibody moiety and the effector molecule such that there is a covalent bond formed between the two molecules to form one molecule.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, e.g., a "recombinant peptide." A recombinant nucleic acid may serve a non-coding function (e.g., promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, e.g., by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989). An oligonucleotide is a linear polynucleotide sequence of up to about 100 nucleotide bases in length.

A polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Polypeptide: Any chain of amino acids, regardless of length or post-translational modification (such as glycosylation or phosphorylation). "Polypeptide" applies to amino acid polymers including naturally occurring amino acid polymers and non-naturally occurring amino acid polymer as well as in which one or more amino acid residue is a non-natural amino acid, for example an artificial chemical mimetic of a corresponding naturally occurring amino acid. A "residue" refers to an amino acid or amino acid mimetic incorporated in a polypeptide by an amide bond or amide bond mimetic. "Polypeptide" is used interchangeably with peptide or protein, and is used interchangeably herein to refer to a polymer of amino acid residues. A polypeptide has an amino terminal (N-terminal) end and a carboxy terminal (C-terminal) end.

Amino acids in a peptide, polypeptide or protein generally are chemically bound together via amide linkages (CONH). Additionally, amino acids may be bound together by other chemical bonds. For example, linkages for amino acids or amino acid analogs can include $CH_2NH-$, $-CH_2S-$, $-CH_2-CH_2-$, $-CH=CH-$ (cis and trans), $-COCH_2-$, $-CH(OH)CH_2-$, and $-CHH_2SO-$ (These and others can be found in Spatola, in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci pp. 463-468, 1980; Hudson, et al., *Int J Pept Prot Res* 14:177-185, 1979; Spatola et al. *Life Sci* 38:1243-1249, 1986; Harm *J. Chem. Soc Perkin Trans.* 1307-314, 1982; Almquist et al. *J. Med. Chem.* 23:1392-1398, 1980; Jennings-White et al. *Tetrahedron Lett* 23:2533, 1982; Holladay et al. *Tetrahedron. Lett* 24:4401-4404, 1983; and Hruby Life Sci 31:189-199, 1982.

Polypeptide modifications: Polypeptides and peptides, such as the HIV neutralizing peptides and sulfated HIV-1 envelope proteins disclosed herein can be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring Amino groups of the peptide, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains can be converted to $C_1$-$C_{16}$ alkoxy or to a $C_1$-$C_{16}$ ester using well-recognized techniques. Phenyl and phenolic rings of the peptide side chains can be substituted with one or more halogen atoms, such as F, Cl, Br or I, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the peptides of this disclosure to select and provide conformational constraints to the structure that result in enhanced stability. For example, a C- or N-terminal cysteine can be added to the peptide, so that when oxidized the peptide will contain a disulfide bond, generating a cyclic peptide. Other peptide cyclizing methods include the formation of thioethers and carboxyl- and amino-terminal amides and esters.

Pharmaceutical agent: A chemical compound or composition capable of inducing a desired therapeutic or prophylactic effect when properly administered to a subject or a cell. In some examples a pharmaceutical agent includes one or more of the disclosed peptides.

Pharmaceutically acceptable carriers: The pharmaceutically acceptable carriers of use are conventional. *Remington's Pharmaceutical Sciences*, by E. W. Martin, Mack Publishing Co., Easton, Pa., 19th Edition, 1995, describes compositions and formulations suitable for pharmaceutical delivery of the disclosed antibodies.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate. In particular embodiments, suitable for administration to a subject the carrier may be sterile, and/or suspended in a unit dosage form containing one or more measured doses of the composition suitable to induce the desired anti-HIV immune response. It may also be accompanied by medications for its use for treatment purposes. The unit dosage form may be, for example, in a sealed vial that contains sterile contents or a syringe for injection into a subject.

Prime-boost vaccination: An immunotherapy including administration of a first immunogenic composition (the primer vaccine) followed by administration of a second immunogenic composition (the booster vaccine) to a subject to induce an immune response. The primer vaccine and/or the booster vaccine include a vector (such as a viral vector, RNA, or DNA vector) expressing the antigen to which the immune response is directed. The booster vaccine is administered to the subject after the primer vaccine; the skilled artisan will understand a suitable time interval between administration of the primer vaccine and the booster vaccine, and examples of such timeframes are disclosed herein. In some embodiments, the primer vaccine, the booster vaccine, or both primer vaccine and the booster vaccine additionally include an adjuvant. In one non-limiting example, the primer vaccine is a DNA-based vaccine (or other vaccine based on gene delivery), and the booster vaccine is a protein subunit or protein nanoparticle based vaccine.

Protein nanoparticle: A multi-subunit, protein-based polyhedron shaped structure. The subunits are each composed of proteins or polypeptides (for example a glycosylated polypeptide), and, optionally of single or multiple features of the following: nucleic acids, prosthetic groups, organic and inorganic compounds. Non-limiting examples of protein nanoparticles include ferritin nanoparticles (see, e.g., Zhang, Y. *Int. J. Mol. Sci.*, 12:5406-5421, 2011, incorporated by reference herein), encapsulin nanoparticles (see, e.g., Sutter et al., Nature Struct. and Mol. Biol., 15:939-947, 2008, incorporated by reference herein), Sulfur Oxygenase Reductase (SOR) nanoparticles (see, e.g., Urich et al., Science, 311:996-1000, 2006, incorporated by reference herein), lumazine synthase nanoparticles (see, e.g., Zhang et al., *J. Mol. Biol.*, 306: 1099-1114, 2001) or pyruvate dehydrogenase nanoparticles (see, e.g., Izard et al., *PNAS* 96: 1240-1245, 1999, incorporated by reference herein). Ferritin, encapsulin, SOR, lumazine synthase, and pyruvate dehydrogenase are monomeric proteins that self-assemble into a globular protein complexes that in some cases consists of 24, 60, 24, 60, and 60 protein subunits, respectively. In some examples, ferritin, encapsulin, SOR, lumazine synthase, or pyruvate dehydrogenase monomers are linked to a disclosed immunogen or polypeptide (for example, a sulfated HIV-1 envelope protein) and self-assembled into a protein nanoparticle presenting the disclosed immunogen or polypeptide on its surface, which can be administered to a subject to stimulate an immune response to the antigen.

Purified: The term purified does not require absolute purity; rather, it is intended as a relative term. Thus, for example, a purified protein is one in which the protein is more enriched than the protein is in its natural environment within a cell. Preferably, a preparation is purified such that the protein represents at least 50% of the protein content of the preparation.

The immunogens and polypeptides disclosed herein, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is a protein encoded by a heterologous (for example, recombinant) nucleic acid that has been introduced into a host cell, such as a bacterial or eukaryotic cell. The nucleic acid can be introduced, for example, on an expression vector having signals capable of expressing the protein encoded by the introduced nucleic acid or the nucleic acid can be integrated into the host cell chromosome.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a HCC tissue biopsy.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are.

Homologs or variants of a peptide will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a peptide (such as a HIV neutralizing peptide) that specifically binds another peptide (such as gp120) are typically characterized by possession of at least about 75%, for example at least about 80%, 85%, 90%, 91%, 92%, 93%, 94%, 95%, 96%, 97%, 98% or 99% sequence identity counted over the full length alignment with the amino acid sequence of interest. Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specifically bind: When referring to the formation of an antibody:antigen protein complex, refers to a binding reaction which determines the presence of a target protein, peptide, or polysaccharide (for example a glycoprotein), in the presence of a heterogeneous population of proteins and other biologics. Thus, under designated conditions, an antibody binds preferentially to a particular target protein, peptide or polysaccharide (such as an antigen present on the surface of a pathogen, for example gp120) and does not bind in a significant amount to other proteins or polysaccharides present in the sample or subject. Specific binding can be determined by methods known in the art. With reference to an antibody:antigen complex, specific binding of the antigen and antibody has a $K_d$ of less than about $10^{-6}$ Molar, such as less than about $10^{-7}$ Molar, $10^{-8}$ Molar, $10^{-9}$, or even less than about $10^{-10}$ Molar.

Subject: Living multi-cellular vertebrate organisms, a category that includes human and non-human mammals. In an example, a subject is a human. In a particular example, the subject is a newborn infant. In an additional example, a subject is selected that is in need of inhibiting of an HIV infection. For example, the subject is either uninfected and at risk of HIV infection or is infected in need of treatment.

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. Th1 and Th2 cells are functional subsets of helper T cells. Th1 cells secrete a set of cytokines, including interferon-gamma, and whose principal function is to stimulate phagocyte-mediated defense against infections, especially related to intracellular microbes. Th2 cells secrete a set of cytokines, including interleukin (IL)-4 and IL-5, and whose principal functions are to stimulate IgE and eosinophil/mast cell-mediated immune reactions and to downregulate Th1 responses.

$CD8^+$ T cells carry the "cluster of differentiation 8" (CD8) marker. In one embodiment, a CD8 T cells is a cytotoxic T lymphocytes. In another embodiment, a CD8 cell is a suppressor T cell.

Therapeutic agent: Used in a generic sense, it includes treating agents, prophylactic agents, and replacement agents. A therapeutic agent is used to ameliorate a specific set of conditions in a subject with a disease or a disorder.

Therapeutically Effective Amount: An amount of a composition that alone, or together with an additional therapeutic agent(s) (for example nucleoside/nucleotide reverse transcriptase inhibitors, a non-nucleoside reverse transcriptase inhibitors, protease inhibitors, fusion/entry inhibitors or integrase inhibitors) induces the desired response (e.g., inhibition of HIV infection or replication). In several embodiments, a therapeutically effective amount is the amount necessary to reduce a sign or symptom of AIDS, and/or to decrease viral titer in a subject. When administered to a subject, a dosage will generally be used that will achieve target tissue concentrations that has been shown to achieve a desired in vitro effect.

In one example, a desired response is to inhibit HIV replication in a cell to which the therapy is administered. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of HIV), as compared to HIV replication in the absence of the composition.

In another example, a desired response is to inhibit HIV infection. The HIV infected cells do not need to be completely eliminated for the composition to be effective. For example, a composition can decrease the number of HIV infected cells by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to the number of HIV infected cells in the absence of the composition.

A therapeutically effective amount of an agent including at least one HIV neutralizing peptide, can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 µg-10 mg per 70 kg body weight if administered intravenously. A unit dosage form of the agent can be packages in a therapeutic amount, or in multiples of the therapeutic amount, for example, in a vial (e.g., with a pierceable lid) or syringe having sterile components.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule is introduced into such a cell, including transformation with plasmid vectors, and introduction of naked DNA by electroporation, lipofection, and particle gun acceleration.

Tyrosine Sulfation: Addition of a sulfate group to a tyrosine residue in a protein. In cells, tyrosine sulfation is a post translational modification where a sulfate group is added to a tyrosine residue of a protein molecule in the Golgi or endoplasmic reticulum. Tyrosine sulfation can be catalyzed by a tyrosyl-protein sulfotransferase (TPST), such as TPST1 or TPST2. The reaction catalyzed by TPST is a transfer of sulfate from the universal sulfate donor 3'-phosphoadenosine-5'-phosphosulfate (PAPS) to the side-chain hydroxyl group of a tyrosine residue. Tyrosine sulfation can also be accomplished in vitro, for example by incubating a peptide containing one or more tyrosine residues with a TBST enzyme (such as TBST1 or TBST2) under appropriate conditions. Methods of sulfating a tyrosine residue on a protein are known (see, e.g., U.S. Pat. No. 5,541,095, 2009/0042738, 2006/0009631, 2003/0170849, 2006/0115859, Liu et al., Mol. Biosyst., 7:38-47, 2011, and Choe and Farzan, Methods in Enzymology, 461: 147-170, 2009) each of which is incorporated by reference herein).

Under conditions sufficient for: A phrase that is used to describe any environment that permits a desired activity. In one example the desired activity is sulfation of a tyrosine residue. In another example the desired activity is treatment of HIV infection.

Vaccine: Composition that when administered to a subject, induces a decrease of the severity of the symptoms of a disorder or disease. In one specific, non-limiting embodiment, a vaccine decreases the severity of the symptoms associated with HIV infection and/or decreases the viral load.

Vector: A nucleic acid molecule as introduced into a host cell, thereby producing a transformed host cell. Recombinant DNA vectors are vectors having recombinant DNA. A vector can include nucleic acid sequences that permit it to replicate in a host cell, such as an origin of replication. A vector can also include one or more selectable marker genes and other genetic elements known in the art. Viral vectors are recombinant DNA vectors having at least some nucleic acid sequences derived from one or more viruses.

Virus: A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. In some examples, a virus is a pathogen.

Virus-like particle (VLP): A non-replicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. Further, VLPs can be isolated by known techniques, e.g., density gradient centrifugation and identified by characteristic density banding. See, for example, Baker et al. (1991) Biophys. J. 60:1445-1456; and Hagensee et al. (1994) J. Virol. 68:4503-4505; Vincente, J Invertebr Pathol., 2011; Schneider-Ohrum and Ross, Curr. Top. Microbiol. Immunol., 354: 53073, 2012).

II. Sulfated HIV-1 Envelope Proteins and HIV-1 Neutralizing Peptides

As disclosed herein, the second variable loop (V2) of gp120 binds to the third variable loop (V3) loop through a highly conserved region that can adopt an α-helix conformation; and this binding event constrains the HIV-1 envelope in its native, antibody-shielded conformation. Sulfation of tyrosine residues at positions 173 and/or 177 of the gp120 V2 loop promotes stabilization of the V2-V3 interaction. Further, the V2 α-helix molecularly mimics the CCR5 N-terminal domain, which, similar to V2, binds to the conserved base of V3 and contains sulfated tyrosines that bolster the CCR5-V3 interaction. These discoveries led to the identification of new HIV-1 therapeutic peptides, as well as sulfated HIV-1 envelope proteins, fragments thereof containing gp120 positions 173 and/or 177, and methods of making and using such molecules.

The HIV-1 neutralizing peptides and sulfated HIV-1 envelope proteins and fragments thereof are useful to inhibit or treat HIV-1 infection, and/or induce an immunogenic response in vertebrate animals (such as mammals, for example primates, such as humans) to HIV-1. In several embodiments, the disclosed HIV-1 neutralizing peptides and sulfated HIV-1 envelope protein or immunogenic fragment thereof are immunogens.

The HIV-1 neutralizing peptides and sulfated HIV-1 envelope proteins and fragments thereof can include amino acid sequences from a HIV-1 envelope protein (e.g., gp160 or gp120) from an HIV-1 strain. HIV-1 can be classified into four groups: the "major" group M, the "outlier" group 0, group N, and group P. Within group M, there are several genetically distinct clades (or subtypes) of HIV-1. The disclosed HIV neutralizing peptides can be derived from any subtype of HIV, such as groups M, N, O, or P or clade A, B, C, D, F, G, H, J or K and the like. HIV envelope proteins from the different HIV clades, as well as nucleic acid sequences encoding such proteins and methods for the manipulation and insertion of such nucleic acid sequences into vectors, are known (see, e.g., HIV Sequence Compendium, Division of AIDS, National Institute of Allergy and Infectious Diseases (2013); HIV Sequence Database (hiv-weblanl.gov/content/hiv-db/mainpage.html); Sambrook et al., Molecular Cloning, a Laboratory Manual, 2d edition, Cold Spring Harbor Press, Cold Spring Harbor, N. Y. (1989); Ausubel et al., Current Protocols in Molecular Biology, Greene Publishing Associates and John Wiley & Sons, New York, N. Y. (1994)). Exemplary native HIV-1 envelope protein sequences are available in the HIV Sequence Database (hiv-web.lanl.gov/content/hiv-db/mainpage.html), further, Table 1 provides sequences for consensus HIV-1 envelope protein sequences.

TABLE 1 consensus gp160 sequences

| Consensus clade | Sequence |
|---|---|
| Consensus A1 | SEQ ID NO: 23 |
| Consensus A2 | SEQ ID NO: 24 |
| Consensus B | SEQ ID NO: 25 |
| Consensus C | SEQ ID NO: 26 |
| Consensus D | SEQ ID NO: 27 |
| Consensus F1 | SEQ ID NO: 28 |
| Consensus F2 | SEQ ID NO: 29 |

A. Sulfated HIV-1 Envelope Protein or Immunogenic Fragments Thereof

Sulfated HIV-1 envelope proteins and immunogenic fragments thereof are disclosed herein. The HIV-1 envelope proteins and fragments include a first sulfated tyrosine at position 173, a second sulfated tyrosine at position 177, or both a first sulfated tyrosine at position 173 and a second sulfated tyrosine at position 177 (HXB2 numbering). In several embodiments, the sulfated HIV-1 envelope proteins and fragments can be used to induce an immune response to HIV-1 in a subject.

The HIV-1 envelope protein can be selected from any HIV-1 envelope protein having a first sulfated tyrosine at position 173, a second sulfated tyrosine at position 177, or both a first sulfated tyrosine at position 173 and a second sulfated tyrosine at position 177. Examples include native HIV-1 envelope proteins (see, e.g., HIV Sequence Compendium, Division of AIDS, National Institute of Allergy and Infectious Diseases (2013); HIV Sequence Database (hiv-web.lanl.gov/content/hiv-db/mainpage.html), as well as engineered HIV-1 envelope proteins, for example HIV-1 envelope proteins engineered with stabilizing mutations such as introduced di-sulfide bonds deletion or addition of N-linked glycosylation sites, deletion or modification of the V1-V5 domains, deletion or modification of the outer or inner domain, or the bridging sheet, including stabilized soluble trimers that can be cleaved to adopt a near-native conformation. The person of skill in the art is familiar with HIV-1 envelope proteins and can readily determine if an HIV-1 envelope protein includes one or more tyrosine residues at positions 173 and 177. Exemplary HIV-1 envelope proteins include gp160, gp140, and gp120.

In some embodiments, the HIV envelope protein can be a native HIV-1 gp120 polypeptide sequence available in the HIV Sequence Database (hiv-web.lanl.gov/content/hiv-db/mainpage.html). In additional embodiments, the HIV-1 envelope protein can be a consensus HIV-1 envelope protein sequence from genetic subtype A-F set forth in Table 1. In some embodiments the HIV-1 envelope protein includes an amino acid sequence having at least 75% (for example at least 85%, 90%, 95%, 96%, 97%, 98% or 99%) sequence identity to a native HIV-1 gp120 polypeptide sequence, such a native HIV-1 gp120 polypeptide sequence available in the HIV Sequence Database (hiv-web.lanl.gov/content/hiv-db/mainpage.html) or to a consensus HIV-1 gp120 polypeptide sequence from genetic subtype A-F set forth in Table 1, wherein the HIV-1 envelope protein includes a first sulfated tyrosine at position 173, a second sulfated tyrosine at position 177, or both a first sulfated tyrosine at position 173 and a second sulfated tyrosine at position 177, and wherein the HIV-1 envelope protein can induce an immune response to HIV-1 in a subject.

The sulfated fragment of the HIV-1 envelope protein includes a first sulfated tyrosine at position 173, a second sulfated tyrosine at position 177, or both a first sulfated tyrosine at position 173 and a second sulfated tyrosine at position 177. In several embodiments, the sulfated fragment of the HIV-1 envelope protein includes or consists of at least 50 (such as at least 100, at least 150, at least 200, at least 250, at least 300, at least 350, at least 400, at least 450, at least 500, at least 550, at least 600, at least 650, at least 700, at least 750, or at least 800) consecutive amino acids of a native HIV-1 gp120 polypeptide sequence available in the HIV Sequence Database (hiv-web.lanl.gov/content/hiv-db/mainpage.html), or a consensus HIV-1 envelope protein sequence from genetic subtype A-F set forth in Table 1. In additional embodiments, the sulfated fragment of the HIV-1 envelope protein includes or consists of at least 50 (such as at least 100, at least 150, at least 200, at least 250, at least 300, at least 350, at least 400, at least 450, at least 500, at least 550, at least 600, at least 650, at least 700, at least 750, or at least 800) consecutive amino acids of an amino acid sequence having at least 75% (for example at least 85%, 90%, 95%, 96%, 97%, 98% or 99%) sequence identity to a native HIV-1 gp120 polypeptide sequence, such a native HIV-1 gp120 polypeptide sequence available in the HIV Sequence Database (hiv-weblanl.gov/content/hiv-db/mainpage.html) or to a consensus HIV-1 gp120 polypeptide sequence from genetic subtype A-F set forth in Table 1, wherein the HIV-1 envelope protein includes a first sulfated tyrosine at position 173, a second sulfated tyrosine at position 177, or both a first sulfated tyrosine at position 173 and a second sulfated tyrosine at position 177, and wherein the HIV-1 envelope protein can induce an immune response to HIV-1 in a subject.

In some embodiments, the sulfated HIV-1 envelope protein or immunogenic fragment thereof is a gp160, gp140, or gp120 protein that is sulfated on a first sulfated tyrosine at position 173, a second sulfated tyrosine at position 177, or both a first sulfated tyrosine at position 173 and a second sulfated tyrosine at position 177.

In some embodiments, the HIV-1 envelope protein or immunogenic fragment comprises gp120 positions 171-178 from the V2 loop, including the sulfated tyrosines at positions 173 and 177, and at least 30 consecutive amino acids from the V3 loop, including positions 297 to 335 of gp120 (HXB2 numbering).

In several embodiments, any of the sulfated HIV-1 envelope proteins and fragments thereof can be used to induce an immune response to HIV-1 in a subject. In several such embodiments, induction of the immune response includes production of broadly neutralizing antibodies to HIV-1. Methods to assay for neutralization activity are known to the person of ordinary skill in the art and are further described herein, and include, but are not limited to, a single-cycle infection assay as described in Martin et al. (2003) *Nature Biotechnology* 21:71-76. In this assay, the level of viral activity is measured via a selectable marker whose activity is reflective of the amount of viable virus in the sample, and the IC50 is determined. In other assays, acute infection can be monitored in the PM1 cell line or in primary cells (normal PBMC). In this assay, the level of viral activity can be monitored by determining the p24 concentrations using ELISA. See, for example, Martin et al. (2003) *Nature Biotechnology* 21:71-76. Additional neutralization assays are described in the disclosed examples.

Several embodiments include a multimer of any of the disclosed sulfated HIV envelope proteins or fragment thereof, for example, a multimer including 2, 3, 4, 5, 6, 7, 8, 9, or 10 or more of the disclosed sulfated HIV envelope proteins or fragment thereof. In several examples, any of the disclosed sulfated HIV envelope proteins or fragment thereof can be linked to another of the disclosed sulfated HIV envelope proteins or fragment thereof to form the multimer.

In some embodiments, the sulfated HIV envelope proteins or fragment thereof is linked to a heterologous protein derived from another protein of human, animal, vegetal or synthetic origin, which serves to either stabilize its structure, increase its potency, or improve its pharmacological properties such as plasma half-life or resistance to protease digestion. Examples of heterologous proteins include (but are not limited to) tetanus toxoid, cholera toxin beta-subunit, albumin, or the Fc portion of human immunoglobulin (Ig)G or IgM.

In some embodiments, the HIV-1 envelope protein or immunogenic fragment comprises the sulfated tyrosine residues at gp120 positions 173, 177, or 173 and 177, and further comprises the V3 loop or a fragment thereof engrafted into a heterologous protein or protein fragment to form a chimeric protein containing elements from both V2 and V3 capable of recreating the native complex between these two regions.

In some embodiments, the HIV-1 envelope protein or immunogenic fragment comprises two sulfated tyrosine residues inserted in a heterologous protein sequence such as, for example, the sequence of the N-terminal domain of CCR5, which replaces the sequence of the V2 region within the context of gp120, gp140 or gp160.

In some embodiments, the sulfated HIV envelope proteins or fragment thereof can be covalently linked to a carrier, which is an immunogenic macromolecule. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

It is understood in the art that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering techniques known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety. Thus, in additional embodiments, the sulfated HIV envelope proteins or fragment thereof can include one or more amino acid substitutions compared to the native gp120 sequence. For example, in some embodiments, the sulfated HIV envelope proteins or fragment thereof includes up to 20 amino acid substitutions compared to the native gp120 polypeptide sequence, such as native HIV-1 gp120 polypeptide sequence available in the HIV Sequence Database (hiv-weblanl.gov/content/hiv-db/mainpage.html), or a consensus HIV-1 gp120 polypeptide sequence from genetic subtype A-F set forth in Table 1, wherein the sulfated HIV envelope proteins or fragment thereof includes a first sulfated tyrosine at position 173, a second sulfated tyrosine at position 177, or both a first sulfated tyrosine at position 173 and a second sulfated tyrosine at position 177. Alternatively, the sulfated HIV envelope proteins or fragment thereof can have none, or up to 1, 2, 3, 4, 5, 6, 7, 8, 9, 10, 11, 12, 13, 14, 15, 16, 17, 18 or 19 amino acid substitutions compared to the native gp120 polypeptide sequence, wherein the peptide includes a first sulfated tyrosine at position 173, a second sulfated tyrosine at position 177, or both a first sulfated tyrosine at position 173 and a second sulfated tyrosine at position 177, and wherein the peptide is neutralizing. Manipulation of the nucleotide sequence encoding the sulfated HIV envelope proteins or fragment thereof using standard procedures, including in one specific, non-limiting, embodiment, site-directed mutagenesis or in another specific, non-limiting, embodiment, PCR, can be used to produce such variants. Alternatively, the sulfated HIV envelope proteins or fragment thereof can be synthesized using standard methods. The simplest modifications involve the substitution of one or more amino acids for amino acids having similar biochemical properties. These so-called conservative substitutions are likely to have minimal impact on the activity of the resultant protein.

Methods of making the sulfated HIV-1 envelope proteins and fragments thereof are also provided. For example, recombinant DNA technology can be used to generate a nucleic acid encoding the disclosed proteins, from which the protein can be expressed, sulfated, and purified. Proteins can also by synthesized in vitro, and sulfated and purified. Methods of generating a protein with one or more sulfated tyrosine residues are known to the person of ordinary skill in the art, and described herein (see, e.g., U.S. Pat. No. 5,541,095, U.S. Pub. No. 2009/0042738, 2006/0009631, 2003/0170849, 2006/0115859, Liu et al., Mol. Biosyst., 7:38-47, 2011, and Choe and Farzan, Methods in Enzymology, 461: 147-170, 2009) each of which is incorporated by reference herein).

In some embodiments, the methods include providing a plurality of HIV-1 envelope proteins or immunogenic fragments thereof comprising tyrosine residues at gp120 positions 173, 177, or 173 and 177, and sulfating the tyrosine residues on at least 90% of the HIV-1 envelope proteins or immunogenic fragments in the plurality of HIV-1 envelope proteins or immunogenic fragments. Methods of making proteins with sulfated tyrosine residues are known; see for example Choe and Farzan, Methods in Enzymology, 461: 147-170, 2009, incorporated by reference in its entirety).

In some embodiments, a first heterologous nucleic acid molecule encoding a HIV-1 envelope protein or immunogenic fragment thereof comprising tyrosine residues at gp120 positions 173, 177, or 173 and 177, is expressed in a cell to produce the plurality of HIV-1 envelope proteins or immunogenic fragments. The expression conditions can be such that the tyrosine residues at gp120 positions 173, 177, or 173 and 177, are sulfated on at least 80% (such as at least 85%, at least 90%, at least 95%, or at least 98%) of the HIV-1 envelope proteins or immunogenic fragments expressed in the cell line. For example, the cell selected for expression can be a cell that has a high level of tyrosine sulfase activity. In some embodiments, the cell is an immortalized cell that has a high level of tyrosine sulfase activity. In some embodiments, the cell is an immortalized T cell or an immortalized B cell. In some embodiments, a second nucleic acid molecule encoding a tyrosine sulfotransferase can be co-expressed in the cell line to provide the desired tyrosine sulfation activity.

In some embodiments, the sulfated HIV-1 envelope protein or immunogenic fragment thereof is made by incubating an HIV-1 envelope protein or immunogenic fragment thereof including gp120 positions 173, 177, or 173 and 177 with a purified tyrosine sulfotransferase under conditions sufficient for tyrosine sulfation of gp120 positions 173, 177, or 173 and 177. Conditions sufficient for tyrosine sulfation are known, and includes those described, for example, in Example 1.

Nucleic acid and protein sequence of tyrosine sulfotransferases are known. For example, the sequences of human TPST1 (NCBI Ref. Seqs. NP_003587.1 (Protein, SEQ ID NO: 30) and NM_003596.3 (DNA, SEQ ID NO: 31), mouse TPST1 (NCBI Ref. Seqs. NP_001123948.1 (Protein, SEQ ID NO: 32) and NM_001130476.2 (DNA, SEQ ID NO: 33)), human TPST2, variant 1 (NCBI Ref. Seqs. NP_001008566.1 (Protein, SEQ ID NO: 34) and NM_001008566.1 (DNA, SEQ ID NO: 35)), human TPST2, variant 2 (NCBI Ref. Seqs. NP_003586.3 (Protein, SEQ ID NO: 36) and NM_003595.3 (DNA, SEQ ID NO: 37)), and mouse TPST2 Human TPST2, variant 2 (NCBI Ref. Seqs. NP_033445.2 (Protein, SEQ ID NO: 38) and NM_009419.3 (DNA, SEQ ID NO: 39)) are available from public databases. All the NCBI Reference Nos. listed above are incorporated by reference herein in their entirety as present in the database on Dec. 6, 2013. Variants of tyrosine sulfotransferases can also be used. For example, a fragment of a known TPST having tyrosine sulfation activity, a TPST or fragment thereof with one or more amino acid substitutions or deletions that has tyrosine sulfation activity, or a synthetic protein derived from a TPST protein that has tyrosine sulfation activity.

Methods of determining the sulfation status of a protein are known and examples are described herein, including use of a sulfo-tyrosine specific antibody and the metabolic incorporation of radioactive free sulfate into the nascent protein, which is subsequently revealed by autoradiography. In several embodiments, the disclosed methods of making a sulfated HIV-1 envelope protein or immunogenic fragment thereof include purifying the sulfated HIV-1 envelope proteins or fragment. Methods of purifying a protein are known, and also described herein.

Additional methods for determining the sulfation status of gp120 include mass spectrometry analysis of protein fragments.

B. HIV Neutralizing peptides

Isolated HIV-1 neutralizing peptides are disclosed herein including or consisting of an amino acid sequence including gp120 positions 171-178 (HXB2 numbering), wherein the amino acid sequence has up to four amino acid substitutions, and wherein the peptide is neutralizing. In additional embodiments, the HIV-1 neutralizing peptides include or consist of an amino acid sequence of gp120 positions 168-185 (HXB2 numbering), wherein the amino acid sequence has up to four amino acid substitutions, and wherein the peptide is neutralizing. In several embodiments, the peptide further includes a first sulfated tyrosine at position 173, a second sulfated tyrosine at position 177, or both a first sulfated tyrosine at position 173 and a second sulfated tyrosine at position 177.

In several embodiments, the HIV neutralizing peptide includes or consists of at least 8 consecutive amino acids (such as at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or at least 100 consecutive amino acids) from a native HIV-1 gp120 polypeptide sequence available in the HIV Sequence Database (hiv-weblanl.gov/content/hiv-db/mainpage.html), for example, a consensus HIV-1 gp120 polypeptide sequence from genetic subtype A-F set forth in Table 1, including any polypeptide sequences having at least 75% (for example at least 85%, 90%, 95%, 96%, 97%, 98% or 99%) sequence identity to a native HIV-1 gp120 polypeptide sequence, such a native HIV-1 gp120 polypeptide sequence available in the HIV Sequence Database (hiv-weblanl.gov/content/hiv-db/mainpage.html), for example, a consensus HIV-1 gp120 polypeptide sequence from genetic subtype A-F set forth in Table 1, wherein the peptide includes a first sulfated tyrosine at position 173, a second sulfated tyrosine at position 177, or both a first sulfated tyrosine at position 173 and a second sulfated tyrosine at position 177, and wherein the peptide is neutralizing.

For example, in some embodiments, the HIV neutralizing peptide includes or consists of 8-100 consecutive amino acids (such as 8-9, 8-10, 8-11, 8-12, 8-13, 8-14, 8-15, 8-16, 8-17, 8-18, 8-19, 8-20, 8-25, 8-30, 8-35, 8-40, 8-45, 8-50, 8-60, 8-70, 8-80, 8-90, 8-10, 10-15, 10-20, 10-30, 10-40, 10-50, 16-18, 16-19, 16-20, 16-25, 17-18, 17-19, 17-20, 17-25, 18-19, 18-20, 18-21, 18-22, 18-23, 18-25, 18-30, 18-35, 18-40, 18-45, 18-50, 18-60, 18-70, 18-80, 18-90, 18-100, 20-21, 20-22, 20-23, 20-24, 20-25, 20-30, 20-40, or 20-50 consecutive amino acids) from a native HIV-1 gp120 polypeptide sequence, such as a native HIV-1 gp120 polypeptide sequence available in the HIV Sequence Database (hiv-weblanl.gov/content/hiv-db/mainpage.html), for example, a consensus HIV-1 gp120 polypeptide sequence from genetic subtype A-F set forth in Table 1, or any polypeptide sequences having at least 75% (for example at least 85%, 90%, 95%, 96%, 97%, 98% or 99%) sequence identity to a native HIV-1 gp120 polypeptide sequence, such as a native HIV-1 gp120 polypeptide sequence available in the HIV Sequence Database (hiv-weblanl.gov/content/hiv-db/mainpage.html), for example, a consensus HIV-1 gp120 polypeptide sequence from genetic subtype A-F set forth in Table 1, wherein the peptide includes a first sulfated tyrosine at position 173, a second sulfated tyrosine at position 177, or both a first sulfated tyrosine at position 173 and a second sulfated tyrosine at position 177, and wherein the peptide is neutralizing.

In some embodiments, the HIV neutralizing peptide is also of a maximum length, for example no more than 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids amino acids in length. The HIV neutralizing peptide may include, consist or consist essentially of the disclosed sequences. The disclosed contiguous sequences may also be joined at either end to other unrelated sequences (for example, non-gp120, non-HIV-1, non-viral envelope, or non-viral protein sequences).

It is understood in the art that some variations can be made in the amino acid sequence of a protein without affecting the activity of the protein. Such variations include insertion of amino acid residues, deletions of amino acid residues, and substitutions of amino acid residues. These variations in sequence can be naturally occurring variations or they can be engineered through the use of genetic engineering techniques known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp. 9.31-9.57), or in Current Protocols in Molecular Biology, John Wiley & Sons, N.Y. (1989), 6.3.1-6.3.6, both of which are incorporated herein by reference in their entirety. Thus, in additional embodiments, the HIV neutralizing peptide includes one or more amino acid substitutions compared to the native gp120 sequence. For example, in some embodiments, the HIV neutralizing peptide includes up to 20 amino acid substitutions compared to the native gp120 polypeptide sequence, such as native HIV-1 gp120 polypeptide sequence available in the HIV Sequence Database (hiv-weblanl.gov/content/hiv-db/main-page.html), for example, a consensus HIV-1 gp120 polypeptide sequence from genetic subtype A-F set forth in Table 1, wherein the peptide includes a first sulfated tyrosine at position 173, a second sulfated tyrosine at position 177, or both a first sulfated tyrosine at position 173 and a second sulfated tyrosine at position 177, and wherein the peptide is neutralizing. Alternatively, the peptide can have none, or up to 1, 2, 3, 4, 5, 6, 7, 8, 9, 10, 11, 12, 13, 14, 15, 16, 17, 18 or 19 amino acid substitutions compared to the native gp120 polypeptide sequence, wherein the peptide includes a first sulfated tyrosine at position 173, a second sulfated tyrosine at position 177, or both a first sulfated tyrosine at position 173 and a second sulfated tyrosine at position 177, and wherein the peptide is neutralizing. Manipulation of the nucleotide sequence encoding the HIV neutralizing peptide using standard procedures, including in one specific, non-limiting, embodiment, site-directed mutagenesis or in another specific, non-limiting, embodiment, PCR, can be used to produce such variants. Alternatively, the HIV neutralizing peptide can be synthesized using standard methods. The simplest modifications involve the substitution of one or more amino acids for amino acids having similar biochemical properties. These so-called conservative substitutions are likely to have minimal impact on the activity of the resultant protein.

In some embodiments, the HIV neutralizing peptide includes or consists of gp120 positions 171-178, wherein the HIV neutralizing peptide includes the amino acid sequence set forth as $KX_1YX_2LFYX_3$ (SEQ ID NO: 2), wherein $X_1$ is E or V, $X_2$ is A or S, and $X_3$ is E, K or R. In some examples, the HIV neutralizing peptide includes or consists of an amino acid sequence set forth as KEYALFYE (SEQ ID NO: 3; HIV-1 Bal); KEYALFYK (SEQ ID NO: 4; Clade B); KVYSLFYR (SEQ ID NO: 5; Clade A); or KEYALFYR (SEQ ID NO: 6; Clade C).

In additional embodiments, the HIV neutralizing peptide includes or consists of gp120 positions 168-185, wherein the HIV neutralizing peptide includes or consists of an amino acid sequence set forth as $KX_1X_2X_3X_4X_5X_6LFYX_7LDX_8VX_9IX_{10}$ (SEQ ID NO: 7); wherein $X_1$ is V or K, $X_2$ is Q or K, $X_3$ is K or Q, $X_4$ is E or V, $X_5$ is Y or H, $X_6$ is A or S, $X_7$ is E or K, or R, $X_8$ is I or V, $X_9$ is P or Q, and $X_{10}$ is D or N. In some examples, the HIV neutralizing peptide includes or consists of the amino acid sequence set forth as KVQKEYALFYELDIVPID (SEQ ID NO: 8; HIV-1 Bal); KKQKVYSLFYRLDVVQIN (SEQ ID NO: 10; Clade A); KVQKEYALFYKLDVVPID (SEQ ID NO: 9; Clade B); KKKKEYALFYRLDIVPLN (SEQ ID NO: 11; Clade C); KKKQVHALFYKLDVVQID (SEQ ID NO: 12; Clade D); KKQKVHALFYKLDIVQIE (SEQ ID NO: 13; Clade E); or KKKKVHALFYRLDIVPIN (SEQ ID NO: 14; Clade F).

In several embodiments, the disclosed HIV neutralizing peptides are sulfated. For example, HIV neutralizing peptides including tyrosine residues at gp120 positions 173, 177, or both positions 173 and 177 can be sulfated at these positions. Methods of making sulfated peptides are disclosed herein and are familiar to the person of ordinary skill in the art. For example, methods of generating a peptide with one or more sulfated tyrosine residues are known to the person of ordinary skill in the art, and described herein (see, e.g., WO2001/064710, U.S. Pat. No. 5,541,095, U.S. Pub. No. 2009/0042738, 2006/0009631, 2003/0170849, 2006/0115859, and Liu et al., Mol. Biosyst., 7:38-47, 2011, Choe and Farzan, Methods in Enzymology, 461: 147-170, 2009, each of which is incorporated by reference herein).

Several embodiments include a multimer of any of the disclosed HIV neutralizing peptides, for example, a multimer including 2, 3, 4, 5, 6, 7, 8, 9, or 10 or more of the disclosed HIV neutralizing peptides. In several examples, any of the disclosed HIV neutralizing peptides can be linked to another of the disclosed HIV neutralizing peptides to form the multimer.

In some embodiments, the HIV-neutralizing peptide is linked to a heterologous scaffold derived from another protein of human, animal, vegetal or synthetic origin, which serves to either stabilize its structure, increase its potency, or improve its pharmacological properties such as plasma half-life or resistance to protease digestion. In other examples a single scaffold can bind multiple copies of the neutralizing peptide. Examples of scaffold proteins include (but are not limited to) tetanus toxoid, cholera toxin beta-subunit, albumin, or the Fc portion of human immunoglobulin (Ig)G or IgM.

In several embodiments, the disclosed HIV neutralizing peptides bind to gp120. In several examples, the dissociation constant for gp120 binding to the HIV neutralizing peptide, is less than about $10^{-4}$ Molar, such as less than about $10^{-5}$ Molar, $10^{-6}$ Molar, $10^{-7}$ Molar, or less than $10^{-8}$ Molar. Binding to gp120 can be determined by methods known in the art. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

In several embodiments, the disclosed HIV neutralizing peptides bind to CD4. In several examples, the dissociation constant for CD4 binding to the HIV neutralizing peptide, is less than about $10^{-4}$ Molar, such as less than about $10^{-5}$ Molar, $10^{-6}$ Molar, $10^{-7}$ Molar, or less than $10^{-8}$ Molar. Binding to CD4 can be determined by methods known in the art. The determination that a particular agent binds substantially only to a specific polypeptide may readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

In additional embodiments, the HIV neutralizing peptides compete for binding to gp120 with monoclonal antibody 412d. In some examples, the HIV neutralizing peptides compete for binding to the V3 loop of gp120 with monoclonal antibody 412d. Methods of determining if a HIV neutralizing peptide compete with monoclonal antibody 412d for binding to gp120 are known to the person of ordinary skill in the art and disclosed herein (see Example 1). In further embodiments, the HIV neutralizing peptides compete for binding to gp120 with monoclonal antibody E51. Antibody E51 and its binding to gp120 is familiar to the person of ordinary skill in the art (see, e.g., Xiang et al. *Virology*, 315:124-34, 2003). Methods of determining if a HIV neutralizing peptide compete with monoclonal antibody E51 for binding to gp120 are known to the person of ordinary skill in the art.

In additional embodiments, the HIV neutralizing peptides compete for binding to gp120 with CCR5. In some examples, the HIV neutralizing peptides compete for binding to the V3 loop of gp120 with CCR5. Methods of determining if a HIV neutralizing peptide competes with CCR5 for binding to gp120 are known to the person of ordinary skill in the art and disclosed herein (see Example 1).

In several embodiments, the HIV neutralizing peptides include an alpha helical structure. For example, gp120 positions 171-178 of the HIV neutralizing peptide include an alpha helical structure. Methods of determining if a peptide includes an alpha helical structure are known to the person of ordinary skill in the art and are further disclosed herein. In one example, circular dichroism measurements are used to determine if a peptide includes an alpha helical structure.

In some embodiments, the sulfated HIV neutralizing peptides can be covalently linked to a carrier, which is an immunogenic macromolecule. When bound to a carrier, the bound polypeptide becomes more immunogenic. Carriers are chosen to increase the immunogenicity of the bound molecule and/or to elicit higher titers of antibodies against the carrier which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as hepatitis B surface antigen and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

Standard methods in the art can be used to make the disclosed peptides. For example, recombinant DNA technology can be used to generate a nucleic acid encoding the disclosed peptides, and from which the peptide can be expressed and purified. Such methods are known to the skilled artisan and further described herein. In addition to recombinant methods, the peptides that are disclosed herein can also be constructed in whole or in part using standard peptide synthesis. Solid phase synthesis of the peptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2: Special Methods in Peptide Synthesis*, Part A. pp. 3-284; Merrifield et al., *J. Am. Chem. Soc.* 85:2149-2156, 1963, and Stewart et al., *Solid Phase Peptide Synthesis*, 2nd ed., Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art. Methods of generating a peptide with one or more sulfated tyrosine residues are known to the person of ordinary skill in the art, and described herein (see, e.g., U.S. Pat. No. 5,541,095, U.S. Pub. No. 2009/0042738, 2006/0009631, 2003/0170849, 2006/0115859, and Liu et al., *Mol. Biosyst.*, 7:38-47, 2011, each of which is incorporated by reference herein).

Some embodiments include a mixture of peptides from the V2 and V3 loop of gp120, which can reciprocally bind recreating the molecular complex of V2 and V3 that occurs within the native gp120 protein and thereby can be used to induce an immune response against the V2-V3 complex, for example, to inhibit or prevent HIV infection. Peptides from the V2 loop are disclosed herein and can include the HIV-1 neutralizing peptides disclosed in this section. In some embodiments, the V3 loop peptide includes positions 296 to 331 (such as positions 290-336) according to gp120 HXB2 numbering (GENBANK® Accession No. K03455, incorporated by reference herein as present in the database on Jul. 27, 2012). In several embodiments, the V3 loop peptide includes or consists of at least 30 consecutive amino acids (such as at least 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or at least 100 consecutive amino acids) from a V3 loop native HIV-1 gp120 polypeptide sequence available in the HIV Sequence Database (hiv-weblanl.gov/content/hiv-db/mainpage.html), for example, a consensus HIV-1 gp120 polypeptide sequence from genetic subtype A-F set forth in Table 1, including any polypeptide sequences having at least 75% (for example at least 85%, 90%, 95%, 96%, 97%, 98% or 99%) sequence identity to a native HIV-1 gp120 polypeptide sequence, such a native HIV-1 gp120 polypeptide sequence available in the HIV Sequence Database (hiv-web.lanl.gov/content/hiv-db/mainpage.html), for example, a consensus HIV-1 gp120 polypeptide sequence from genetic subtype A-F set forth in Table 1. In some embodiments, the V3 loop peptide is also of a maximum length, for example no more than 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids amino acids in length. In some embodiments, V2 and V3 loop peptides are engrafted onto the surface of a scaffold molecule, in a location that allows the two peptides to bind to each other and recreate the native V2-V3 complex.

In some embodiments, the V3 loop peptide described in the prior paragraph can be linked to a heterologous protein (such as a carrier protein) that is also linked to the V2 loop peptide. The V2 and V3 loop peptides are linked to the heterologous protein in such a way as to allow binding of the two peptides to recreating the molecular complex of V2 and V3 that occurs within the native gp120 protein. In several embodiments, the V3 loop peptide linked to the heterologous protein that is linked to the V2 loop peptide can be used to induce an immune response against the V2-V3 complex, for example, to inhibit or prevent HIV infection.

III. Protein Nanoparticles

In some embodiments a protein nanoparticle is provided that includes one or more HIV-1 neutralizing peptides or sulfated HIV-1 envelope proteins or immunogenic fragments thereof. Non-limiting example of nanoparticles include ferritin nanoparticles, an encapsulin nanoparticles, Sulfur Oxygenase Reductase (SOR) nanoparticles, and lumazine synthase nanoparticles, which are comprised of an assembly of monomeric subunits including ferritin proteins, encapsulin proteins, SOR proteins, and lumazine synthase respectively. To construct protein nanoparticles including a HIV-1 neutralizing peptide or sulfated HIV-1 envelope protein or immunogenic fragment thereof, the HIV-1 neutralizing peptide or sulfated HIV-1 envelope protein or immunogenic fragment thereof is linked to a subunit of the protein nanoparticle (such as a ferritin protein, an encapsulin protein, a SOR protein, or a lumazine synthase protein). The fusion protein self-assembles into a nanoparticle under appropriate conditions.

In some embodiments, any of the disclosed HIV-1 neutralizing peptides or sulfated HIV-1 envelope proteins or immunogenic fragments thereof are linked to a ferritin polypeptide to construct a ferritin nanoparticle. Ferritin nanoparticles and their use for immunization purposes (e.g., for immunization against influenza antigens) has been disclosed in the art (see, e.g., Kanekiyo et al., Nature, 499:102-106, 2013, incorporated by reference herein in its entirety). Ferritin is a globular protein that is found in all animals, bacteria, and plants, and which acts primarily to control the rate and location of polynuclear $Fe(III)_2O_3$ formation through the transportation of hydrated iron ions and protons to and from a mineralized core. The globular form of ferritin is made up of monomeric subunits, which are polypeptides having a molecule weight of approximately 17-20 kDa. An example of the sequence of one such monomeric subunit is represented by SEQ ID NO: 40.

Each monomeric subunit has the topology of a helix bundle which includes a four antiparallel helix motif, with a fifth shorter helix (the C-terminal helix) lying roughly perpendicular to the long axis of the 4 helix bundle. According to convention, the helices are labeled 'A, B, C, D & E' from the N-terminus respectively. The N-terminal sequence lies adjacent to the capsid three-fold axis and extends to the surface, while the E helices pack together at the four-fold axis with the C-terminus extending into the capsid core. The consequence of this packing creates two pores on the capsid surface. It is expected that one or both of these pores represent the point by which the hydrated iron diffuses into and out of the capsid. Following production, these monomeric subunit proteins self-assemble into the globular ferritin protein. Thus, the globular form of ferritin comprises 24 monomeric, subunit proteins, and has a capsid-like structure having 432 symmetry. Methods of constructing ferritin nanoparticles are known to the person of ordinary skill in the art and are further described herein (see, e.g., Zhang, Int. J. Mol. Sci., 12:5406-5421, 2011, which is incorporated herein by reference in its entirety).

In specific examples, the ferritin polypeptide is *E. coli* ferritin, *Helicobacter pylori* ferritin, human light chain ferritin, bullfrog ferritin or a hybrid thereof, such as *E. coli*-human hybrid ferritin, *E. coli*-bullfrog hybrid ferritin, or human-bullfrog hybrid ferritin. Exemplary amino acid sequences of ferritin polypeptides and nucleic acid sequences encoding ferritin polypeptides for use to make a ferritin nanoparticle including HIV-1 neutralizing peptide or sulfated HIV-1 envelope protein or immunogenic fragment thereof can be found in GENBANK®, for example at accession numbers ZP_03085328, ZP_06990637, EJB64322.1, AAA35832, NP_000137 AAA49532, AAA49525, AAA49524 and AAA49523, which are specifically incorporated by reference herein in their entirety as available Dec. 6, 2013. In one embodiment, any of the disclosed HIV-1 neutralizing peptides or sulfated HIV-1 envelope proteins or immunogenic fragments thereof is linked to a ferritin protein including an amino acid sequence at least 80% (such as at least 85%, at least 90%, at least 95%, or at least 97%) identical to amino acid sequence set forth as SEQ ID NO: 40.

In additional embodiments, any of the disclosed HIV-1 neutralizing peptides or sulfated HIV-1 envelope proteins or immunogenic fragments thereof are linked to an lumazine synthase polypeptide to construct a lumazine synthase nanoparticle. In some embodiments, the lumazine synthase nanoparticle includes a disclosed HIV-1 neutralizing peptides or sulfated HIV-1 envelope proteins or immunogenic fragments thereof linked to a lumazine synthase protein, such as a lumazine synthase protein including the amino acid sequence set forth as SEQ ID NO: 41.

In additional embodiments, any of the disclosed HIV-1 neutralizing peptides or sulfated HIV-1 envelope proteins or immunogenic fragments thereof are linked to an encapsulin polypeptide to construct an encapsulin nanoparticle. In some embodiments, the encapsulin nanoparticle includes a disclosed HIV-1 neutralizing peptides or sulfated HIV-1 envelope proteins or immunogenic fragments thereof linked to a encapsulin protein, such as a encapsulin protein including the amino acid sequence set forth as SEQ ID NO: 42.

Encapsulin proteins are a conserved family of bacterial proteins also known as linocin-like proteins that form large protein assemblies that function as a minimal compartment to package enzymes. The encapsulin assembly is made up of monomeric subunits, which are polypeptides having a molecule weight of approximately 30 kDa. Following production, the monomeric subunits self-assemble into the globular encapsulin assembly including 60 monomeric subunits. Methods of constructing encapsulin nanoparticles are known to the person of ordinary skill in the art, and further described herein (see, for example, Sutter et al., Nature Struct. and Mol. Biol., 15:939-947, 2008, which is incorporated by reference herein in its entirety). In specific examples, the encapsulin polypeptide is bacterial encapsulin, such as *E. coli* or *Thermotoga maritime* encapsulin.

In additional embodiments, any of the disclosed HIV-1 neutralizing peptides or sulfated HIV-1 envelope proteins or immunogenic fragments thereof are linked to a Sulfur Oxygenase Reductase (SOR) polypeptide to construct a SOR nanoparticle. In some embodiments, the SOR nanoparticle includes a disclosed HIV-1 neutralizing peptides or sulfated HIV-1 envelope proteins or immunogenic fragments thereof linked to a SOR protein, such as a SOR protein including the amino acid sequence set forth as SEQ ID NO: 43.

SOR proteins are microbial proteins (for example from the thermoacidophilic archaeon *Acidianus ambivalens* that form 24 subunit protein assemblies). Methods of constructing SOR nanoparticles are known to the person of ordinary skill in the art (see, e.g., Urich et al., Science, 311:996-1000, 2006, which is incorporated by reference herein in its entirety). An example of an amino acid sequence of a SOR protein for use to make SOR nanoparticles is set forth in Urich et al., Science, 311:996-1000, 2006, which is incorporated by reference herein in its entirety.

In some examples, any of the disclosed HIV-1 neutralizing peptides or sulfated HIV-1 envelope proteins or immunogenic fragments thereof is linked to the N- or C-terminus, or placed within an internal loop of a ferritin, encapsulin, SOR, or lumazine synthase protein, for example with a linker, such as a Ser-Gly linker. When the constructs have been made in HEK 293 Freestyle cells, the fusion proteins are secreted from the cells and self-assembled into nanoparticles. The nanoparticles can be purified using known techniques, for example by a few different chromatography procedures, e.g. Mono Q (anion exchange) followed by size exclusion (SUPEROSE® 6) chromatography.

Several embodiments include a monomeric subunit of a ferritin, encapsulin, SOR, or lumazine synthase protein, or any portion thereof which is capable of directing self-assembly of monomeric subunits into the globular form of the protein Amino acid sequences from monomeric subunits of any known ferritin, encapsulin, SOR, or lumazine synthase protein can be used to produce fusion proteins with the disclosed HIV-1 neutralizing peptides or sulfated HIV-1 envelope proteins or immunogenic fragments thereof, so long as the monomeric subunit is capable of self-assembling into a nanoparticle displaying the HIV-1 neutralizing peptides or sulfated HIV-1 envelope proteins or immunogenic fragments thereof on its surface.

The fusion proteins need not comprise the full-length sequence of a monomeric subunit polypeptide of a ferritin, encapsulin, SOR, or lumazine synthase protein. Portions, or regions, of the monomeric subunit polypeptide can be utilized so long as the portion comprises amino acid sequences that direct self-assembly of monomeric subunits into the globular form of the protein.

In some embodiments, it may be useful to engineer mutations into the amino acid sequence of the monomeric ferritin, encapsulin, SOR, or lumazine synthase subunits. For example, it may be useful to alter sites such as enzyme recognition sites or glycosylation sites in order to give the fusion protein beneficial properties (e.g., half-life).

It will be understood by those skilled in the art that fusion of any of the disclosed HIV-1 neutralizing peptides or sulfated HIV-1 envelope proteins or immunogenic fragments thereof to the ferritin, encapsulin, SOR, or lumazine synthase protein should be done such that the disclosed HIV-1 neutralizing peptides or sulfated HIV-1 envelope proteins or immunogenic fragments thereof portion of the fusion protein does not interfere with self-assembly of the monomeric ferritin, encapsulin, SOR, or lumazine synthase subunits into the globular protein, and that the ferritin, encapsulin, SOR, or lumazine synthase protein portion of the fusion protein does not interfere with the ability of the disclosed HIV-1 neutralizing peptides or sulfated HIV-1 envelope proteins or immunogenic fragments thereof to elicit an immune response to HIV. In some embodiments, the ferritin, encapsulin, SOR, or lumazine synthase protein and disclosed HIV-1 neutralizing peptides or sulfated HIV-1 envelope proteins or immunogenic fragments thereof can be joined together directly without affecting the activity of either portion. In other embodiments, the ferritin, encapsulin, SOR, or lumazine synthase protein and the HIV-1 neutralizing peptides or sulfated HIV-1 envelope proteins or immunogenic fragments thereof are joined using a linker (also referred to as a spacer) sequence. The linker sequence is designed to position the ferritin, encapsulin, SOR, or lumazine synthase portion of the fusion protein and the disclosed HIV-1 neutralizing peptides or sulfated HIV-1 envelope proteins or immunogenic fragments thereof portion of the fusion protein, with regard to one another, such that the fusion protein maintains the ability to assemble into nanoparticles, and also elicit an immune response to HIV. In several embodiments, the linker sequences comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. One example of such a linker sequence is SGG Amino acids can be added or subtracted as needed. Those skilled in the art are capable of determining appropriate linker sequences for construction of protein nanoparticles.

The disclosed HIV-1 neutralizing peptides or sulfated HIV-1 envelope proteins or immunogenic fragments thereof linked to ferritin, encapsulin, SOR, or lumazine synthase proteins can self-assemble into multi-subunit protein nanoparticles, termed ferritin nanoparticles, encapsulin nanoparticles, SOR nanoparticles, and lumazine synthase nanoparticles, respectively. The nanoparticles including the disclosed HIV-1 neutralizing peptides or sulfated HIV-1 envelope proteins or immunogenic fragments thereof have substantially the same structural characteristics as the native ferritin, encapsulin, SOR, or lumazine synthase nanoparticles that do not include the disclosed HIV-1 neutralizing peptides or sulfated HIV-1 envelope proteins or immunogenic fragments thereof. That is, they contain 24, 60, 24, or 60 subunits (respectively) and have similar corresponding symmetry.

IV. Virus-Like Particles

In some embodiments, a virus-like particle (VLP) is provided that includes HIV-1 neutralizing peptides or sulfated HIV-1 envelope proteins or immunogenic fragments thereof. VLPs lack the viral components that are required for virus replication and thus represent a highly attenuated form of a virus. The VLP can display a polypeptide (e.g., HIV-1 neutralizing peptides or sulfated HIV-1 envelope proteins or immunogenic fragments thereof) that is capable of eliciting an immune response to HIV when administered to a subject. Virus like particles and methods of their production are known and familiar to the person of ordinary skill in the art, and viral proteins from several viruses are known to form VLPs, including human papillomavirus, HIV (Kang et al., Biol. Chem. 380: 353-64 (1999)), Semliki-Forest virus (Notka et al., Biol. Chem. 380: 341-52 (1999)), human polyomavirus (Goldmann et al., J. Virol. 73: 4465-9 (1999)), rotavirus (Jiang et al., Vaccine 17: 1005-13 (1999)), parvovirus (Casal, Biotechnology and Applied Biochemistry, Vol 29, Part 2, pp 141-150 (1999)), canine parvovirus (Hurtado et al., J. Virol. 70: 5422-9 (1996)), hepatitis E virus (Li et al., J. Virol. 71: 7207-13 (1997)), and Newcastle disease virus. The formation of such VLPs can be detected by any suitable technique. Examples of suitable techniques known in the art for detection of VLPs in a medium include, e.g., electron microscopy techniques, dynamic light scattering (DLS), selective chromatographic separation (e.g., ion exchange, hydrophobic interaction, and/or size exclusion chromatographic separation of the VLPs) and density gradient centrifugation.

V. Polynucleotides

Polynucleotides encoding the HIV-1 neutralizing peptides or HIV-1 envelope proteins or immunogenic fragments are also provided. For example a nucleic acid molecule encoding a HIV-1 envelope protein or immunogenic fragment thereof can be expressed in a cell to make a sulfated HIV-1 envelope protein or immunogenic fragment thereof. These polynucleotides include DNA, cDNA and RNA sequences which encode the antigen.

Methods for the manipulation and insertion of the nucleic acids of this disclosure into vectors are well known in the art (see for example, Sambrook et al., *Molecular Cloning, a Laboratory Manual,* 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994).

A nucleic acid encoding an antigen can be cloned or amplified by in vitro methods, such as the polymerase chain reaction (PCR), the ligase chain reaction (LCR), the transcription-based amplification system (TAS), the self-sustained sequence replication system (3SR) and the Qβ replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., *Cold Spring Harbor Symp. Quant. Biol.* 51:263, 1987; and Erlich, ed., *PCR Technology*, (Stockton Press, NY, 1989). Polynucleotides also can be isolated by screening genomic or cDNA libraries with probes selected from the sequences of the desired polynucleotide under stringent hybridization conditions.

The polynucleotides encoding a HIV-1 neutralizing peptides or HIV-1 envelope proteins or immunogenic fragments thereof include a recombinant DNA which is incorporated into a vector into an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

DNA sequences encoding the antigen can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

Polynucleotide sequences encoding HIV-1 neutralizing peptides or HIV-1 envelope proteins or immunogenic fragments thereof can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts can include microbial, yeast, insect and mammalian organisms. Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium,* SF9 cells, C129 cells, 293 cells, *Neurospora,* and immortalized mammalian myeloid and lymphoid cell lines. Techniques for the propagation of mammalian cells in culture are well-known (see, Jakoby and Pastan (eds), 1979, Cell Culture. Methods in Enzymology, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression, desirable glycosylation patterns, or other features. In some embodiments, the host cells include HEK293 cells or derivatives thereof, such as GnTI$^{-/-}$ cells (ATCC® No. CRL-3022).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the CaCl$_2$ method using procedures well known in the art. Alternatively, MgCl$_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or viral vectors can be used. Eukaryotic cells can also be co-transformed with polynucleotide sequences encoding a disclosed antigen, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

VI. Viral Vectors

The nucleic acid molecules encoding a disclosed HIV-1 neutralizing peptides or HIV-1 envelope proteins or immunogenic fragments thereof can be included in a viral vector, for example for expression of the HIV-1 neutralizing peptides or HIV-1 envelope proteins or immunogenic fragments thereof in a host cell, or for immunization of a subject as disclosed herein. In some embodiments, the viral vectors are administered to a subject as part of a prime-boost vaccination. In several embodiments, the viral vectors are included in a vaccine, such as a primer vaccine or a booster vaccine for use in a prime-boost vaccination.

In several examples, the viral vector encoding a disclosed HIV-1 neutralizing peptides or HIV-1 envelope proteins or immunogenic fragments thereof can be replication-competent. For example, the viral vector can have a mutation (e.g., insertion of nucleic acid encoding HIV-1 neutralizing peptides or HIV-1 envelope proteins or immunogenic fragments thereof) in the viral genome that does not inhibit viral replication in host cells. The viral vector also can be conditionally replication-competent. In other examples, the viral vector is replication-deficient in host cells.

A number of viral vectors have been constructed, that can be used to express the disclosed HIV-1 neutralizing peptides or HIV-1 envelope proteins or immunogenic fragments thereof, including polyoma, i.e., SV40 (Madzak et al., 1992, *J. Gen. Virol.*, 73:15331536), adenovirus (Berkner, 1992, *Cur. Top. Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.*, 158:91-123; On et al., 1990, *Gene*, 89:279-282), herpes viruses including HSV and EBV (Margolskee, 1992, *Curr. Top. Microbiol. Immunol.*, 158:67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.*, 40:2189-2199), Sindbis viruses (H. Herweijer et al., 1995, *Human Gene Therapy* 6:1161-1167; U.S. Pat. Nos. 5,091,309 and 5,2217,879); alphaviruses (S. Schlesinger, 1993, *Trends Biotechnol.* 11:18-22; I. Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. Cell Biol.*, 5:431-437; Sorge et al., 1984, *Mol. Cell Biol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (Autographa californica multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif.).

VII. Compositions

The disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors can be included in a pharmaceutical composition (including therapeutic and prophylactic formulations), often combined together with one or more pharmaceutically acceptable vehicles and, optionally, other therapeutic ingredients (for example, antibiotics or antiviral drugs). In several embodiments, the disclosed HIV-1 neutralizing peptides, sulfated HIV-1 envelope proteins or immunogenic fragments thereof, protein nanoparticles, or vectors are immunogens; therefore, in several embodiments, pharmaceutical compositions including one or more of these molecules are immunogenic compositions.

Such pharmaceutical compositions can be administered to subjects by a variety of administration modes known to the person of ordinary skill in the art, for example, intramuscular, subcutaneous, intravenous, intra-arterial, intra-articular, intraperitoneal, or parenteral routes.

To formulate the pharmaceutical compositions, the disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors can be combined with various pharmaceutically acceptable additives, as well as a base or vehicle for dispersion of the conjugate. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, TWEEN® 80), solubility enhancing agents (for example, cyclodextrins and derivatives thereof), stabilizers (for example, serum albumin), and reducing agents (for example, glutathione) can be included. Adjuvants, such as aluminum hydroxide (ALHYDROGEL®, available from Brenntag Biosector, Copenhagen, Denmark and AMPHOGEL®, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions.

When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors can be dispersed in a base or vehicle, which can include a hydrophilic compound having a capacity to disperse the HIV neutralizing peptides, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films, for examples for direct application to a mucosal surface.

The disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors can be combined with the base or vehicle according to a variety of methods, and release of the HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors can be by diffusion, disintegration of the vehicle, or associated formation of water channels. In some circumstances, the disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors are dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The pharmaceutical compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the immunogenic compositions can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the disclosed HIV neutralizing peptides can be brought about by including in the composition an agent which delays absorption, for example, monostearate salts and gelatin.

In certain embodiments, the disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors can be administered in a time-release formulation, for example in a composition that includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the disclosed antigen and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body. Numerous systems for controlled delivery of therapeutic proteins are known (e.g., U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342; and 5,534,496).

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the conjugate in the required amount in an appropriate solvent with one or a combination of ingredients enumerated herein, as required, followed by filtered sterilization. Generally, dispersions are prepared by incorporating the disclosed antigen and/or other biologically active agent into a sterile vehicle that contains a basic dispersion medium and the required other ingredients from those enumerated herein. In the case of sterile powders, methods of preparation include vacuum drying and freeze-drying which yields a powder of the disclosed antigen plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like. The sterile preparation is then stored in a dosage form in a sterile container, such as a glass or plastic vial (e.g., with a pierceable lid) or syringe, until administration to a subject.

In one specific, non-limiting example, a pharmaceutical composition for intravenous administration would include about 0.1 µg to 10 mg of a disclosed HIV neutralizing peptides per subject per day. Dosages from 0.1 up to about 100 mg per subject per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995. A unit dosage form contains a suitable single preselected dosage for administration to a subject, or suitable marked or measured multiples of two or more preselected unit dosages, and/or a metering mechanism for administering the unit dose or multiples thereof.

In several embodiments, the compositions include an adjuvant. The person of ordinary skill in the art is familiar with adjuvants, for example, those that can be included in an immunogenic composition. It will be appreciated that the choice of adjuvant can be different in these different applications, and the optimal adjuvant and concentration for each situation can be determined empirically by those of skill in the art.

The pharmaceutical composition typically contains a therapeutically effective amount of one or more of the disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors and can be prepared by conventional techniques. Preparation of immunogenic compositions, including those for administration to human subjects, is generally described in Pharmaceutical Biotechnology, Vol. 61 Vaccine Design—the subunit and adjuvant approach, edited by Powell and Newman, Plenum Press, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757. Typically, the amount of antigen in each dose of the immunogenic composition is selected as an amount which induces an immune response without significant, adverse side effects.

The amount of the disclosed HIV-1 neutralizing peptides, sulfated HIV-1 envelope proteins or immunogenic fragments thereof, protein nanoparticles, polynucleotides encoding the HIV-1 neutralizing peptides or sulfated HIV-1 envelope proteins or immunogenic fragments thereof, or vectors included in an immunogenic composition can vary depending upon the specific agent employed, the route and protocol of administration, and the target population, for example. In some embodiments, for protein therapeutics, typically, each human dose will comprise 1-1000 µg of protein, such as from about 1 µg to about 100 µg, for example, from about 1 µg to about 50 µg, such as about 1 µg, about 2 µg, about 5 µg, about 10 µg, about 15 µg, about 20 µg, about 25 µg, about 30 µg, about 40 µg, or about 50 µg.

In some embodiments, a composition is provided that includes a plurality of HIV-1 envelope proteins or immunogenic fragments thereof comprising a tyrosine residues at gp120 position 173, a tyrosine residue at gp120 position 177, or tyrosine residues at both gp120 positions 173 and 177, wherein the tyrosine residues at gp120 positions 173, 177, or 173 and 177 are sulfated on at least 80% (such as at least 85%, at least 90%, at least 95%, at least 98%) of the HIV-1 envelope proteins or immunogenic fragments in the plurality of HIV-1 envelope proteins or immunogenic fragments are sulfated. In some embodiments, such a composition is provided as a sterile comporision. In more embodiments, such a composition is provided in unit dosage form for use to induce an immune response in a subject, for example, to prevent HIV-1 infection in the subject. In other embodiments, such a composition further includes an adjuvant.

VIII. Methods of Treatment

The HIV-1 neutralizing peptides, sulfated HIV-1 envelope proteins and fragments thereof, protein nanoparticles, polynucleotides encoding the HIV-1 neutralizing peptides and sulfated HIV-1 envelope proteins and fragments thereof, vectors and compositions, can be used in methods of preventing, inhibiting and treating an HIV-1 infection, as well as methods of inducing an immune response to HIV-1, as described below.

In some embodiments, a subject is selected for treatment that has, or is at risk for developing, an HIV infection, for example because of exposure or the possibility of exposure to HIV. Following administration of a therapeutically effective amount of a disclosed HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition, the subject can be monitored for HIV-1 infection, symptoms associated with HIV-1 infection, or both.

Typical subjects intended for treatment with the therapeutics and methods of the present disclosure include humans, as well as non-human primates and other animals. To identify subjects for prophylaxis or treatment according to the methods of the disclosure, accepted screening methods are employed to determine risk factors associated with a targeted or suspected disease or condition, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect and/or characterize HIV infection. These and other routine methods allow the clinician to select patients in need of therapy using the methods and pharmaceutical compositions of the disclosure. In accordance with these methods and principles, a composition can be administered according to the teachings herein, or other conventional methods known to the person of ordinary skill in the art, as an independent prophylaxis or treatment program, or as a follow-up, adjunct or coordinate treatment regimen to other treatments.

The methods can be used to inhibit, treat or prevent HIV infection either in vitro or in vivo. When inhibiting, treating, or preventing infection in vivo, the methods can be used either to avoid infection in an HIV-seronegative subject (e.g., by inducing an immune response that protects against HIV-1 infection), or to treat existing infection in an HIV-seropositive subject. The HIV-seropositive subject may or may not carry a diagnosis of AIDS. Hence in some embodiments the methods involves selecting a subject at risk for contracting HIV infection, or a subject at risk of developing AIDS (such as a subject with HIV infection), and administering a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition, to the subject.

Treatment of HIV by inhibiting HIV replication or infection can include delaying the development of HIV in a subject. Treatment of a HIV also includes reducing signs or symptoms associated with the presence of HIV (for example by reducing or inhibiting HIV replication). In some examples, treatment using the methods disclosed herein prolongs the time of survival of the subject.

The administration of a disclosed HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition can be for either prophylactic or therapeutic purpose. When provided prophylactically, the disclosed therapeutic agents are provided in advance of any symptom, for example in advance of infection. The prophylactic administration of the disclosed therapeutic agents serves to prevent or ameliorate any subsequent infection. When provided therapeutically, the disclosed therapeutic agents are provided at or after the onset of a symptom of disease or infection, for example after development of a symptom of HIV-1 infection, or after diagnosis of HIV-1 infection. The therapeutic agents can thus be provided prior to the anticipated exposure to HIV virus so as to attenuate the anticipated severity, duration or extent of an infection and/or associated disease symptoms, after exposure or suspected exposure to the virus, or after the actual initiation of an infection.

For prophylactic and therapeutic purposes, a disclosed HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the therapeutic agents can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, ferret, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the composition (for example, amounts that are effective to elicit a desired immune response or alleviate one or more symptoms of a targeted disease). In alternative embodiments, an effective amount or effective dose of the composition may simply inhibit or enhance one or more selected biological activities correlated with a disease or condition, as set forth herein, for either therapeutic or diagnostic purposes.

HIV infection does not need to be completely eliminated for the methods to be effective. For example, treatment with one or more of the disclosed therapeutic agents can decrease HIV infection by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to HIV infection in the absence of the composition. In additional examples, HIV replication can be reduced or inhibited by the disclosed methods. HIV replication does not need to be completely eliminated for the method to be effective. For example, treatment with one or more of the provided HIV neutralizing peptides decreases HIV replication by a desired amount, for example by at least 10%, at least 20%, at least 50%, at least 60%, at least 70%, at least 80%, at least 90%, at least 95%, at least 98%, or even at least 100% (elimination of detectable HIV replication), as compared to HIV replication in the absence of the composition.

To successfully reproduce itself, HIV must convert its RNA genome to DNA, which is then imported into the host cell's nucleus and inserted into the host genome through the action of HIV integrase. Because HIV's primary cellular target, CD4+ T-Cells, can function as the memory cells of the immune system, integrated HIV can remain dormant for the duration of these cells' lifetime. Memory T-Cells may survive for many years and possibly for decades. This latent HIV reservoir can be measured by co-culturing CD4+ T-Cells from infected patients with CD4+ T-Cells from uninfected donors and measuring HIV protein or RNA (See, e.g., Archin et al., *AIDS*, 22:1131-1135, 2008). In some embodiments, the provided methods of treating or inhibiting HIV infection include reduction or elimination of the latent reservoir of HIV infected cells in a subject. For example, a reduction of at least 10%, at least 20%, at least 50%, at least 60%, at least 70%, at least 80%, at least 90%, at least 95%, at least 98%, or even at least 100% (elimination of detectable HIV) of the latent reservoir of HIV infected cells in a subject, as compared to the latent reservoir of HIV infected cells in a subject in the absence of the treatment with one or more of the provided bispecific antibodies.

Studies have shown that the rate of HIV transmission from mother to infant is reduced significantly when zidovudine is administered to HIV-infected women during pregnancy and delivery and to the offspring after birth (Connor et al., 1994 *Pediatr Infect Dis J* 14: 536-541). Several studies of mother-to-infant transmission of HIV have demonstrated a correlation between the maternal virus load at delivery and risk of HIV transmission to the child. The present disclosure provides HIV-1 neutralizing peptides, sulfated HIV-1 envelope proteins and fragments thereof, protein nanoparticles, polynucleotides encoding the HIV-1 neutralizing peptides and sulfated HIV-1 envelope proteins and fragments thereof, vectors and compositions that are of use in decreasing HIV-transmission from mother to infant. Thus, in some embodiments a therapeutically effective amount of one or more of the provided therapeutic agents is administered in order to prevent transmission of HIV, or decrease the risk of transmission of HIV, from a mother to an infant. In some embodiments, a therapeutically effective amount of a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition, is administered to a pregnant subject to induce an immune response that generates neutralizing antibodies that are passes to the fetus via the umbilical cord to protect the fetus from infection during birth. In some embodiments, a therapeutically effective amount of the therapeutic agents is administered to mother and/or to the child at childbirth. In other examples, a therapeutically effective amount of a disclosed therapeutic agent is administered to the mother and/or infant prior to breast feeding in order to prevent viral transmission to the infant or decrease the risk of viral transmission to the infant. In some embodiments, both a therapeutically effective amount of a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition and a therapeutically effective amount of another agent, such as zidovudine, is administered to the mother and/or infant.

A therapeutically effective amount of a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition, can be administered to a subject. A therapeutically effective amount of such agents will depend upon the severity of the disease and/or infection and the general state of the patient's health. For example, a therapeutically effective amount of the HIV neutralizing peptide is that which provides either subjective relief of a symptom(s) or an objectively identifiable improvement as noted by the clinician or other qualified observer.

The actual dosage of a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition, or composition will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the composition for eliciting the desired activity or biological response in the subject. Dosage regimens can be adjusted to provide an optimum prophylactic or therapeutic response. As described above in the forgoing listing of terms, an effective amount is also one in which any toxic or detrimental side effects of the disclosed antigen and/or other biologically active agent is outweighed in clinical terms by therapeutically beneficial effects. A non-limiting range for a therapeutically effective amount of the disclosed HIV neutralizing peptides or sulfated HIV-1 envelope proteins or fragments thereof within the methods and compositions of the disclosure is about 0.01 mg/kg body weight to about 10 mg/kg body weight, such as about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 4 mg/kg, about 5 mg/kg, or about 10 mg/kg, for example 0.01 mg/kg to about 1 mg/kg body weight, about 0.05 mg/kg to about 5 mg/kg body weight, about 0.2 mg/kg to about 2 mg/kg body weight, or about 1.0 mg/kg to about 10 mg/kg body weight.

In one specific, non-limiting example, a composition for intravenous administration would include about 0.1 µg to 10 mg of a disclosed HIV neutralizing peptide or sulfated HIV-1 envelope protein or immunogenic fragment thereof per subject per day. In another example, the dosage can range from 0.1 up to about 100 mg of HIV neutralizing peptide or sulfated HIV-1 envelope protein or immunogenic fragment thereof per subject per day, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remingtons Pharmaceutical Sciences*, 19$^{th}$ Ed., Mack Publishing Company, Easton, Pa., 1995.

Dosage can be varied by the attending clinician to maintain a desired concentration at a target site (for example, systemic circulation). Higher or lower concentrations can be selected based on the mode of delivery, for example, transepidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth. To achieve the same serum concentration level, for example, slow-release particles with a release rate of 5 nanomolar (under standard conditions) would be administered at about twice the dosage of particles with a release rate of 10 nanomolar.

In several embodiments, it may be advantageous to administer the therapeutic agents disclosed herein with other agents such as proteins, peptides, antibodies, and other antiviral agents, such as anti-HIV agents. Examples of such anti-HIV therapeutic agents include nucleoside reverse transcriptase inhibitors, such as abacavir, AZT, didanosine, emtricitabine, lamivudine, stavudine, tenofovir, zalcitabine, zidovudine, and the like, non-nucleoside reverse transcriptase inhibitors, such as delavirdine, efavirenz, nevirapine, protease inhibitors such as amprenavir, atazanavir, indinavir, lopinavir, nelfinavir, osamprenavir, ritonavir, saquinavir, tipranavir, and the like, and fusion protein inhibitors such as enfuvirtide and the like. In some examples, the disclosed therapeutic agents are administered with T-helper cells, such as exogenous T-helper cells. Exemplary methods for producing and administering T-helper cells can be found in International Patent Publication WO 03/020904, which is incorporated herein by reference.

For any application, treatment with a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition can be combined with anti-retroviral therapy, such as HAART. Antiretroviral drugs are broadly classified by the phase of the retrovirus life-cycle that the drug inhibits. The therapeutic agents can be administered before, during, concurrent to and/or after retroviral therapy. In some embodiments, the therapeutic agents are administered following a course of retroviral therapy. The disclosed therapeutic agents can be administered in conjunction with nucleoside and nucleotide reverse transcriptase inhibitors (nRTI), non-nucleoside reverse transcriptase inhibitors (NNRTI), protease inhibitors, Entry inhibitors (or fusion inhibitors), Maturation inhibitors, or a broad spectrum inhibitors, such as natural antivirals. Exemplary agents include lopinavir, ritonavir, zidovudine, lamivudine, tenofovir, emtricitabine and efavirenz.

In some embodiments, a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition is used as an immunogen to prime or induce an immune response (such as a T or B cell response) to HIV-1 in a subject. Such methods include administering to a subject a therapeutically effective amount of a disclosed HIV-1 neutralizing peptide, sulfated HIV-1 envelope protein or immunogenic fragment thereof, protein nanoparticle, polynucleotide encoding the HIV-1 neutralizing peptide or sulfated HIV-1 envelope protein or immunogenic fragment thereof, vector, or composition, to prime or enhance an immune response, for example, an immune response to an HIV envelope protein, such as gp160, gp140, gp120 or gp41.

In several embodiments, administration of the therapeutically effective amount of a disclosed HIV-1 neutralizing peptide, sulfated HIV-1 envelope protein or immunogenic fragment thereof, protein nanoparticle, polynucleotide encoding the HIV-1 neutralizing peptide or sulfated HIV-1 envelope protein or immunogenic fragment thereof, vector, or composition induces a T cell response. In some such embodiments, the T cell response is a $CD4^+$ T helper cell response, such as a Th1 cell response.

In some embodiments, the HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition is administered to the subject simultaneously with the administration of the adjuvant. In other embodiments, the HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition is administered to the subject after the administration of the adjuvant and within a sufficient amount of time to induce the immune response.

The HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition can be used in coordinate vaccination protocols or combinatorial formulations. In certain embodiments, novel combinatorial and coordinate immunization protocols employ separate immunogens or formulations, each directed toward eliciting an anti-HIV immune response, such as an immune response to HIV-1 gp120 protein. Separate immunogenic compositions that elicit the anti-HIV immune response can be combined in a polyvalent immunogenic composition administered to a subject in a single immunization step, or they can be administered separately (in monovalent immunogenic compositions) in a coordinate immunization protocol.

Administration of a HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition induces a sufficient immune response to treat the pathogenic infection, for example, to inhibit the infection and/or reduce the signs and/or symptoms of the infection. Amounts effective for this use will depend upon the severity of the disease, the general state of the subject's health, and the robustness of the subject's immune system.

In one embodiment, a suitable immunization regimen includes at least two separate inoculations with one or more immunogenic compositions, with a second inoculation being administered more than about two, about three to eight, or about four, weeks following the first inoculation. A third inoculation can be administered several months after the second inoculation, and in specific embodiments, more than about five months after the first inoculation, more than about six months to about two years after the first inoculation, or about eight months to about one year after the first inoculation. Periodic inoculations beyond the third are also desirable to enhance the subject's "immune memory." The adequacy of the vaccination parameters chosen, e.g., formulation, dose, regimen and the like, can be determined by taking aliquots of serum from the subject and assaying antibody titers during the course of the immunization program. Alternatively, the T cell populations can be monitored by conventional methods. In addition, the clinical condition of the subject can be monitored for the desired effect, e.g., prevention of HIV-1 infection or progression to AIDS, improvement in disease state (e.g., reduction in viral load), or reduction in transmission frequency to an uninfected partner. If such monitoring indicates that vaccination is sub-optimal, the subject can be boosted with an additional dose of immunogenic composition, and the vaccination parameters can be modified in a fashion expected to potentiate the immune response. Thus, for example, the dose of the chimeric non-HIV polypeptide or polynucleotide and/or adjuvant can be increased or the route of administration can be changed.

It is contemplated that there can be several boosts, and that each boost can be a different HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition. It is also contemplated in some examples that the boost may be the same disclosed HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition as another boost, or the prime.

The prime can be administered as a single dose or multiple doses, for example two doses, three doses, four doses, five doses, six doses or more can be administered to a subject over days, weeks or months. The boost can be administered as a single dose or multiple doses, for example two to six doses, or more can be administered to a subject over a day, a week or months. Multiple boosts can also be given, such one to five, or more. Different dosages can be used in a series of sequential inoculations. For example a relatively large dose in a primary inoculation and then a boost with relatively smaller doses. The immune response against the selected antigenic surface can be generated by one or more inoculations of a subject.

Upon administration of an HIV-1 neutralizing peptide, sulfated HIV-1 envelope protein or immunogenic fragment thereof, polynucleotide encoding a HIV-1 neutralizing peptide or sulfated HIV-1 envelope protein or immunogenic fragment thereof, vector, or composition of this disclosure, the immune system of the subject typically responds to the immunogenic composition by producing antibodies specific for HIV-1 gp120 protein. Such a response signifies that an immunologically effective dose was delivered to the subject.

An immunologically effective dosage can be achieved by single or multiple administrations (including, for example, multiple administrations per day), daily, or weekly administrations. For each particular subject, specific dosage regimens can be evaluated and adjusted over time according to the individual need and professional judgment of the person administering or supervising the administration of the immunogenic composition. In some embodiments, the antibody response of a subject will be determined in the context of evaluating effective dosages/immunization protocols. In most instances it will be sufficient to assess the antibody titer in serum or plasma obtained from the subject. Decisions as to whether to administer booster inoculations and/or to change the amount of the therapeutic agent administered to the individual can be at least partially based on the antibody titer level. The antibody titer level can be based on, for example, an immunobinding assay which measures the concentration of antibodies in the serum which bind to an antigen including the HIV neutralizing peptide, for example, a HIV-1 gp120 protein. The methods of using immunogenic composition, and the related compositions and methods of the disclosure are useful in increasing resistance to, preventing, ameliorating, and/or treating infection and disease caused by HIV (such as HIV-1) in animal hosts, and other, in vitro applications.

In certain embodiments, the HIV-1 neutralizing peptide, sulfated HIV-1 envelope protein or immunogenic fragment thereof, protein nanoparticle, polynucleotide encoding a HIV-1 neutralizing peptide or sulfated HIV-1 envelope protein or immunogenic fragment thereof, vector, or composition is administered sequentially with other anti-HIV therapeutic agents, such as before or after the other agent. One of ordinary skill in the art would know that sequential administration can mean immediately following or after an appropriate period of time, such as hours, days, weeks, months, or even years later.

In additional embodiments, a therapeutically effective amount of a pharmaceutical composition including a nucleic acid encoding a disclosed HIV-1 neutralizing peptide, sulfated HIV-1 envelope protein or immunogenic fragment thereof is administered to a subject, for example to generate an immune response. In one specific, non-limiting example, a therapeutically effective amount of a nucleic acid encoding a disclosed HIV-1 neutralizing peptide, sulfated HIV-1 envelope protein or immunogenic fragment thereof is administered to a subject to treat or prevent or inhibit HIV infection, or to induce an immune response to HIV-1 (such as to gp120) in the subject.

One approach to administration of nucleic acids is direct immunization with plasmid DNA, such as with a mammalian expression plasmid. As described above, the nucleotide sequence encoding a disclosed HIV neutralizing peptide can be placed under the control of a promoter to increase expression of the molecule.

Immunization by nucleic acid constructs is well known in the art and taught, for example, in U.S. Pat. No. 5,643,578 (which describes methods of immunizing vertebrates by introducing DNA encoding a desired antigen to elicit a cell-mediated or a humoral response), and U.S. Pat. Nos. 5,593,972 and 5,817,637 (which describe operably linking a nucleic acid sequence encoding an antigen to regulatory sequences enabling expression). U.S. Pat. No. 5,880,103 describes several methods of delivery of nucleic acids encoding immunogenic peptides or other antigens to an organism. The methods include liposomal delivery of the nucleic acids (or of the synthetic peptides themselves), and immune-stimulating constructs, or ISCOMS™, negatively charged cage-like structures of 30-40 nm in size formed spontaneously on mixing cholesterol and Quil A™ (saponin). Protective immunity has been generated in a variety of experimental models of infection, including toxoplasmosis and Epstein-Barr virus-induced tumors, using ISCOMS™ as the delivery vehicle for antigens (Mowat and Donachie, *Immunol. Today* 12:383, 1991). Doses of antigen as low as 1 μg encapsulated in ISCOMS™ have been found to produce Class I mediated CTL responses (Takahashi et al., *Nature* 344:873, 1990).

In another approach to using nucleic acids for immunization, a disclosed HIV-1 neutralizing peptide, sulfated HIV-1 envelope protein or immunogenic fragment thereof can also be expressed by attenuated viral hosts or vectors or bacterial vectors. Recombinant vaccinia virus, adeno-associated virus (AAV), herpes virus, retrovirus, cytogmeglo virus or other viral vectors can be used to express the peptide or protein, thereby eliciting a CTL response. For example, vaccinia vectors and methods useful in immunization protocols are described in U.S. Pat. No. 4,722,848. BCG (Bacillus Calmette Guerin) provides another vector for expression of the peptides (see Stover, *Nature* 351:456-460, 1991).

In one embodiment, a nucleic acid encoding a disclosed antigen is introduced directly into cells. For example, the nucleic acid can be loaded onto gold microspheres by standard methods and introduced into the skin by a device such as Bio-Rad's HELIOS™ Gene Gun. The nucleic acids can be "naked," consisting of plasmids under control of a strong promoter. Typically, the DNA is injected into muscle, although it can also be injected directly into other sites, including tissues in proximity to metastases. Dosages for injection are usually around 0.5 μg/kg to about 50 mg/kg, and typically are about 0.005 mg/kg to about 5 mg/kg (see, e.g., U.S. Pat. No. 5,589,466).

IX. Kits

Kits are also provided. For example, kits for treating, inhibiting or preventing HIV-1 infection in a subject, or for inducing an immune response to gp120 in a subject. The kits typically include an HIV neutralizing peptide as disclosed herein. More than one of the HIV neutralizing peptide can be included in the kit. Thus, the kit can include two or more HIV neutralizing peptide.

In one embodiment, a kit includes instructional materials disclosing means of use of an HIV neutralizing peptide. The instructional materials may be written, in an electronic form (such as a computer diskette or compact disk) or may be visual (such as video files). The kits may also include additional components to facilitate the particular application for which the kit is designed. The kits may additionally include buffers and other reagents routinely used for the practice of a particular method. Such kits and appropriate contents are well known to those of skill in the art.

EXAMPLES

The following examples are provided to illustrate certain particular features and/or embodiments. These examples should not be construed to limit the disclosure to the particular features or embodiments described.

Example 1

Binding of V2 to V3 Via CCR5 Mimicry Stabilizes Native HIV-1 gp120 and Facilitates Immune Evasion This example illustrates that an intramolecular interaction between a tyrosine-sulfated, CCR5-mimicking domain of V2 stabilizes HIV-1 gp120 in its native, antibody-shielded conformation.

Native envelope spikes on the surface of HIV-1 virions are homotrimers of a heterodimeric glycoprotein formed by gp120 and gp41 subunits. Upon binding to the CD4 receptor, the external subunit, gp120, undergoes dramatic conformational changes that lead to a low-energy state (the CD4-bound conformation), promoting high-affinity interaction with a coreceptor such as CCR5 or CXCR4 and eventually activation of the gp41 fusogenic mechanism. Although gp120 represents a primary target for neutralizing antibodies, the CD4-unliganded native envelope adopts a cryptic conformation that, albeit energetically unfavorable, limits antibody accessibility to the conserved receptor-binding surfaces. A critical role in constraining the HIV-1 envelope in its native, metastable conformation is played by the second (V2) and third (V3) variable loops of gp120, since deletion of these loops causes the protein to fall into the CD4-bound conformation. Due to inherent technical hurdles in crystallizing full-length gp120, available high-definition X-ray structures were obtained with V2- and/or V3-truncated, deglycosylated core gp120 molecules (Kwong et al., *Nature* 393, 648-659, 1998; Kwong et al., *Structure* 8, 1329-1339, 2000; Huang et al., *Science* 310, 1025-1028, 2005; Chen et al., *Science* 326, 1123-1127, 2009; Pancera et al., *Proc Natl Acad Sci USA* 107, 1166-1171, 2010). Thus, these structures not only lack any detail about the conformation and spatial arrangement of V2 and V3, which are increasingly recognized as targets of broadly neutralizing antibodies (Moore et al., *J Virol* 85, 3128-3141, 2011; Walker et al., *Science* 326, 285-289, 2009; Walker et al., *Nature* 477, 466-470, 2011), but they invariably represent the CD4-bound conformation, which is less relevant for vaccine design.

The direct interaction between V2 and V3 has never been proven, and the function of these critical domains in the structuring of the native envelope has remained elusive. Since amino acid (aa) conservation is a common correlate of function, the degree of variability in different domains of V2 was analyzed. In spite of its definition as a variable loop, V2 contains highly conserved regions. In agreement with previous data (Zolla-Pazner et al., *Nat Rev Immunol* 10, 527-535, 2010), alignment of 6,575 V2 sequences from various HIV-1 genetic subtypes (A to F) documented a high degree of both intra- and inter-subtype aa conservation with only a short region of high variability (FIG. 1A).

Figure 6:
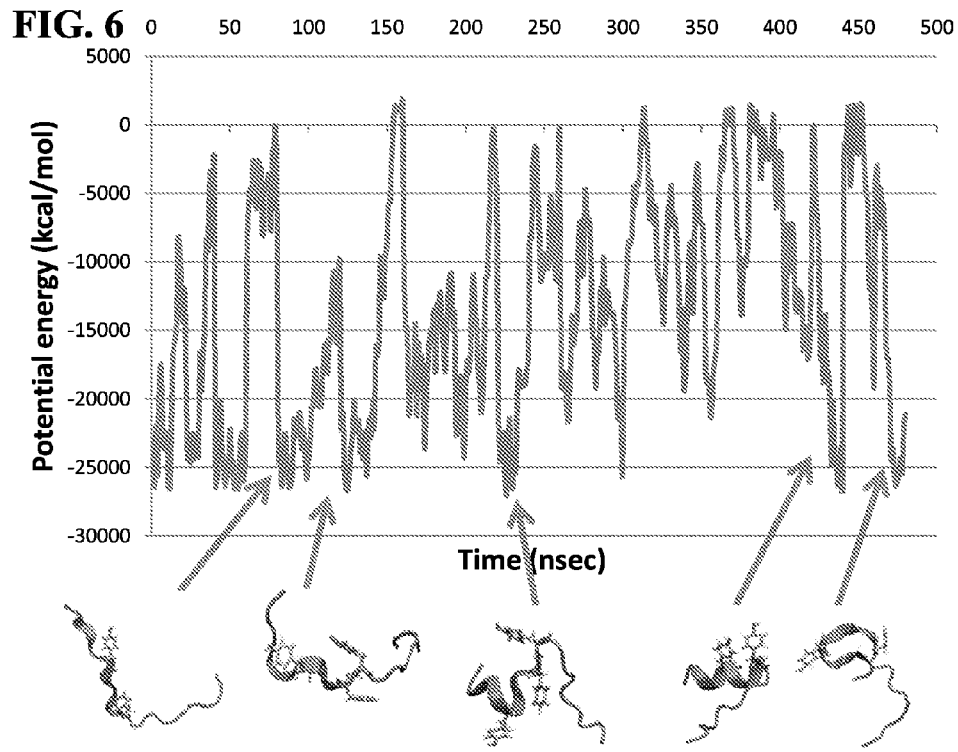
FIG. 6 shows a graph and a series of ribbon diagrams illustrating a Plot of potential energy at 1 nsec intervals from a replica exchange molecular dynamics (REMD) simulation of an 18 mer peptide comprising HIV-1 gp120 residues 168-185 (KVQKEYALFYELDIVPID; SEQ ID NO: 8) from the V2 loop. Forty replicas were run for 12 nsec providing 0.48 msec of simulation time. Selected low-energy conformations are shown. Within the 5% lowest energy conformations, 12.5% contained an α-helix, one contained a β-strand-like structure and the remaining showed no discernible secondary structure.

Several computational methods were used to explore the structure-function relationships in V2. Secondary structure predictions of V2 from a prototypic CCR5-tropic (R5) subtype-B isolate, HIV-1 BaL, using different algorithms revealed the presence of an α-helix with high confidence in the highly conserved central domain of V2, spanning aa 168 to 178 (according to strain HXB2 numbering) (FIG. 1B). Of note, this segment is contiguous but does not overlap with the LDI/V motif (aa 179-181), which binds integrin α4β7, an accessory HIV-1 receptor (Arthos et al., *Nat Immunol* 9, 301-309, 2008). Tertiary structure modeling using both molecular dynamics (Gromacs) and a Monte Carlo folding method (ROSETTA) also predicted an α-helix within the same region (FIG. 1C). To further evaluate the α-helix formation and stability, the conformational space was exhaustively explored starting from a random-coil configuration of an 18mer peptide spanning aa168-185 (designated pV2α) using replica-exchange molecular dynamics (REMD). An α-helix was detected among lower-energy conformations (FIG. 6). To experimentally validate the presence of the α-helix predicted in silico, peptide pV2α was synthesized and analyzed by circular dichroism. Because prolines are known to disrupt α-helices a peptide containing a proline insertion between Tyr173 and Ala174 (pV2α-Pro) was also synthesized. Circular dichroism confirmed the presence of a helical signature in pV2α, which was absent in pV2α-Pro (FIG. 1D).

Figure 2J:
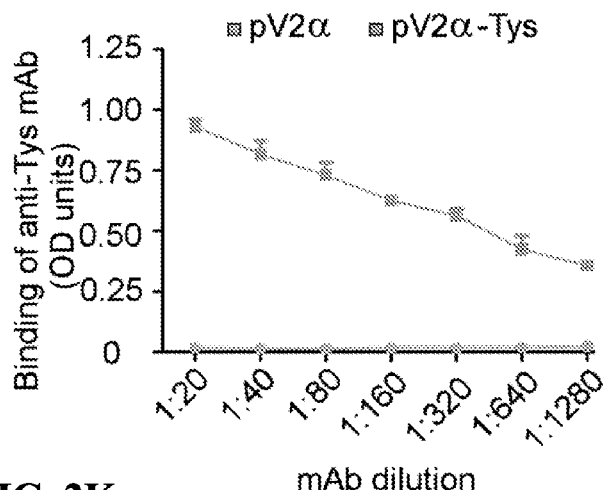

The conserved central region of the V2 loop of HIV-1 gp120 contains sulfated tyrosines. Next, whether the conserved α-helix identified in V2 could be relevant to the functional structuring of the HIV-1 envelope was investigated. Since the N-terminal domain of the CCR5 coreceptor, which was shown to adopt a helical conformation, interacts with a conserved domain at the base of V3 (Huang et al., *Science* 317, 1930-1934, 2007), it was assayed to determine if the V2 and CCR5 α-helices could mediate a similar interaction with V3. Superposition of the two helices indeed demonstrated a high degree of structural homology with a Cα root-mean-square deviation (RMSD) of 0.69 Å. Because the CCR5 N-terminus contains tyrosine residues that are post-translationally sulfated (Farzan et al., *Cell* 96, 667-676, 1999) to stabilize the interaction with gp120 (Farzan et al., *J Biol Chem* 275, 33516-33521, 2000) and the V2 α-helix contains two tyrosine residues (Tyr173 and Tyr177) with identical spacing as sulfotyrosine (Tys)10 and Tys14 in CCR5 (FIG. 2A), whether the V2 tyrosines could also be sulfated was evaluated using a highly specific anti-sulfotyrosine (Tys) mAb (FIG. 2J). For FIG. 2J, the peptides were directly coated on the surface of 96-well flat-bottom plastic plates by overnight incubation at 4° C. in PBS; the plates were then washed and blocked with 0.5% casein. The mAb was added at the indicated dilutions for 2 hrs at room temperature (RT), followed by repeated washing and addition of a secondary sheep-anti-mouse-IgG antiserum conjugated to horseradish peroxidase. After further incubation for 2 hrs at RT, the reaction was revealed by addition of a specific substrate. (K) Detection of sulfated tyrosines by autoradiography in metabolically-labeled HEK293 cells expressing WT or ΔV2 (Δ164-190) HIV-1 BaL gp160. The cells were labeled with free [$^{35}$S]sulfate or [$^{35}$S]cysteine/[$^{35}$S]methionine by overnight incubation in sulfate-free or cysteine/methionine-free media, respectively. The films were exposed for 48 hrs for [$^{35}$S]sulfate labeling and for 18 hrs for [$^{35}$S]cysteine/[$^{35}$S]methionine labeling.

Strikingly, the presence of sulfated tyrosines in virion-associated gp120 from different HIV-1 isolates grown in primary CD4$^+$ T cells was detected (FIG. 2B). Further, the presence of sulfated tyrosines in gp120 immunoprecipitated from the surface of HeLa cells expressing recombinant full-length gp160 from the subtype-B CCR5-tropic (R5) isolate BaL was confirmed (FIG. 1C). Since gp120 contains additional tyrosines both within and outside V2, a V2-deletion mutant of HIV-1 BaL that selectively excludes Tyr173 and Tyr177 was produced (BaL Δ164-190). While the level of expression of gp120 was unaltered, the sulfated-tyrosine signal was abrogated in the deletion mutant, indicating that sulfation was specific to Tyr173 and Tyr177 in V2 (FIG. 2C).

Figure 2K:
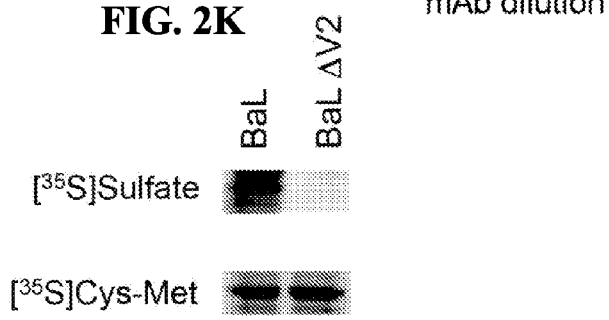

To confirm the presence of sulfated tyrosines in gp120 and their selective localization in the V2 region using a different methodology, metabolic labeling with free [$^{35}$S]sulfate in cells expressing HIV-1 BaL WT or the partially deleted ΔV2 mutant was performed. Gp120 was immunoprecipitated from metabolically labeled cells, deglycosylated to exclude [$^{35}$S]sulfate incorporated into glycans, and analyzed by autoradiography. Whereas both WT and ΔV2 incorporated comparable amounts of [$^{35}$S]cysteine and [$^{35}$S]methionine, only WT, but not ΔV2, showed free [$^{35}$S]sulfate incorporation (FIG. 2K), confirming the presence of sulfated tyrosines in gp120 and their location within the central V2 domain.

The identity of the sulfated tyrosines was further confirmed by mutating Tyr173 and Tyr177 to phenylalanine both individually (Y173F, Y177F) and in combination (Y173F/177F). All three mutants showed a complete loss of sulfated-tyrosine signal (FIG. 2D); the loss of signal observed with individual phenylalanine mutants is in line with observations made with CCR5 N-terminal phenylalanine mutants (Farzan et al., Cell 96, 667-676, 1999), suggesting that the absence of proximal tyrosines or the presence of phenylalanines impairs sulfation in neighboring tyrosines.

Figure 7:
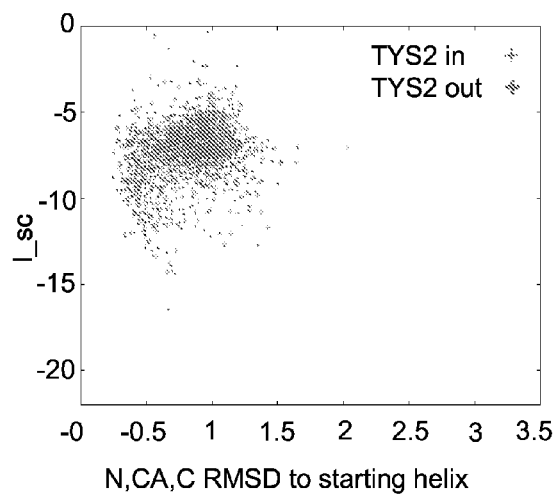
FIGS. 7 and 8 are a graph and a ribbon diagram illustrating the docking of the tyrosine-sulfated V2 α-helix to gp120 by ROSETTA FlexPepDock.
Figure 8:
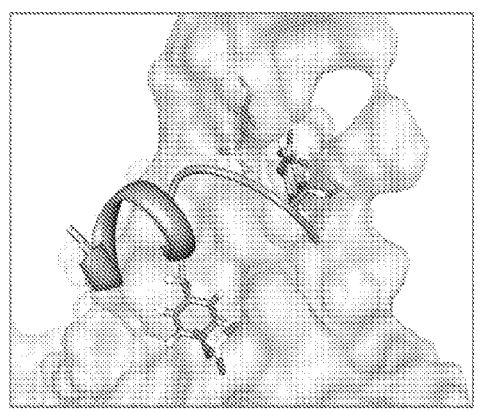

Having established that the central domain of V2 adopts a helical conformation and contains sulfated tyrosines, whether this region could mediate binding to the conserved base of V3 in a fashion similar to the predicted interaction of the CCR5 N-terminus (Huang et al., Science 317, 1930-1934, 2007) was further investigated. First, different computational approaches were undertaken to investigate the binding of the V2 α-helix to the base of V3 and assess the impact of tyrosine sulfation. Flexible docking of a tyrosine-sulfated variant of peptide pV2α (pV2α-Tys) by ROSETTA documented an energetically favorable interaction with gp120, with Tys177 (analogous to Tys14 in CCR5) positioned inside a cavity at the base of V3 (FIGS. 7 and 8). Molecular dynamics confirmed the stability of pV2α-Tys binding to gp120 throughout a 100-nsec simulation and its dependence (25% of the total energy) upon insertion of Tys177 into a deep cavity at the base of V3 formed by V3, C3 and C4 elements (FIG. 2, E to I), analogous to that seen in the CCR5-docked model (Hu et al., J Virol 85, 2741-2750, 2011). The interaction energy was markedly more favorable (~150 kcal/mol) for Tys177 than for the unmodified Tyr177 with a preponderant contribution of electrostatic interactions (FIG. 2E). In the dynamic simulation, the sidechain of Tys177 lies parallel to the C4 loop inside the cavity, which is lined by the Arg440 sidechain on one side and Ile326 on the other, both of which interact with the aromatic ring of Tys177. The sulfate group of Tys177 is mostly buried and forms hydrogen bonds to the backbone of Gly441 and to the sidechain of Asn302, while the sulfate group of Tys173 forms hydrogen bonds to the guanido groups of Arg327 (FIG. 2, F to I). The preponderant role of Tys177 in stabilizing the complex is also reflected by its high conservation across all HIV-1 subtypes (FIG. 1A). Of note, although the interactions of the unsulfated peptide (pV2α) with the V3 base are less extensive compared to those of pV2α-Tys, its overall binding mode is similar with Tyr177 positioned inside the V3 pocket albeit with a markedly lower energy (FIG. 2E).

Figure 2L:
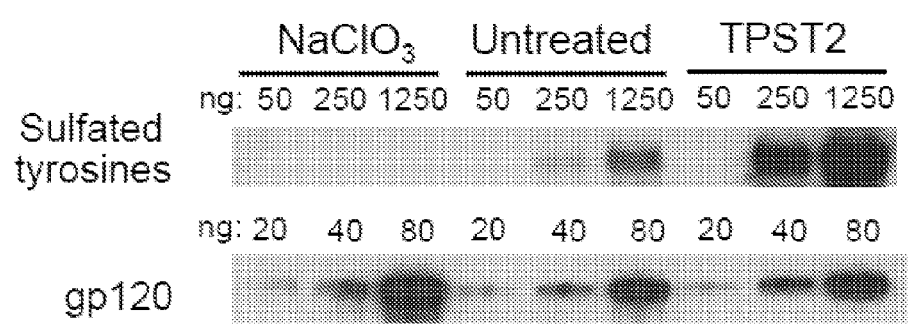
FIGS. 2L-2O illustrate the different efficiency of V2 tyrosine sulfation in recombinant gp120 produced in epithelial cell lines versus virion-associated gp120 produced by primary CD4$^+$ T cells. (L) Detection of sulfated tyrosines by Western blot in recombinant gp120 produced in CHO cells. (M) Lack of adverse effects of sodium chlorate treatment or TPST2 overexpression on the viability of HeLa and HEK293 cells. The cell lines were treated with 30 mM sodium chlorate (NaClO$_3$) or transfected with a plasmid vector expressing TPST2 and cultured for 72 hrs. Cell viability was measured by quantitative counting using timed flow cytometry on a FACSCanto II and is expressed as percent viable cell recovery. (N) Side-by-side comparison of the extent of tyrosine sulfation detected by Western blot in a reference sulfated mAb (412d), in virion-associated gp120 produced by infected primary human CD4$^+$ T cells (V-gp120), and in recombinant gp120 produced in HEK293 cells (R-gp120). Identical amounts of mAb 412d and purified gp120 were loaded on the gels. For V-gp120, the protein was immunoprecipitated directly from the infectious viral stocks. The antibodies used for Western blots and the methods used for relative quantification were the same as in (L). (O) Detection of sulfated tyrosines by Western blot in gp120 purified from HIV-1 virions produced by infected primary human CD4+ T cells as described for (N).
Figure 2M:
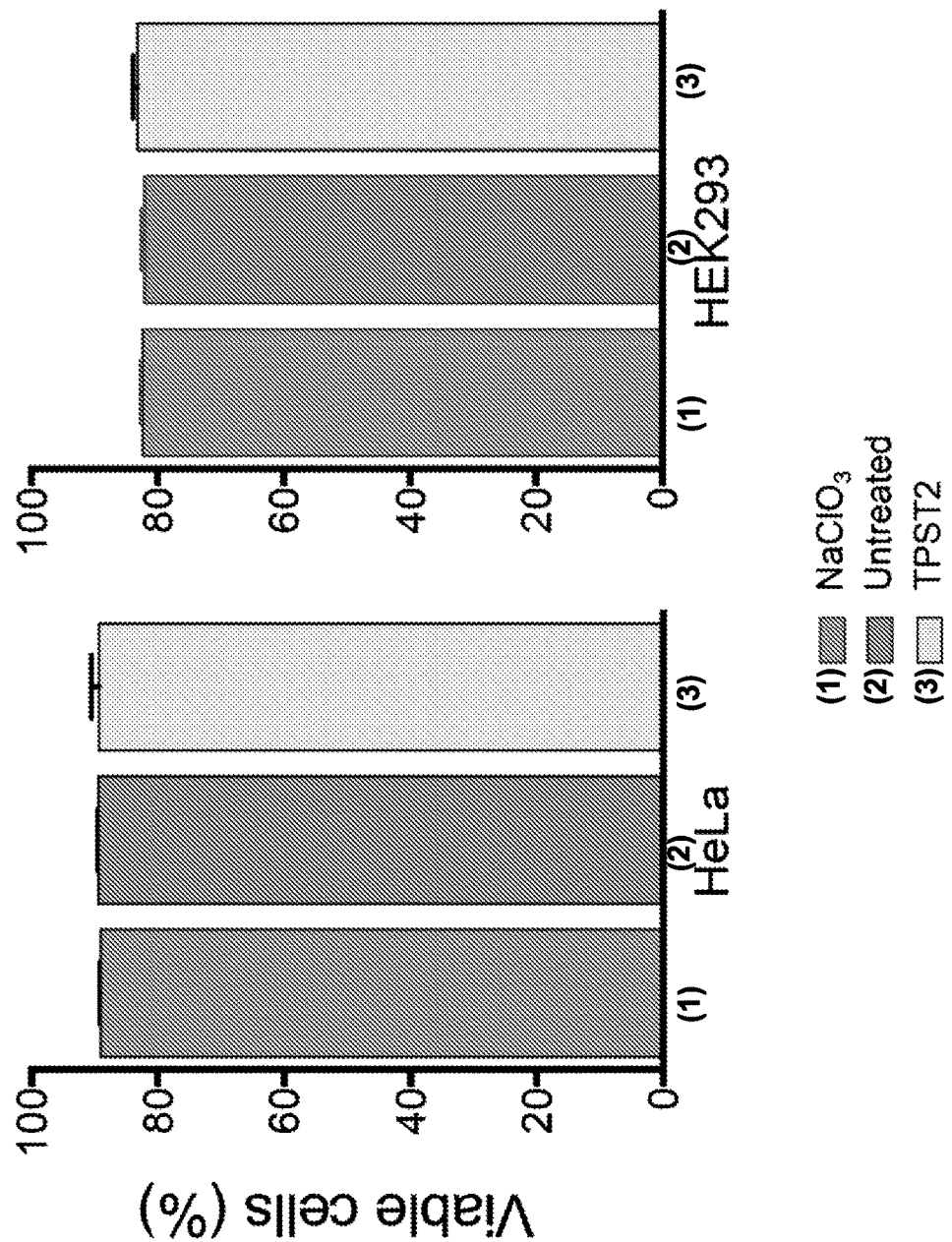

Overexpression of TPST2 augments the low constitutive levels of tyrosine sulfation in recombinant Gp120 produced in epithelial cell lines. Since epithelial cell lines, such as those commonly utilized to produce recombinant proteins in vitro, are inefficient in post-translationally modifying tyrosines by O-sulfation (Choe, H., et al. (2003) Cell 114, 161-170), the constitutive level of gp120 tyrosine sulfation in CHO cells and whether it could be increased by overexpression of the sulfating enzyme tyrosyl protein sulfotransferase 2 (TPST2) were studied; an inhibitor of sulfotransferases, sodium chlorate (NaCLO$_3$), was tested in parallel as a control. FIG. 2L shows that the level of tyrosine sulfation in recombinant gp120 (isolate BaL) produced in CHO was low, with a very low normalized ratio (0.04-0.06) between the signals obtained with the anti-sulfotyrosine antibody and the loading control (anti-gp120 mAb b24), suggesting that only a minor fraction of the protein was constitutively sulfated. However, the level of tyrosine sulfation was dramatically increased upon TPST2 overexpression, with a marked improvement of the signal ratio (0.37-0.42). As expected, treatment with sodium chlorate totally abrogated gp120 sulfation, while having no negative effects on cell viability (FIG. 2M).

For FIG. 2L, the effects of overexpression of the sulfating enzyme TPST2 or treatment with the sulfotransferase inhibitor sodium chlorate (NaClO$_3$; 30 mM) were also tested. Increasing amounts of purified gp120 were loaded on the gels. The presence of sulfated tyrosines was assayed with a specific mAb; the loading controls with an anti-gp120 mAb (b24) directed to an invariant region in C2. Following quantification by densitometry, the values for individual bands were normalized as OD units per ng of protein and used to calculate the ratios between anti-sulfotyrosine signals and loading controls indicated below each quantifiable band.

Figure 2N:
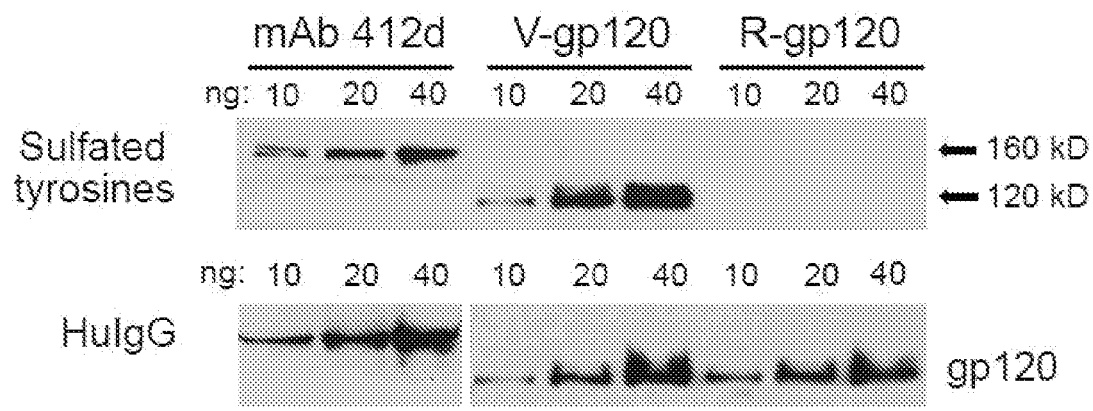

V2 tyrosine sulfation is efficient in virion-associated gp120 produced by infected primary CD4$^+$ T cells. Next, the levels of V2 tyrosine sulfation in gp120 purified by immunoprecipitation from HIV-1 virions produced by primary human CD4$^+$ T lymphocytes, which are physiologically relevant target cells for HIV-1 infection, was tested. The sulfation levels were quantified by direct side-by-side comparison with a reference sulfated human mAb, 412d, which contains two sulfated tyrosines in its CDRH3 domain (Choe, H., et al. (2003) Cell 114, 161-170). When identical amounts of HIV-1 BaL virion-associated gp120 (V-gp120) and mAb 412d were loaded onto the same gel, high levels of tyrosine sulfation were detected in both proteins, as indicated by the presence of visible bands at protein concentrations as low as 10 ng per lane, which is close to the lower detection limit of the Western blot technique, with a similar ratio (~1) between the signals obtained with loading controls and anti-Tys antibody (FIG. 2N). In contrast, no signal was detected at any of the concentrations tested for recombinant gp120 produced in HEK293 cells (R-gp120). These results indicate that sulfated tyrosines were present in a major fraction of gp120 produced by primary CD4$^+$ T cells.

Figure 2O:
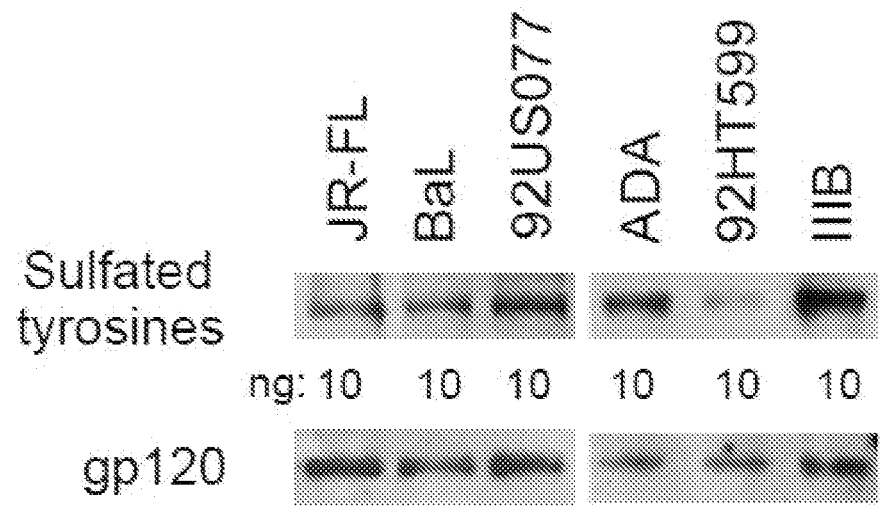

To further verify the efficiency of sulfation in HIV-1 grown in primary CD4$^+$ T cells, gp120 was immunoprecipitated from whole virions of six viral isolates displaying different coreceptor-usage phenotypes, including 3 R5 (BaL, JR-FL, ADA), 2 dual-tropic (92US077, 92HT599) and 1 CXCR4-specific (X4; IIIB). Sulfotyrosine signals were clearly detectable in all cases with 10 ng of immunoprecipitated gp120, indicating a high degree of sulfation efficiency (FIG. 2O). Altogether, these data demonstrate that V2 tyrosine sulfation in gp120 produced in physiologically relevant target cells is highly efficient, in sharp contrast with the inefficiency documented in continuous cell lines.

Figure 3A:
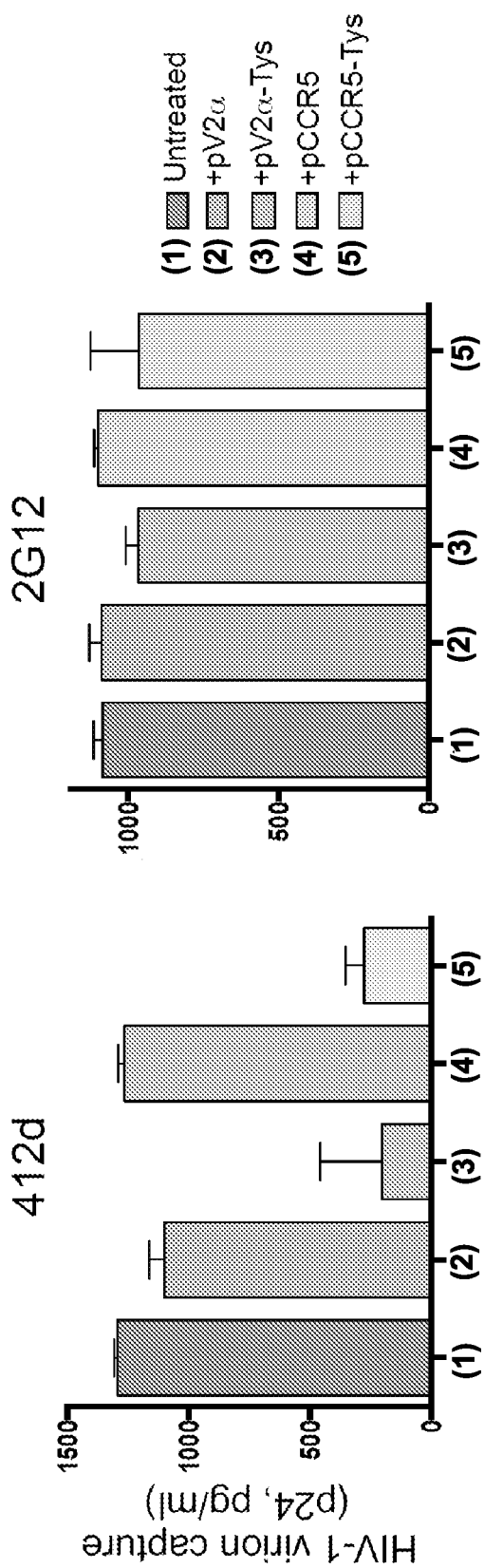

A tyrosine-sulfated V2-loop mimetic peptide interacts with the CCR5-binding site in V3. Having established that the V2 loop of gp120 contains sulfated tyrosines with identical spacing as in the CCR5 N-terminus, it was hypothesized that these modified residues could functionally mimic the CCR5 sulfotyrosines and mediate interaction of V2 with the CCR5-binding site at the base of V3. This interaction is compatible with the recently published crystal structure of a SOSIP soluble gp140 trimer, which shows the V2 tyrosines (173 and 177) positioned in proximity of the CCR5-binding site at short distance from key putative interactive residues (Julien et al. 2013 Science, DOI, 1245625); of note, sulfated tyrosines were not detected in this structure presumably because the recombinant trimer was produced in the epithelial cell line HEK293. Since the tyrosine-sulfated human mAb 412d is believed to interact with the CCR5-binding site mimicking the CCR5 N-terminal domain (Huang et al., *Science* 317, 1930-1934, 2007), the ability of a tyrosine-sulfated 18aa peptide derived from the central region of V2 (pV2α-Tys) to compete with mAb 412d in a virion-capture assay based on antibody-armed immunomagnetic beads was tested Similar to the CCR5 and V2 α-helices, mAb 412d contains two sulfated tyrosines in its antigen-binding loop and competes with tyrosine-sulfated peptides derived from the CCR5 N-terminus (Lam et al., *Bioorg Med Chem* 16, 10113-10120, 2008). Since 412d binds to a CD4-induced (CD4i) epitope, HIV-1 virions (strain BaL) were treated with sCD4 prior to their capture by 412-armed magnetic beads. FIG. 3A shows that pV2α-Tys potently inhibited virion capture by 412d, while its unsulfated counterpart (pV2α) had a limited effect; no inhibition was seen on virion capture by 2G12, a mAb directed to a glycan-dependent epitope on the outer domain of gp120. As further controls, we tested a tyrosine-sulfated peptide derived from the CCR5 N-terminus (pCCR5-Tys), which specifically inhibited 412d-mediated virion capture, while its unsulfated counterpart (pCCR5) had no effect (FIG. 3A).

Figure 3B:
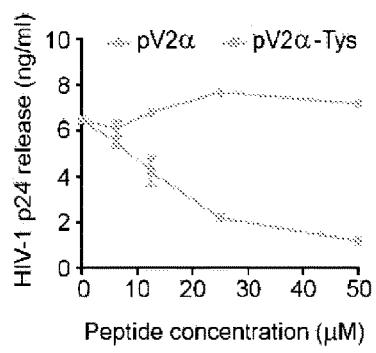
Figure 3C:
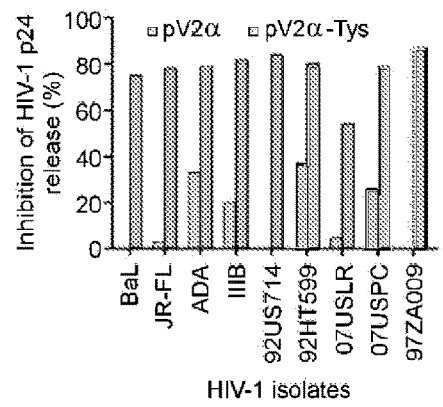
Figure 3D:
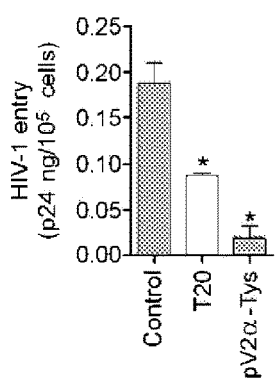
Figure 3E:
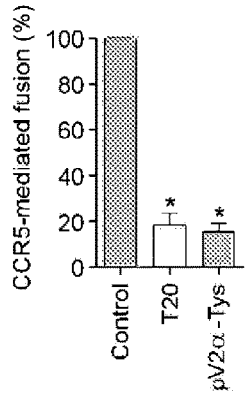
Figure 9:
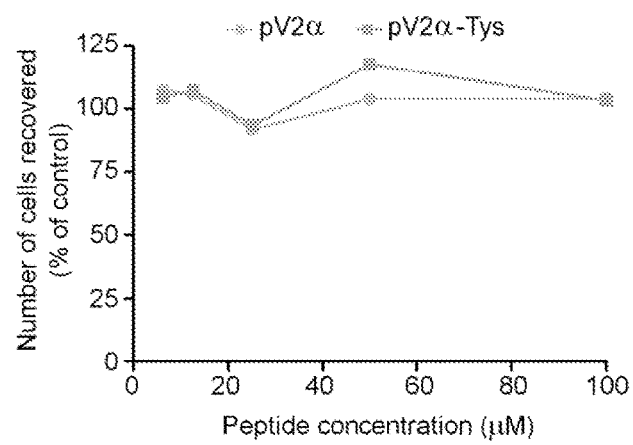
FIG. 9 is a graph illustrating the effect of V2-derived peptides pV2α and pV2α-Tys on viability of primary CD4+ T cells. Purified human peripheral blood CD4+ T cells previously activated in vitro with phytohemagglutinin and IL-2 were treated with each peptide at the indicated concentrations and cultured for 7 days. Cell viability was measured by quantitative counting using timed flow cytometry on a FACSCanto II.
Figure 10:
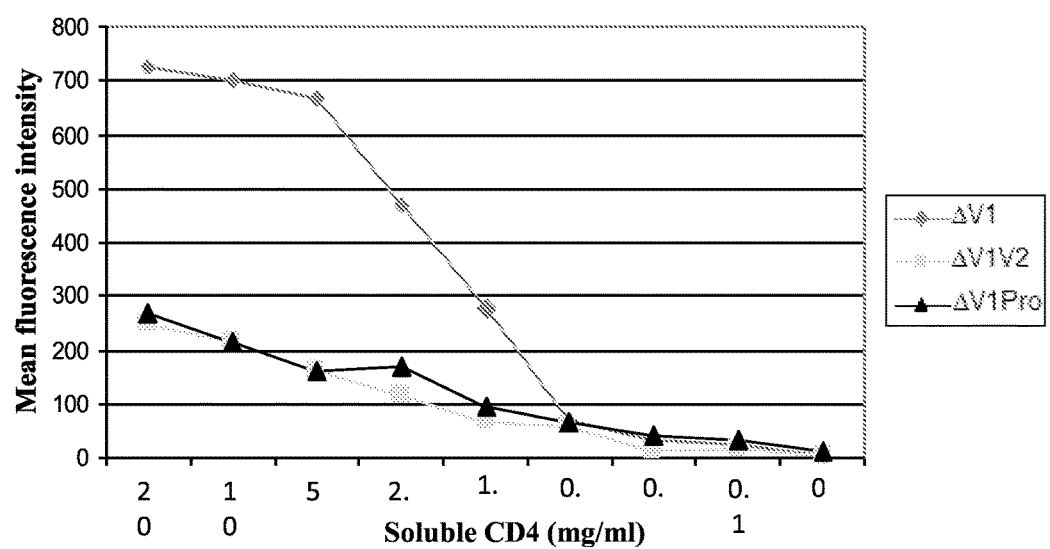
FIG. 10 is a graph illustrating the reduced binding of soluble CD4 to the native HIV-1 envelope carrying a V2 mutation that disrupts the V2 alpha-helix. Wild-type and mutated gp160 envelope glycoproteins of HIV-1 BaL were expressed by recombinant vaccinia vectors on the surface of HeLa. BaL Pro 2.0 contain a proline inserted between Tyr 173 and Ala 174, while BaL Pro 2.8 contains a single proline insertion upstream of the α-helix (between Val169 and Gln170). Binding of soluble CD4 (sCD4) was evaluated by flow cytometry, incubating the gp160 expressing cells with sCD4 at the indicated concentration at room temperature in PBS. After 20 minutes the excess of sCD4 was removed and the binding was evaluated using an anti-CD4 antibody (OKT4).

Since the V2 α-helix and the CCR5 N-terminus interact with the same region at the base of V3, whether sulfated or unsulfated V2-derived peptides could compete with CCR5 and block HIV-1 infection was tested. In acute infection assays performed with primary human CD4$^+$ T cells, peptide pV2α-Tys inhibited infection by HIV-1 BaL in a dose-dependent fashion with a half maximal inhibitory concentration (IC$_{50}$) of 15 μM, while its unsulfated counterpart (pV2α) was ineffective (FIG. 3B). Notably, treatment with either peptide had no negative effects on cell viability (FIG. 9). To assess the breadth of antiviral activity of the two peptides, a panel of 5 primary and 4 laboratory-grown HIV-1 isolates of different coreceptor-usage phenotypes and genetic subtypes were tested. In line with the high degree of conservation of the V2 α-helix, all the isolates were inhibited by pV2α-Tys regardless of their coreceptor-usage specificity; in contrast, the unsulfated peptide showed limited, if any, activity, further confirming the importance of tyrosine sulfation (FIG. 3C). To elucidate the mechanism of HIV-1 inhibition, the effect of pV2α-Tys on HIV-1 entry and CCR5-mediated fusion was tested. FIG. 3D shows that pV2α-Tys inhibited entry of a primary HIV-1 isolate (92HT599) into primary CD4$^+$ T cells with a similar potency as peptide T20, a gp41-derived fusion inhibitor. Moreover, in a soluble CD4-activated fusion assay that selectively evaluates the effects of inhibitors of gp120-CCR5 interaction, pV2α-Tys effectively blocked fusion induced by the HIV-1 BaL envelope (FIG. 3E), demonstrating that the V2 α-helix competes with CCR5 for binding to gp120.

Figure 3F:
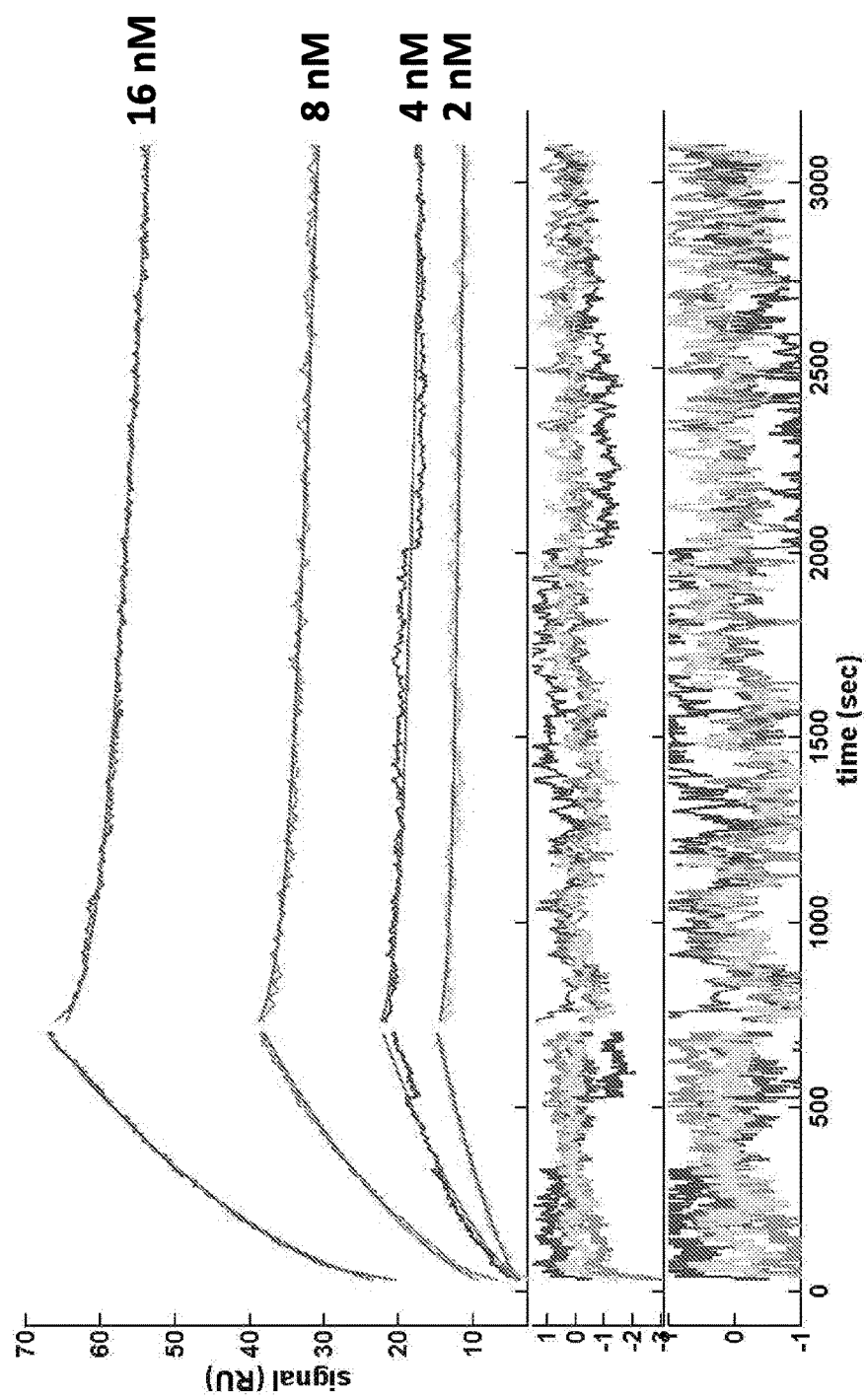

Binding of gp120 to immobilized peptide pV2α as assessed by surface plasmon resonance analysis (FIG. 3F). The biotinylated peptide was bound to a neutravidin-coated CM3 sensor chip and recombinant soluble gp120 (isolate YU2) was flown over the chip in the liquid phase. Experimental binding traces were recorded for gp120 (at the concentration of 2, 4, 8 and 16 nM) binding to 235 RU pV2α at a flow rate of 5 ml/min; best fit traces (solid lines) were derived from modeling with $k_{off}$-$K_D$ distribution. Residuals of the fit, which has an RMSD of 0.62 RU shown twice on different scales to facilitate their critical inspection (lower two graphs). From integration of the main peak of the distribution, binding constants of $K_D$=0.9×10$^{-9}$ M and $k_{off}$=6.4×10$^{-5}$ were derived.

Figure 5:
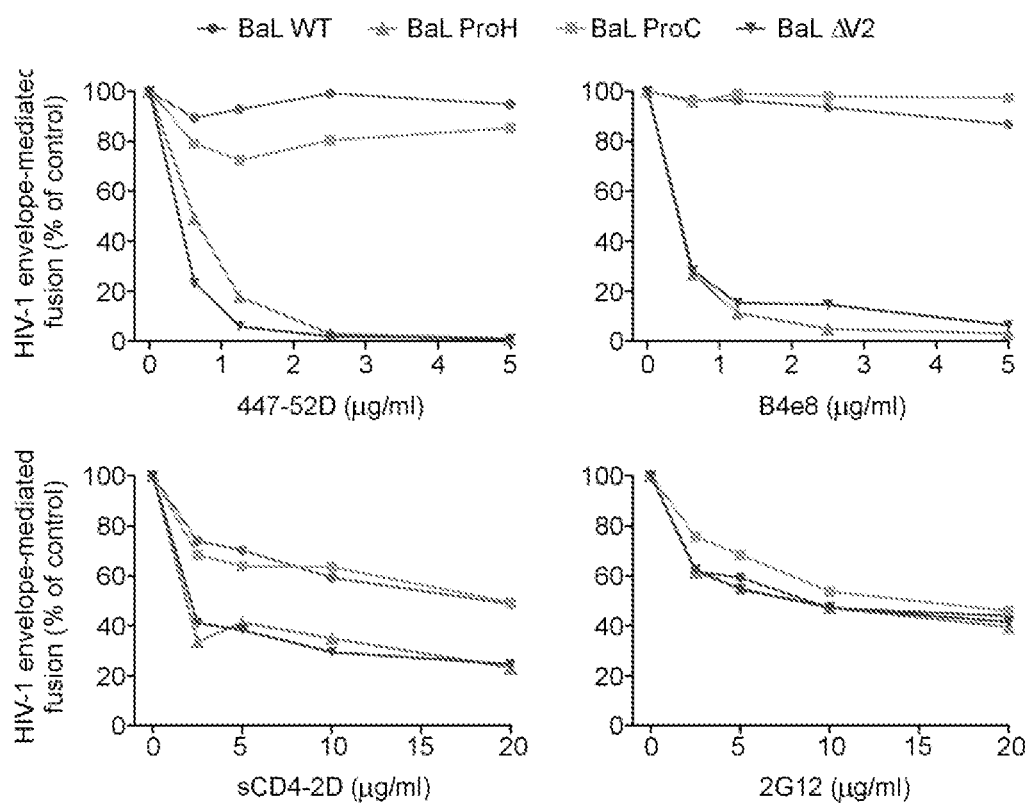
FIG. 5 depicts a series of graphs illustrating that disruption of the V2 α-helix increases HIV-1 sensitivity to neutralization by anti-V3 antibodies and soluble CD4. Effect of anti-gp120 monoclonal antibodies (MAbs) and soluble 2-domain CD4 (sCD4-2D) on envelope-mediated fusion induced by various mutants of HIV-1 BaL. MAbs 447-52D and B4e8 are directed to the tip of the V3 loop; MAb 2G12 is directed to a glycan-dependent epitope on the outer domain of gp120. All the mutants were based on the V1-deleted envelope (wild-type; WT); BaL ProH contained a single proline insertion within the α-helix between Tyr173 and Ala174 that was shown to abolish the helical structure (FIG. 1D); BaL ProC contains a single proline insertion upstream of the α-helix (between Val169 and Gln170); BaL ΔV2 (Δ164-190) was truncated between Thr163 and Tyr191.

Finally, to evaluate the importance of the V2-V3 contact in maintaining the HIV-1 envelope into its native, antibody-protected conformation, a mutant containing a single proline insertion between Tyr173 and Ala174 (BaL ProH) was generated), which was shown to disrupt the V2 α-helix (FIG. 1D), and tested its sensitivity to neutralization. As controls, a mutant containing a proline insertion 3aa upstream of the ProH insertion outside the α-helix was used (BaL ProC), as well as the ΔV2 mutant that lacks the entire helical region. While the WT envelope was essentially insensitive to neutralization by Mabs directed to the V3 crown region (447-52D and B4e8), the ProH mutant was potently inhibited showing a sensitivity equivalent to that of the ΔV2 mutant; by contrast the ProC mutant behaved as the WT (FIG. 5). ProH and ΔV2 also showed an increased sensitivity to soluble CD4, compared to WT and ProC, while no differences were observed with MAb 2G12, which is directed to a glycan-dependent epitope that is constitutively exposed on the surface of the outer domain (FIG. 5). These results document the critical role of the V2 α-helix in establishing intramolecular contact with V3 and show that weakening of this contact disrupts the native conformation of gp120 resulting in increased accessibility to V3 and the CD4-binding site and, thereby, diminished protection from neutralization.

Figure 4:
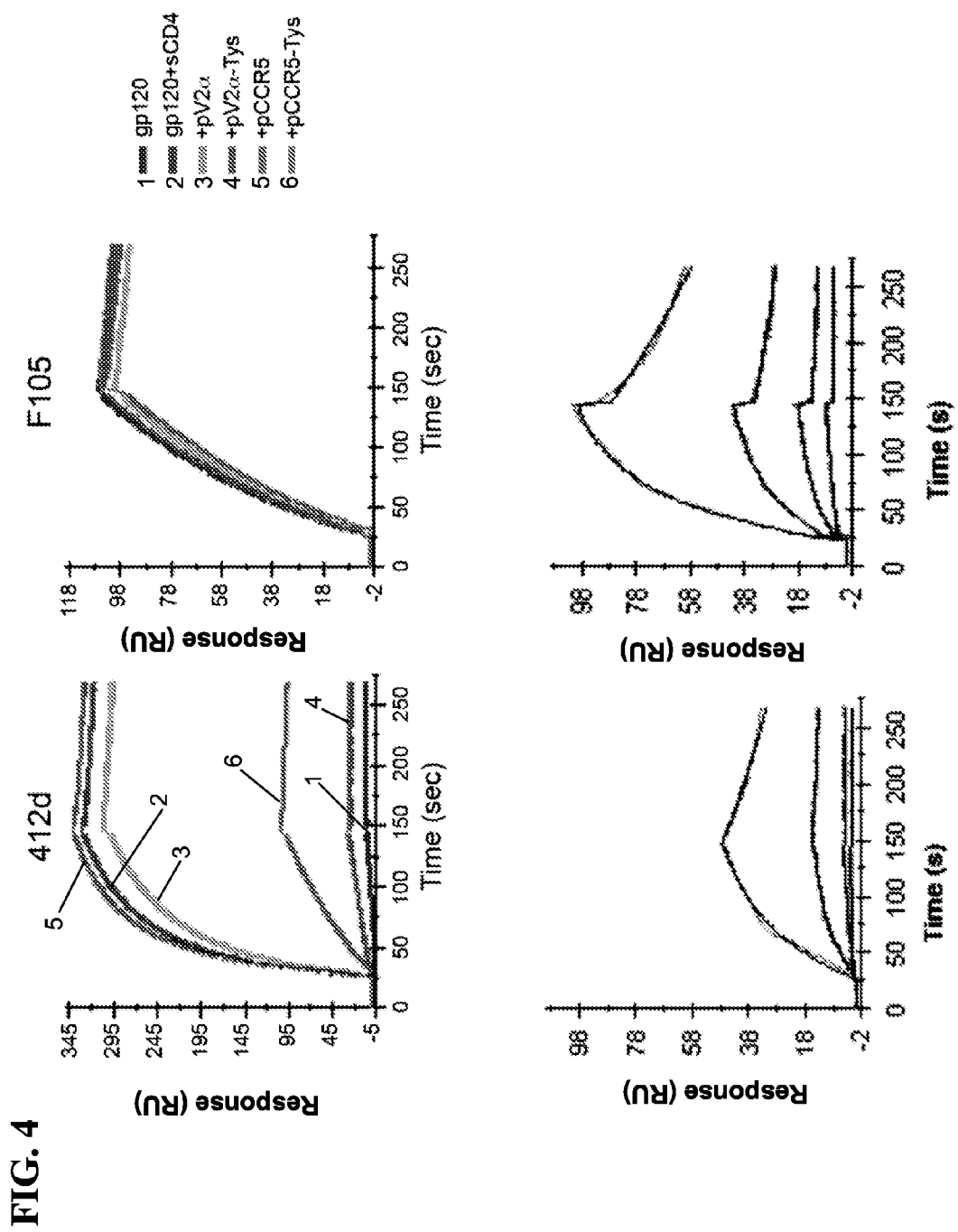
FIG. 4 shows results of (I) Surface plasmon resonance (SPR) analysis of recombinant gp120 (BaL) binding to immobilized mAb 412d and effects of tyrosine-sulfated and unsulfated V2-loop and CCR5 N-terminus (pCCR5-Tys) mimetic peptides; binding to a control mAb (F105, a non-neutralizing mAb directed to the CD4-binding site) was tested in parallel as a control. For binding to 412d, gp120 was treated with 2-domain soluble CD4 (sCD4) at 5 μg/ml. Each peptide was pre-incubated with gp120 at 166 μM. The bottom panels of FIG. 4 illustrate direct binding of gp120 to the immobilized tyrosine sulfated peptide pV2alpha-Tys in the presence (right-side lower panel) or absence (left-side lower panel) of sCD4. Increasing concentrations of gp120 (50 nM to 400 nM) were flown over the immobilized peptide and the signal recorded on a Biacore 3000 instrument.

The interaction of the tyrosine-sulfated V2 peptide with the 412d-binding site was further characterized by surface plasmon resonance (SPR). FIG. 4 shows that pV2α-Tys effectively inhibited binding of surface-bound mAb 412d to CD4-activated gp120, while the unsulfated peptide pV2α had limited effect; likewise, binding to 412d was blocked by the tyrosine-sulfated peptide pCCR5-Tys but not by its unsulfated counterpart. Specificity was confirmed by the lack of inhibition of binding to mAb F105, which is directed to the CD4-binding site (FIG. 4). Altogether, these data indicate that the tyrosine-sulfated central region of V2 interacts with the base of the V3 loop mimicking sulfated domains in the N-terminal domain of CCR5 and in the CDRH3 domain of mAb 412d. Computational models of this interaction were generated using molecular dynamics (MD) simulations in which the tyrosine-sulfated peptide pV2α-Tys was seen to stably interact with the V3 base both when folded in the CCR5-like (helical) and in the 412d-like (extended) conformation (FIGS. 3G,H); electrostatic interactions mediated by the sulfate group of Tys177 contributed a large fraction of the binding energy (FIG. 2E).

Figure 17A:
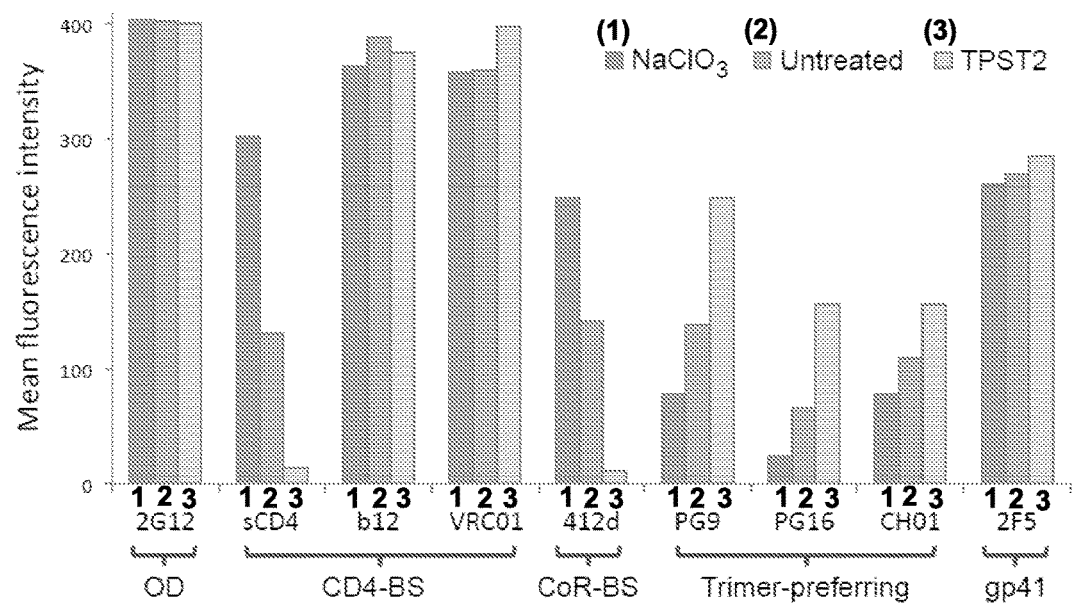
FIGS. 17A-17C illustrate the effect of V2 tyrosine sulfation on gp120 epitope exposure and HIV-1 neutralization.

Tyrosine sulfation in the V2 loop modulates HIV-1 neutralization sensitivity. To assess the functional role of the V2 sulfotyrosines, the effects of modulating the levels of gp120 sulfation on HIV-1 epitope accessibility and neutralization sensitivity was tested. Hypersulfation of V2 tyrosines was achieved by overexpression of the sulfating enzyme, TPST2; inhibition of tyrosine sulfation by treatment with the sulfotransferase inhibitor NaClO$_3$ (see FIG. 2L). Epitope accessibility and neutralization sensitivity were tested on the full-length HIV-1 BaL envelope glycoprotein (gp160) expressed on the surface of transfected HeLa cells. A striking dichotomous effect on the gp120 antigenic profile was observed upon modulation of tyrosine sulfation: inhibition of sulfation markedly increased binding of 412d and soluble CD4, while decreasing recognition by antibodies PG9, PG16 and CH01, which preferentially react with the trimeric, pre-fusion envelope spike; conversely, hypersulfation dramatically reduced binding of 412d and soluble CD4 while increasing recognition by trimer-preferring antibodies (FIG. 17A). Binding of control antibodies directed to the gp120 outer domain (2G12) or CD4-binding site (b12, VRC01), and to gp41 (2F5) was unaffected.

Figure 13:
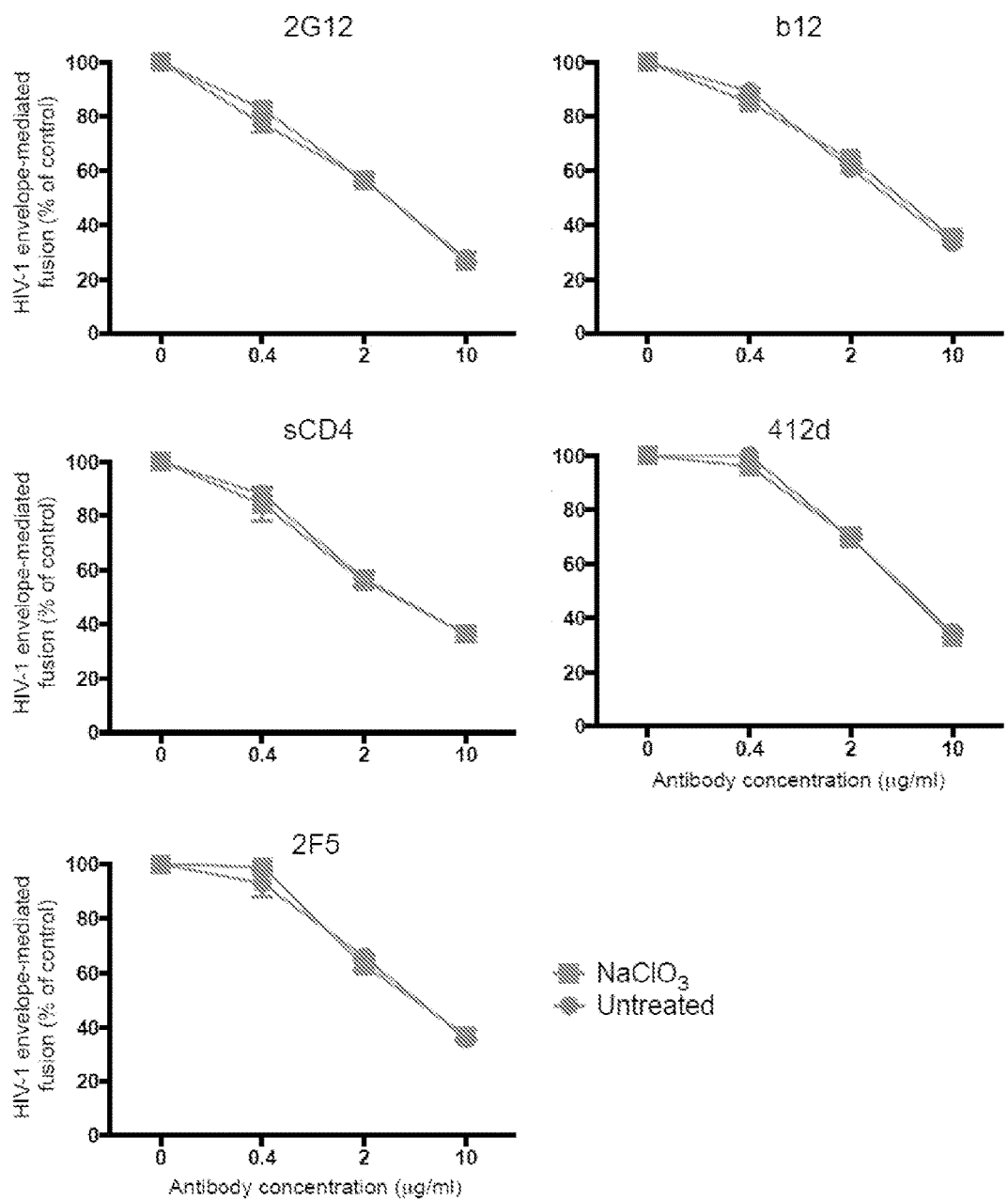
FIG. 13 is a series of graphs illustrating that treatment with NaClO$_3$ does not alter the neutralization sensitivity of HIV-1 BaL ΔV2. The cells were either untreated or pretreated for 72 hrs with the sulfotransferase inhibitor sodium chlorate (NaClO$_3$) at 30 mM. Neutralization was tested on a partially V2-truncated gp160 mutant, HIV-1 BaL ΔV2, which lacks sulfated tyrosines (see FIG. 1B,C). The fusion assay was performed using vaccinia technology with HeLa cells expressing the mutated HIV-1 BaL gp160 as effectors and NIH3T3 cells expressing human CD4 and CCR5 as targets.
Figure 14:
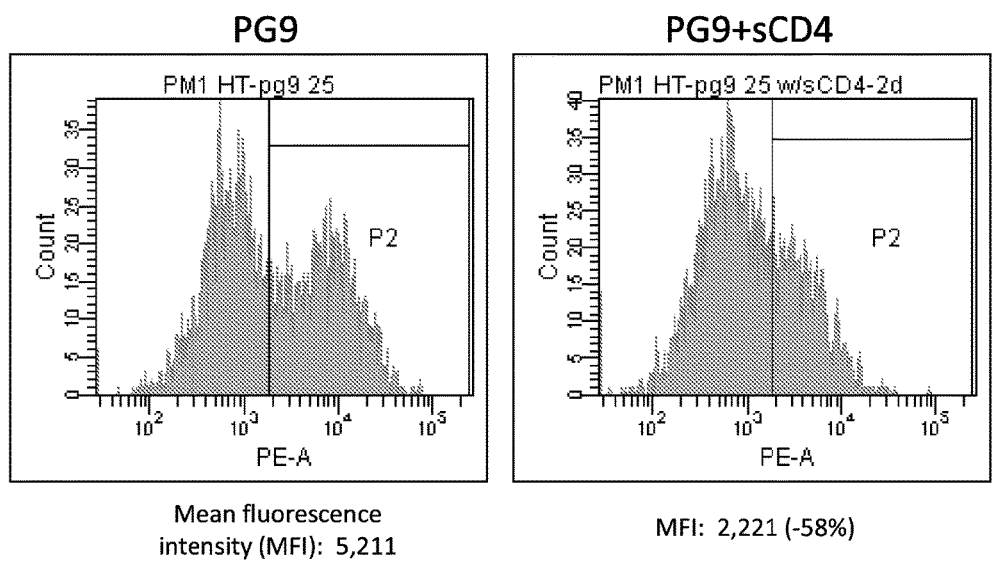
FIG. 14 is a graph illustrating the competition of soluble CD4 with a monoclonal antibody (PG9) directed to the α-helix-containing region of V2. Human T cells (PM1) persistently infected with HIV-1 BaL (R5 isolate) and expressing native envelope trimers on their surface membrane were pre-incubated with control buffer or with soluble CD4 at 5 µg/ml and subsequently stained with monoclonal antibody PG9 and revealed with a phycoerythrin-labeled sheep anti-human IgG secondary antiserum. Flow cytometry analysis was performed on a FACSCanto.
Figure 15:
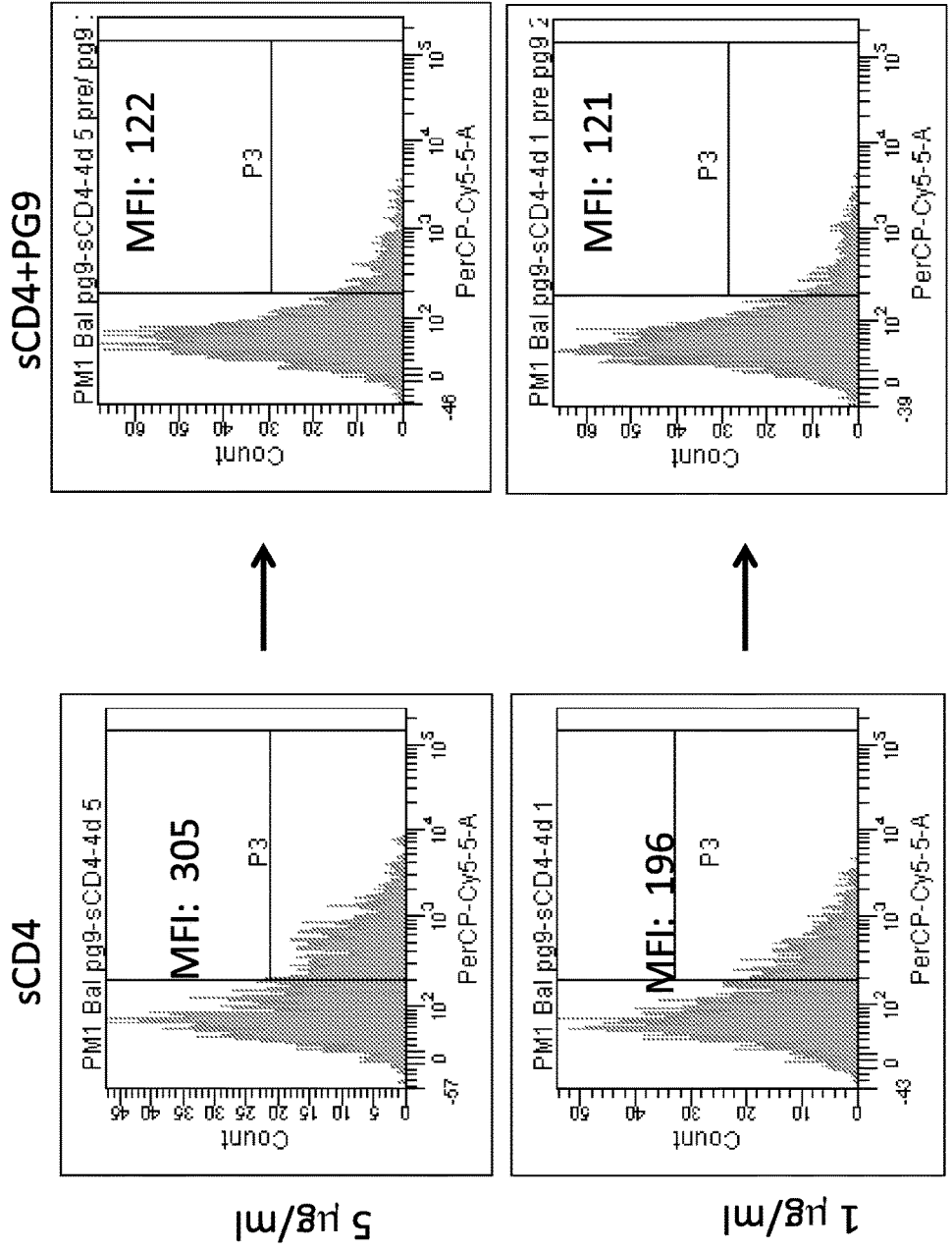
FIG. 15 is a graph illustrating the reciprocal competition of a monoclonal antibody (PG9) directed to the α-helix-containing region of V2 with soluble CD4. Human T cells (PM1) persistently infected with HIV-1 BaL (R5 isolate) and expressing native envelope trimers on their surface membrane were pre-incubated with control buffer or with monoclonal antibody PG9 at 25 µg/ml and subsequently exposed to soluble CD4 (4 domains) and revealed with phycoerythrin-labeled monoclonal antibody OKT4. Flow cytometry analysis was performed on a FACSCanto.
Figure 16:
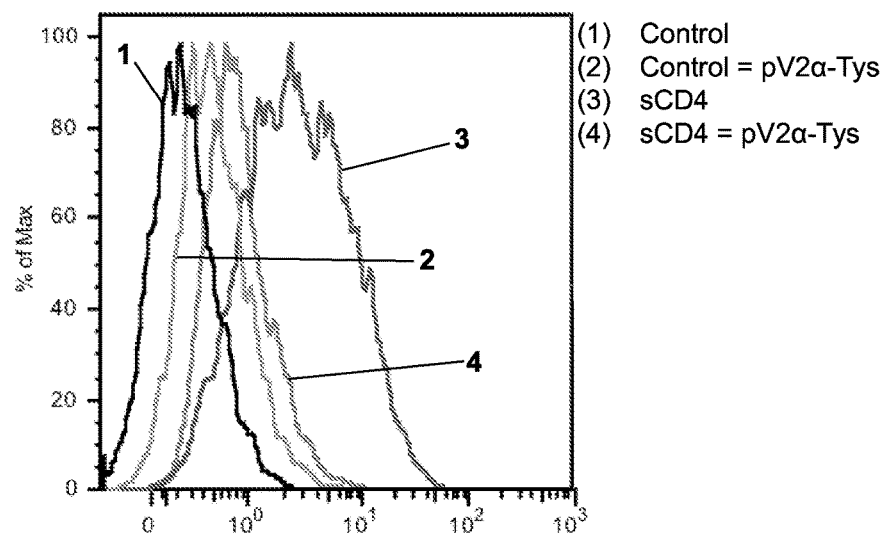
FIG. 16 is a graph illustrating inhibition of soluble CD4 binding to native gp120 by peptide pV2α-Tys. Human T cells (PM1) persistently infected with HIV-1 BaL (R5 isolate) and expressing native envelope trimers on their surface membrane were incubated with soluble CD4 at 10 µg/ml which was either pre-treated or not with peptide pV2α-Tys at 200 µg/ml, and then revealed with phycoerythrin-labeled monoclonal antibody OKT4. Flow cytometry analysis was performed on a FACSCanto.
Figure 17B:
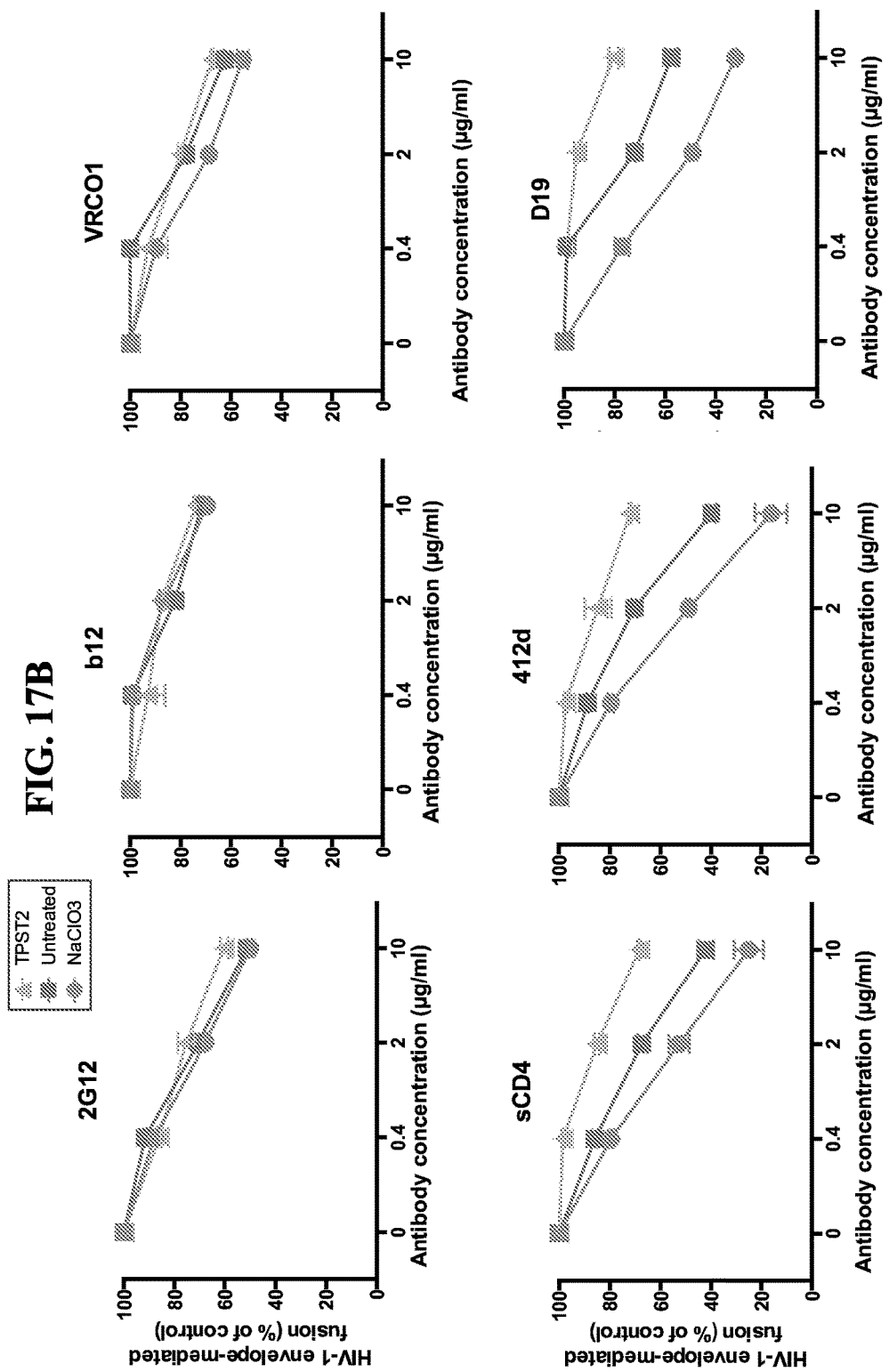
Figure 17C:
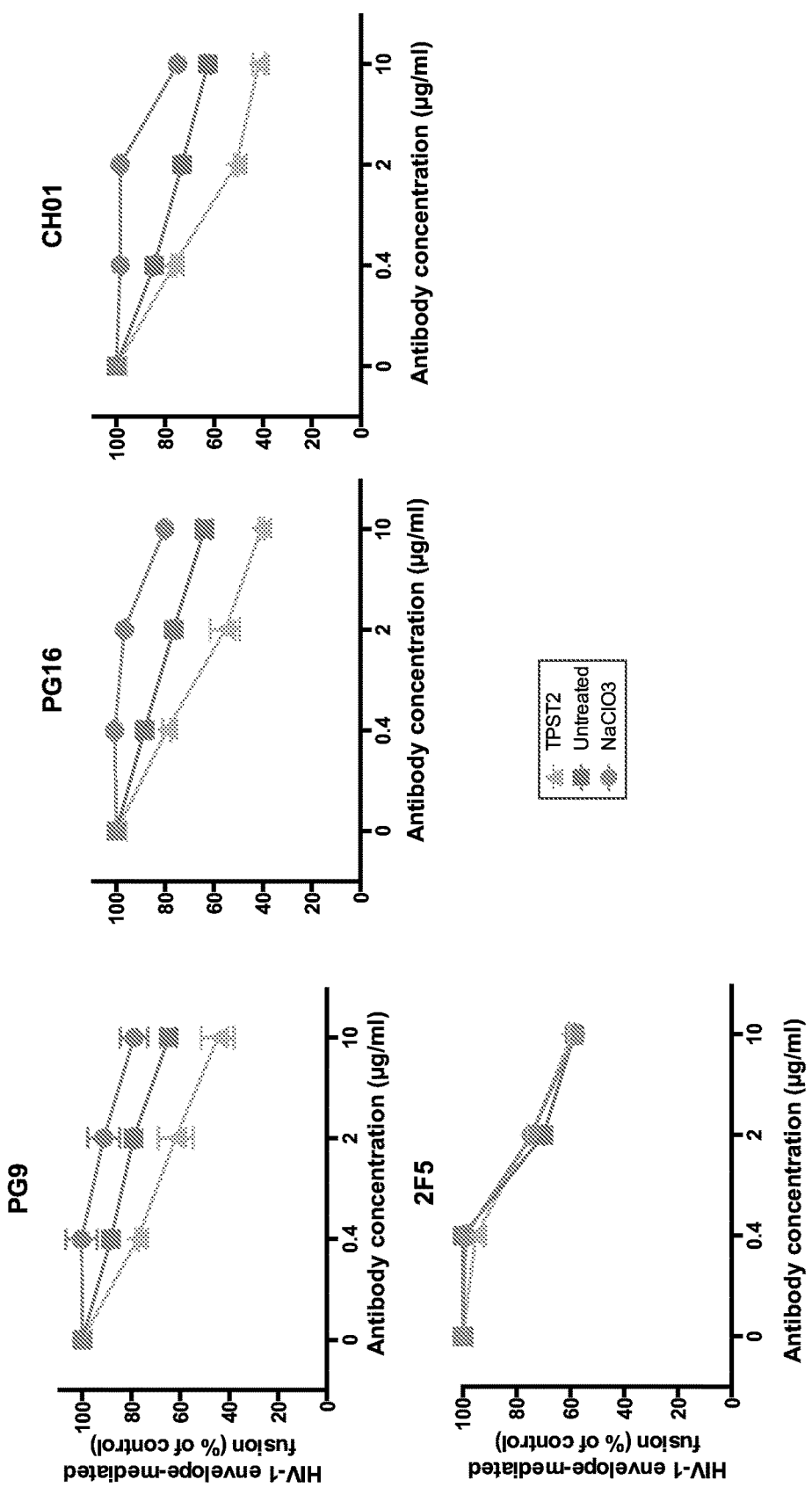

The pattern of epitope exposure observed by flow cytometry was precisely mirrored by the results of neutralization experiments. As illustrated in FIGS. 17B and 17C, inhibition of V2 tyrosine sulfation increased the sensitivity of HIV-1 BaL to neutralization by 412d and sCD4, while decreasing neutralization by the trimer-preferring antibodies PG9, PG16 and CH01. To the contrary, TPST2 overexpression increased resistance to 412d and sCD4, but at the same time it made the virus more sensitive to neutralization by PG9, PG16 and CH01 (FIG. 1B). The neutralizing capacity of control antibodies was minimally affected with only a marginal reduction of 2G12, b12 and VRC01 sensitivity upon TPST2 overexpression, and no detectable effects on 2F5. Of note, as presented above (FIG. 2L and FIG. 2M), treatment with NaClO$_3$ had no adverse effects on gp120 expression and cell viability, nor did it alter the neutralization sensitivity of HIV-1 BaL ΔV2 (FIG. 13), which lacks sulfated tyrosines (FIG. 2L), confirming the specificity of the observed effects. Altogether, these data demonstrate that tyrosine sulfation in V2 plays a critical role in modulating gp120 epitope accessibility and HIV-1 neutralization sensitivity, indicating that the sulfotyrosine-bolstered V2-V3 interaction is important to maintain the envelope spike in its antibody-shielded conformation.

Conclusion

This example provides evidence for the presence of sulfated tyrosines within the V2 loop of the external HIV-1 envelope glycoprotein unit, gp120, and shows that these modified tyrosines play an important role in the functional structuring of the native envelope by mediating interaction between V2 and V3. Tyrosine sulfation is a post-translational modification that occurs in approximately 7% of mammalian proteins and is increasingly recognized as an important modulator of protein-protein interactions (Moore, K. L. (2003) J. Biol. Chem. 278, 24243-24246). Sulfated tyrosines of functional relevance have previously been described in the HIV-1 field in host protein domains that interact with gp120, such as the N-terminal region of CCR5 and other coreceptors (Farzan, M., et al. (1999) Cell 96, 667-676), as well as the antigen-binding regions of antibodies to the coreceptor-binding site such as 412d (Choe, H., et al. (2003) Cell 114, 161-170) and, more recently, of glycan-dependent anti-V2 antibodies such as PG9 and PG16. However, our data document tyrosine sulfation within a viral glycoprotein, as previously reported in envelope glycoproteins of varicella-zoster virus (Farzan, M., et al. (2000) J Biol Chem 275, 33516-33521). It is remarkable that HIV-1 appears to have modeled the central region of V2 after tyrosine-sulfated domains of CCR5 and anti-coreceptor-binding site antibodies in order to establish intramolecular interaction between V2 and the same conserved region of V3 recognized by these host proteins. The results suggest that, upon binding of CD4 to gp120, V2 unclamps from V3, and the sulfated coreceptor N-terminus replaces V2 at the base of V3 to promote subsequent conformational changes that eventually lead to the fusion event. Previous examples of molecular mimicry involving the variable loops of HIV-1 gp120 have been proposed, namely, the α4β7-binding tripeptide (LDV) at the tip of V2, which is identical to the integrin-binding motif of MadCAM, VCAM, and fibronectin (Arthos), and the V3 tip β-hairpins from both CCR5- and CXCR4-tropic HIV-1 isolates, which mimic the coreceptor-binding domains of the respective chemokine ligands, CCL5 and CXCL12 (ref.). However, the purpose of molecular mimicry in these cases would be to optimize interactions with cellular receptors, while the sulfotyrosines in V2 illustrate a new paradigm whereby mimicry of a host protein is exploited to mediate an interaction occurring within the same molecule.

The direct V2-V3 interaction described herein is supported by biological and structural evidence. Functional and antigenic interactions between V2 and V3 have long been recognized, and spatial proximity between the two loops has been documented both by cryoEM studies and by the recently solved crystal structure of a stabilized soluble gp140 trimer (Julien 2013). Although the latter structure lacks sulfated tyrosines, which is not unexpected considering that the protein was produced in HEK293 cells, it is fully compatible with our model because it shows the tyrosine-containing 173-177 segment directly juxtaposed to the CCR5-binding region at the base of V3, with Tyr177 establishing a hydrogen bond with Asn302, which was previously modeled to interact with the homologous sulfotyrosine (Tys14) of CCR5 (Huang et al., (2007) Science 317, 1930-1934). However, the V2-V3 interaction is relatively loose in the SOSIP trimer compared to the CCR5-docking model (Huang, C., et al. (2005) Science 310, 1025-1028), with Tyr173 almost entirely exposed to the solvent and Tyr177 held in a pocket largely through van der Waals contacts. It is unquestionable that the presence of sulfate groups would lead to the formation of strong electrostatic interactions between the V2 tyrosines and the surrounding residues tightening the V2-V3 interface. Thus, the absence of sulfated tyrosines may be one of the reasons why the stabilized SOSIP trimer still displays some phenotypic properties of the open gp120 conformation such as reactivity with certain anti-V3-loop mAbs, efficient binding to monomeric sCD4, and unfavorable ratio (>6-25) between the half-maximal concentrations of trimer-preferring antibodies (PG9, PG16, CH01) required for binding to the synthetic trimer versus neutralization of the homologous virus.

Similar to other post-translational modification like N-linked glycosylation, tyrosine sulfation of gp120 can be remarkably variable in different cells. Indeed, very inefficient gp120 sulfation was found in epithelial cell lines, most likely due to limited expression of tyrosyl sulfotransferases in these cells. This observation has practical implications because epithelial cells lines such as HEK293 are widely used for the production of recombinant gp120 for both structural and biological studies, as well as for pre-clinical and clinical vaccine trials, and neutralization assays based on pseudotyped HIV-1 particles. The low sulfation efficiency detected in epithelial cell lines further emphasizes the need to utilize in vitro protein expression systems capable of producing gp120 with physiologically relevant post-translational modifications. Importantly, however, it was found that in the most important physiological target cells for HIV-1 infection, such as primary human CD4[+] T lymphocytes, gp120 was efficiently sulfated, corroborating the biological relevance of this modification. Furthermore, the altered antigenic profile and neutralization sensitivity induced by modulation of gp120 tyrosine sulfation clearly demonstrates that the sulfated fraction of gp120 is functionally relevant. The results indicate that the sulfotyrosine-bolstered interaction between V2 and V3 represents a critical mechanism whereby HIV-1 constrains gp120 in its energetically unfavorable but antibody-shielded pre-fusion conformation, which facilitates immune evasion. Several considerations point to Tys177, analogous to Tys14 in CCR5, as the most important sulfated tyrosine in V2, while the role of Tys173, corresponding to Tys10 in CCR5, may be less critical. In agreement with this model, Tys177 is extremely conserved across all HIV-1 subtypes, whereas Tys173 shows a somewhat greater variability, being conserved in subtypes A, B and C, but often replaced by histidine in subtypes D, E and F. However, a hallmark of HIV-1 is an extraordinary degree of genetic and phenotypic diversity, which is reflected by a broad range of neutralization sensitivities among primary isolates. Thus, variation at position 173, along with modulation of neighboring amino acid charges which are known to affect the efficiency of tyrosine sulfation, could be some of the mechanisms used by different HIV-1 isolates to finely tune the degree of openness of their envelope structure, balancing the pressure to maintain a high replication fitness with that to elude immunologic control.

These findings provide a further rationale for consideration of the conserved central region of V2 as a vaccine target, emphasizing tyrosine sulfation in this region both as a component of the target epitope(s) and as a modulator of the three-dimensional structure of the region in its tertiary/quaternary interactions. The possible role of V2 as a vaccine target is corroborated by the results of the RV144 trial, the first vaccine to show some efficacy, albeit limited, in preventing HIV-1 transmission, which identified the induction of antibodies to specific V2 aa signatures as a risk correlate (Karasavvas, et al. (2012) AIDS Res Human Retroviruses 28, 1444-1457; Montefiori, D. C., et al. (2012) J Infect Dis 206, 431-441).

Materials and Methods:

The sulfated pV2alpha peptide was obtained commercially and synthesized according to standard protocols (American Peptides, Sunnyvale, Calif.).

Clustal Omega alignment. The alignment of V2 domain from 6 different HIV-1 subtypes (A to F) was performed using all the sequences deposited in the Los Alamos HIV Sequence Database and selecting one sequence for each patient isolate. A total of 191 sequences from subtype A, 3,306 from subtype B, 2,160 from subtype C, 195 from subtype D, 660 from subtype E, and 63 from subtype F were aligned using the Clustal Omega algorithm (Sievers et al., *Mol Syst Biol* 7, 2011). Conservative substitutions were defined according to the standard Clustal parameters.

Secondary structure predictions. Secondary structure predictions were conducted using Agadir (agadir.crg.es/links.jsp), GOR V (gor.bb.iastate.edu), Jufo 9 (meilerlab.org/index.php/servers/), Psi Pred (bioinf.cs.ucl.ac.uk/psipred/), and NNPred (cmpharm.ucsf.edu/~nomi/nnpredict.html).

Molecular representations. VMD (ks.uiuc.edu/Research/vmd/) and Chimera (cgl.ucsf.edu/chimera) were used for three-dimensional visualizations.

Circular dichroism. Far-UV CD spectra were measured and recorded on a Jasco-810 Spectropolarimeter (Jasco Inc., Easton, Md.) equipped with temperature controller. Spectra were recorded using a 0.1 cm quartz cuvette, with scan speed of 100 nm/min, response time of 1 sec, bandwidth of 4 nm, and averaging of 3-5 scans. Peptide concentrations were determined spectrophotometrically in 30% acetonitrile at 280 nm using a molar extinction coefficient of 29,800 $M^{-1}$ $cm^{-1}$. The raw CD data were analyzed using the CDPro software suite (Sreerama et al., *Anal Biochem* 287, 252-260, 2000) using basis sets SP37 and SDP42 to obtain estimates of secondary structure elements. The normalized root-mean-square-difference (NMRSD) of the raw data and calculated curves for both peptides were below 0.038.

Gromacs Molecular Dynamics simulations. Molecular dynamics simulations were performed using Gromacs (v.2.3) (gromacs.org), implemented on a parallel architecture with the GROMOS96 force field. The peptide was constructed using an ab initio structure derived from ROSETTA, and explicitly solvated with TIP3P water molecules and $Na^+$ and $Cl^-$ counterions. Prior to the start of the molecular dynamics portion of the study, the system was minimized using a conjugate-gradient method, followed by slow warming to 310 K in 10 K increments. Each increment ran for 5 psec in order to equilibrate the system at a given temperature. Once the 310 K target temperature was reached, the system was equilibrated for an additional 100 psec. Conformations were obtained at 1 nsec intervals, clustered using an root-mean square (RMS) deviation of 5 Å. Representative structures from the clusters were ranked based on energy, and the structure with the lowest energy was used for further studies.

Ab initio ROSETTA predictions. A portion of the V2 region of gp120 colinear to residues 161-199 of HIV-1 BaL from 10 different gp120 homologs (UniProtKB accession numbers: Q72546, B9VR81, Q7ZB13, B7FCA6, B7UES4, Q9DY10, Q9DSJ4, P89909, Q3HLM4, Q06514) was subjected to 1,024 independent folding trajectories using ROSETTA3 v3.2 (Leaver-Fay et al., *Meth. Enzymol.* 487, 545-574, 2011) with disulfide constraints. The top 5 models for each homolog were pooled and superposed, and the structurally central decoy (the $2^{nd}$ ranking decoy for B7FCA6) was used as a template upon which residues 161-199 of HIV-1 BaL were modeled.

Replica-Exchange Molecular Dynamics. Explicit solvent Replica-Exchange Molecular Dynamics (REMD) simulations were performed on peptide V2α using the NAMD program v.2.8 (Phillips et al., *J Comput Chem* 26, 1781-1802, 2005) on the Biowulf Linux cluster at the NIH, Bethesda, Md. (biowulf.nih.gov). The peptide was constructed as a random coil, and explicitly solvated with TIP3P water molecules and $Na^+$ and $Cl^-$ counterions using the VMD program (Humphrey et al., *J of Mol Graph* 14, 33-38, 1996). Periodic boundary conditions were used and electrostatic interactions were calculated using the Particle-Mesh Ewald summation. A non-bonded term cutoff of 12 Å was used. The CHARMM27 forcefield was used with CHARMM atom types and charges. Prior to the start of the REMD portion of the study, the system was minimized using a conjugate gradient method, followed by slow warming to 310 K in 10 K increments. Each increment ran for 5 psec in order to equilibrate the system at a given temperature. Once the 310 K target temperature was reached, the system was equilibrated for an additional 50 psec at the end of which a total of 40 replicas were run across 40 processors with a temperature range of 300-600 K for a cumulative simulation time of 0.6 msec. Conformations were obtained at 1 nsec intervals, clustered using an root-mean square (RMS) deviation of 5 Å. Representative structures from the clusters were ranked based on energy and the structure with the lowest energy was used for further studies.

FlexPepDock ROSETTA docking. The FlexPepDock simulation (Raveh et al., *Proteins* 78, 2029-2040, 2010) was performed using 2,016 independent trajectories. The V2α-helix-containing peptide (residues 168-185) extracted from the ab initio ROSETTA model was oriented to the V3 base by all atom superposition of Tys173 and Tys177 to Tys100 and Tys100C of mAb 412d in the co-crystal structure with gp120 (Hu et al., *J Virol* 85, 2741-2750, 2011).

Isothermal-isobaric Molecular Dynamics. The pV2α peptide modeled by REMD was positioned using information from the gp120 crystal structure with bound mAb 412d (PDB ID 2QAD), a model of the CCR5 N-terminal domain docked to gp120 (Hu et al., *J Virol* 85, 2741-2750, 2011) and the FlexPepDock results (Raveh et al., *Proteins* 78, 2029-2040, 2010) of ROSETTA3(Leaver-Fay et al., *Meth. Enzymol.* 487, 545-574, 2011). Simulations were carried out as described in the REMD section with the exception that once the 310 K target temperature was reached, systems were not split into replicas and dynamics was performed under isothermal-isobaric conditions. Forcefield parameters for sulfotyrosine were taken from modified CHARMM27 topologies. Langevin dynamics were used to maintain temperature and a modified Nose-Hoover Langevin piston was used to control pressure. Production data was gathered for 100 nsec at 1 nsec intervals.

LigPlot. Trajectories were analyzed using LigPlot by outputting snapshot structures from the trajectories at 1 nsec intervals and computing NACCESS-enhanced LigPlots for each snapshot. The text output was compiled, and the frequencies of observed interactions were used to compare the trajectories. A single view of the trajectory was computed by averaging the snapshots using a custom script in VMD. Following averaging, side chains were reconstructed using the idealize function of Rosetta. The averaged structures were also analyzed with LigPlot. The LigPlot diagram in FIG. 2h is taken from the same snapshot as the 3D images in FIGS. 2E-G.

Detection of sulfated tyrosines by Western blot. To evaluate the presence of sulfated tyrosines in gp120, virus stocks produced in primary human CD4$^+$ T cells were first incubated with 2 μg/tube of a specific anti HIV-1 gp120 mAb (VRC01) for 1 h at room temperature, then with magnetic beads coated with protein G (Invitrogen) under continuous rotation for 1 h at 4° C. The beads were washed three times with PBS, and the samples were resolved by SDS electrophoresis and immunoblotted as previously described (Auerbach et al., *Proc Natl Acad Sci USA* 109, 9569-9574, 2012) with a mAb specific for sulfated tyrosines (clone Sulfo-1C-A2, EMD Millipore) or with an anti-gp120 mAb (clone b24). Wild-type and mutated gp160 envelope glycoproteins of HIV-1 BaL were expressed by recombinant vaccinia vectors on the surface of HeLa or HEK293 cells as previously described (Nussbaum, et al., *J Virol* 68, 5411-5422, 1994). The mutants included BaL ΔV2 (Δ164-190), BaL Y173F, BaL Y177F and BaL Y173F/Y177F cleavable gp160. For immunoprecipitation, 2×10$^6$/cells were incubated for 1 h at room temperature with 2 μg/tube of a specific anti HIV-1 gp120 (VRC01), washed 3 times in PBS and lysed with RIPA buffer for 10 minutes on ice. After centrifugation, the cleared supernatant was incubated with magnetic beads coated with protein G (Invitrogen) under continuous rotation for 1 h at 4° C. The beads were washed 3 times with PBS and the samples were resolved by SDS electrophoresis and immunoblotted as previously described (Auerbach et al., *Proc Natl Acad Sci USA* 109, 9569-9574, 2012) with anti-sulfated tyrosine (clone Sulfo-1C-A2, EMD Millipore) or anti-gp120 (clone b24) antibodies. For Western blot analysis of mAb 412d, the loading control was a mAb specific for human IgG (clone HP6045, Life Technologies). To detect sulfated tyrosines in virion-associated gp120, infectious viral stocks from different isolates produced in primary human CD4$^+$ T cells were first incubated with a specific anti-HIV-1 gp120 mAb (VRC01, 2 μg/sample) for 1 hr at room temperature, then washed, lysed and immuno-precipitated with magnetic beads and treated as described above for cell-surface expressed gp120.

Detection of sulfated tyrosines by metabolic labeling. For experiments of metabolic labeling, cells expressing WT or ΔV2 (Δ164-190) HIV-1 BaL gp160 were labeled for 18 hrs with either free [$^{35}$S]sulfate (0.25 mCi/ml) or with [$^{35}$S]cysteine/[$^{35}$S]methionine (0.1 mCi/ml) (both by Perkin Elmer) by incubation in sulfate-free MEM medium (Mediatech) or cysteine/methionine-free DMEM medium (Life Technologies), respectively. Metabolically-labeled cells were washed repeatedly with cold PBS, lysed, and cleared by high-speed centrifugation, and the cell lysate was treated with mAb VRC01 for 3 h under continuous rotation and subsequently incubated overnight with agarose beads coupled with protein-G (Sigma). The beads were then washed 3 times with ultrapure water and treated with deglycosylating enzymes using a commercial kit (ProZyme) to exclude incorporation of [$^{35}$S]sulfate into glycans. Deglycosylation was confirmed by Western blot. After treatment, the proteins were analyzed by autoradiography after SDS electrophoresis.

Modulation of tyrosine sulfation levels by TPST2 overexpression or sodium chlorate treatment. Overexpression of the full-length TPST2 gene was achieved by transfection with a mammalian expression vector as previously reported (Choe and Farzan, *Methods in Enzymology*, 461: 147-170, 2009). Treatment with sodium chlorate at 30 mM was started 18 hrs after transfection with gp160-expressing vectors and continued throughout the culture period until the cells were harvested and washed for the fusion assay.

Surface plasmon resonance. Recombinant gp120 from HIV-1 BaL (at 100 nM) obtained from the NIH AIDS Reagent Program was pre-incubated with or without a 2-fold molar excess of two-domain sCD4 (at 200 nM) and passed over a Biacore CM5 sensor surface in the presence or absence of the indicated peptides (at 166 μM) for 2 min at 25 μl/min in HBS supplemented with 3 mM EDTA and 0.005% Tween-20 followed by a 2 min dissociation phase using a Biacore 3000 biosensor (Biacore, Inc.). Surfaces were regenerated after each cycle by a brief injection of 4.5M MgCl$_2$.

HIV-1 virion-capture assay. The virion-capture assay was performed as previously described (Auerbach et al., *Proc Natl Acad Sci USA* 109, 9569-9574, 2012) using protein-G-coated immunomagnetic beads (Invitrogen) armed with mAb 412d or 2G12 (each at 2.5 μg/10$^7$ beads/tube). The HIV-1 BaL stock, grown in primary CD4$^+$ T cells, was pre-treated with sulfated or unsulfated peptides at 50 μM prior to capture by the armed beads. For 412d, the viral stock was also pre-treated with soluble CD4 (5 μg/ml) in order to expose the antibody-binding epitope (Huang et al., *Science* 317, 1930-1934, 2007) and then treated with peptides pV2α-Tys or pV2α at 50 μM prior to capture with the armed beads.

HIV-1 isolates, infection, entry and cell viability assays. Details about the HIV-1 isolates used in the this study, the infection assay, the entry assay and the cell viability assay have been reported previously (Auerbach et al., *Proc Natl Acad Sci USA* 109, 9569-9574, 2012).

Fusion assays. The HIV-1 envelope-mediated fusion assays were performed as previously described (Lusso et al., *J Virol* 79, 6957-6968, 2005). For the standard assay HEK293T infected with recombinant vaccinia viruses expressing wild-type or mutated gp160 were used as effectors; target cells were NIH3T3 expressing human CD4 and CCR5. For the sCD4-activated assay, Hela cells infected with a recombinant vaccinia virus expressing wild-type cleavable gp160 were used as effectors and Hos-CCR5 (CD4-negative) cells as targets. The effector cells were pre-incubated with antibodies or sCD4 at the indicated concentrations for 20 min at room temperature prior to coculture with target cells for 2 hrs at 37° C.

Statistical analysis. Statistical analysis was conducted by using the Prism 5 software for Windows. An unpaired two-tailed t test was used to compare differences between cells untreated (designated as control) or treated with different inhibitors.

Example 2

The pV2α Peptide Binds to Soluble CD4

This example illustrates that a peptide including gp120 positions 168-185 binds to CD4. Binding of soluble CD4 (sCD4) or antibody 48d was evaluated by flow cytometry on wild-type and mutated gp160 envelope glycoproteins of HIV-1 BaL. The envelope glycoproteins were expressed by recombinant vaccinia vectors on the surface of HeLa cells. BaL Pro 2.0 contain a proline inserted between Tyr 173 and Ala 174, while BaL Pro 2.8 contains a single proline insertion upstream of the α-helix (between Val169 and Gln170). Binding of soluble CD4 (sCD4) was evaluated by incubating the gp160 expressing cells with sCD4 at the indicated concentration at room temperature in PBS. After 20 minutes the excess of sCD4 was removed and the binding was evaluated using an anti-CD4 antibody (OKT4). Binding of soluble 48d in the presence or absence of sCD4 was evaluated by incubating the gp160 expressing cells with 48d at the indicated concentration at room temperature in PBS. After 20 minutes the excess of 48d was removed and the binding was evaluated using an anti-human IgG polyclonal sera.

Figure 12:
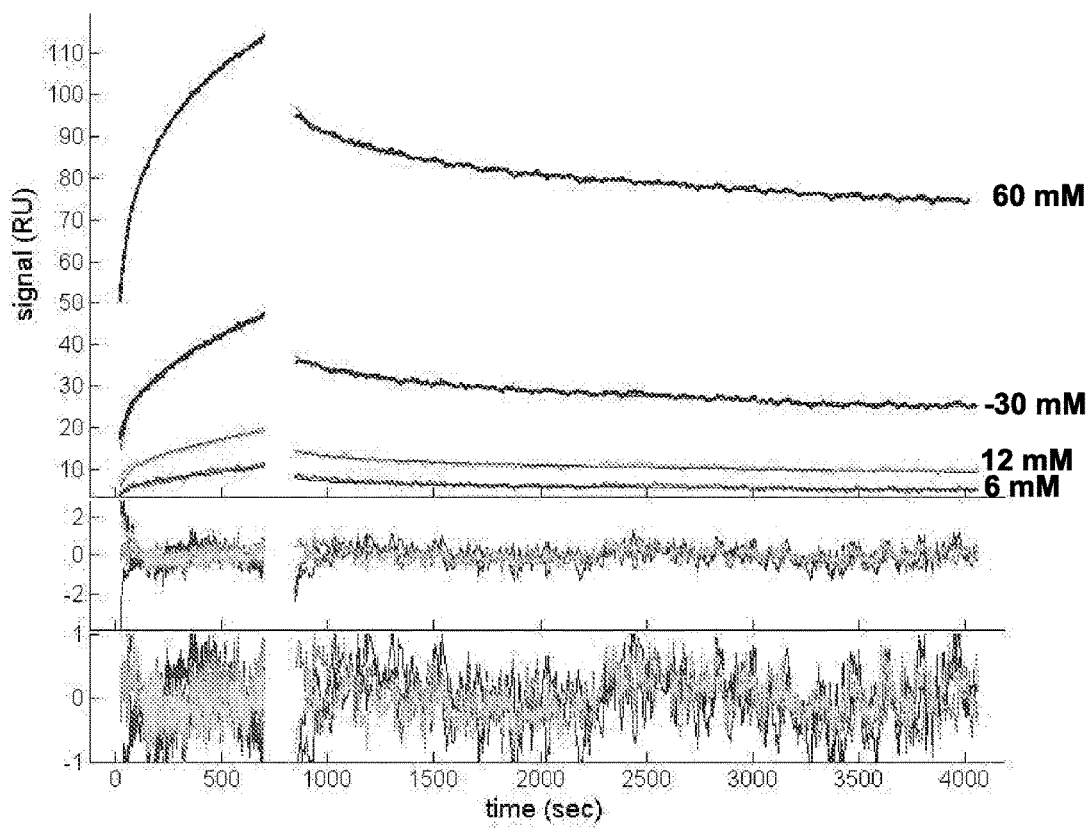
FIG. 12 is a graph illustrating binding of recombinant soluble CD4 to peptide pV2α. The biotinylated peptide was bound to a neutravidin-coated CM3 sensor chip and recombinant soluble CD4 was flown over the chip in the liquid phase. Experimental binding traces were recorded for sCD4 (at the concentration of 6, 12, 30, and 60 mM) binding to 235 RU pV2α at a flow rate of 5 ml/min; best fit traces (red lines) were derived from modeling with $k_{off}$-$K_D$ distribution. (Lower graphs) Residuals of the fit, which has an rmsd of 0.47 RU shown twice on different scales to facilitate their critical inspection. From integration of the main peak of the distribution, binding constants of $K_D$=4.×10$^{-3}$ M and $k_{off}$=1.3×10$^{-2}$ s$^{-1}$ were derived.

Binding of recombinant soluble CD4 to peptide pV2α was evaluated by surface plasmon resonance (FIG. 12). The biotinylated peptide was bound to a neutravidin-coated sensor chip and recombinant soluble CD4 was flown over the chip in the liquid phase. Experimental binding traces were recorded for sCD4 (at the concentration of 6, 12, 30, and 60 mM) binding to 235 RU pV2α at a flow rate of 5 ml/min; best fit traces (red lines) were derived from modeling with $k_{off}$-$K_D$ distribution.

Example 3

Immunogenicity of the Pv2α and pV2α-Tys Peptides

This example illustrates that the pV2α and pV2α-Tys peptides are immunogenic. Rabbits were immunized with the pV2α or pV2α-Tys peptide and the resulting sera collected for testing for binding to the pV2α or pV2α-Tys peptide. All sera were heat-inactivated and tested in standard ELISA tests at 1:200 final dilution. The results show that both the pV2α and pV2α-Tys peptides induced an immune response (FIG. 18).

Example 4

HIV-1 Patients have V2α-Helix Specific Antibodies

This example issulstrates that HIV-1 patients produce antibodies that specifically bind to the V2α-Helix. Sera from HIV patients was collected and tested for binding to the pV2α peptide. All sera were heat-inactivated and tested in standard ELISA tests at 1:50 final dilution. As shown in FIG. 19, sera from several different patients has specific binding activity for the pV2α peptide. Further the specificity of this interaction was tested by testing sera from HIV-1-infected individuals contain antibodies that recognize the folded V2 peptide on binding to a linear peptide bound to plastic. Serum from five different HIV-1 patients was tested for binding to the pV2α peptide in folded (pV2α-biotin-captured) or linear (unfolded; pV2α plastic-bound) form. Human sera were heat-inactivated and tested in standard ELISA tests at 1:50 final dilution. FIG. 20 shows that the sera from these patients had more specific binding activity for the folded peptide that the unfolded peptide.

Example 5

The pV2α-Tys Peptide Induces a Neutralizing Immune Response

This example illustrates that the pV2α-Tys peptide induces a neutralizing immune response to HIV-1 gp120. A rabbit was immunized with a KLH-conjugated pV2α-Tys peptide and serial dilutions of the resulting sera tested for neutralization of HIV-1 envelope mediated fusion according to known methods (Lusso et al., J. Virol., 79, 6957-6969, 2005) Immunization was carried out using the mighty quick protocol by Pocono Farms and Laboratory. The immune serum tested was obtained from the 3rd bled performed 8 weeks after the first inoculation. The pre-immune serum from the same animal was tested in parallel as a control. Sera were heat-inactivated prior to use. The fusion assay was performed using HEK293 cells expressing WT HIV-1 BaL gp160 as effectors and NIH3T3 cells expressing human CD4 and CCR5 as targets. The effector cells were pre-incubated with rabbit sera at the indicated dilutions for 20 min at room temperature prior to co-culture with target cells for 2 hours at 37° C. The extent of fusion was detected by colorimetric assay for beta-galactosidase activity. As shown in FIGS. 21A and 21B, immune serum neutralized HIV-1 envelope mediated fusion compared to pre-immune fusion, but pre-immune serum did not.

Example 6

Treatment of HIV in a Human Subject

This example describes a particular method that can be used to treat HIV in a human subject by administration of one or more of the disclosed HIV neutralizing peptides or a sulfated HIV-1 envelope protein or immunogenic fragment thereof or a nucleic acid molecule encoding such molecules, to treat a subject with HIV infection. Although particular methods, dosages, and modes of administrations are provided, one skilled in the art will appreciate that variations can be made without substantially affecting the treatment.

Based upon the teaching disclosed herein, HIV, such as HIV type 1 (HIV-1), can be treated by administering a therapeutically effective amount of an HIV neutralizing peptide thereby inhibiting HIV infection, replication or a combination thereof.

Briefly, the method can include screening subjects to determine if they have HIV, such as HIV-1. Subjects having HIV are selected. In one example, subjects having increased levels of HIV antibodies in their blood (as detected with an enzyme-linked immunosorbent assay, Western blot, immunofluorescence assay, or nucleic acid testing, including viral RNA or proviral DNA amplification methods are selected. In one example, a clinical trial would include half of the subjects following the established protocol for treatment of HIV (such as a highly active antiretroviral therapy). The other half would follow the established protocol for treatment of HIV (such as treatment with highly active antiretroviral compounds) in combination with administration of the agents including HIV neutralizing peptides or a sulfated HIV-1 envelope protein or immunogenic fragment thereof or a nucleic acid molecule encoding such molecules (as described above). In another example, a clinical trial would include half of the subjects following the established protocol for treatment of HIV (such as a highly active antiretroviral therapy). The other half would receive an HIV neutralizing peptides or a sulfated HIV-1 envelope protein or immunogenic fragment thereof or a nucleic acid molecule encoding such molecules.

Screening Subjects

In particular examples, the subjects are first screened to determine if they have HIV. Examples of methods that can be used to screen for HIV include a combination of measuring a subject's CD4+ T cell count and the level of HIV in serum blood levels.

In some examples, HIV testing consists of initial screening with an enzyme-linked immunosorbent assay (ELISA) to detect antibodies to HIV, such as to HIV-1. Specimens with a nonreactive result from the initial ELISA are considered HIV-negative unless new exposure to an infected partner or partner of unknown HIV status has occurred. Specimens with a reactive ELISA result are retested in duplicate. If the result of either duplicate test is reactive, the specimen is reported as repeatedly reactive and undergoes confirmatory testing with a more specific supplemental test (e.g., Western blot or an immunofluorescence assay (IFA)). Specimens that are repeatedly reactive by ELISA and positive by IFA or reactive by Western blot are considered HIV-positive and indicative of HIV infection. Specimens that are repeatedly ELISA-reactive occasionally provide an indeterminate Western blot result, which may be either an incomplete antibody response to HIV in an infected person, or nonspecific reactions in an uninfected person. IFA can be used to confirm infection in these ambiguous cases. In some instances, a second specimen will be collected more than a month later and retested for subjects with indeterminate Western blot results. In additional examples, nucleic acid testing (e.g., viral RNA or proviral DNA amplification method) can also help diagnosis in certain situations.

The detection of HIV in a subject's blood is indicative that the subject has HIV and is a candidate for receiving the therapeutic compositions disclosed herein. Moreover, detection of a CD4+ T cell count below 350 per microliter, such as 200 cells per microliter, is also indicative that the subject is likely to have HIV.

Pre-screening is not required prior to administration of the therapeutic compositions disclosed herein.

Pre-Treatment of Subjects

In particular examples, the subject is treated prior to administration of a therapeutic agent that includes one or more of the disclosed HIV neutralizing peptides or a nucleic acid molecule encoding the peptide. However, such pre-treatment is not always required, and can be determined by a skilled clinician. For example, the subject can be treated with an established protocol for treatment of HIV (such as a highly active antiretroviral therapy).

Administration of Therapeutic Compositions

Following subject selection, a therapeutic effective dose of the H HIV neutralizing peptides or a sulfated HIV-1 envelope protein or immunogenic fragment thereof or a nucleic acid molecule encoding such molecule is administered to the subject (such as an adult human or a newborn infant either at risk for contracting HIV or known to be infected with HIV). For example, the methods can include administering an HIV neutralizing peptide including the amino acid sequence of gp120 positions 171-178 according to the HXB2 numbering system and corresponding to the amino acid positions in the amino acid sequence set forth as SEQ ID NO: 1; wherein the HIV neutralizing peptide includes a first sulfated tyrosine at position 173, a second sulfated tyrosine at position 177, or both a first sulfated tyrosine at position 173 and a second sulfated tyrosine at position 177, at most four additional amino acid substitutions compared to a wild-type HIV-1 gp120; no more than 50 amino acids in length; and wherein the peptide is neutralizing. Additional agents, such as anti-viral agents, can also be administered to the subject simultaneously or prior to or following administration of the disclosed agents. Administration can be achieved by any method known in the art, such as oral administration, inhalation, intravenous, intramuscular, intraperitoneal, or subcutaneous.

The amount of the composition administered to prevent, reduce, inhibit, and/or treat HIV or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., HIV) in a subject without causing a substantial cytotoxic effect in the subject. An effective amount can be readily determined by one skilled in the art, for example using routine trials establishing dose response curves. In addition, particular exemplary dosages are provided above. The therapeutic compositions can be administered in a single dose delivery, via continuous delivery over an extended time period, in a repeated administration protocol (for example, by a daily, weekly, or monthly repeated administration protocol). In one example, therapeutic agents that include one or more HIV neutralizing peptides or a nucleic acid molecule encoding the peptide are administered intravenously to a human. As such, these compositions may be formulated with an inert diluent or with an pharmaceutically acceptable carrier.

Administration of the therapeutic compositions can be taken long term (for example over a period of months or years).

Assessment

Following the administration of one or more therapies, subjects having HIV (for example, HIV-1) can be monitored for reductions in HIV levels, increases in a subjects CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 7

Treatment of Subjects

This example describes methods that can be used to treat a subject that has or is at risk of having an infection from HIV that can be treated by eliciting an immune response, such as a neutralizing antibody response to HIV. In particular examples, the method includes screening a subject having, thought to have or at risk of having a HIV infection. Subjects of an unknown infection status can be examined to determine if they have an infection, for example using serological tests, physical examination, enzyme-linked immunosorbent assay (ELISA), radiological screening or other diagnostic technique known to those of skill in the art. In some examples, subjects are screened to identify a HIV infection, with a serological test, or with a nucleic acid probe specific for a HIV. Subjects found to (or known to) have a HIV infection can be administered an immunogenic composition including a disclosed HIV neutralizing peptides or a sulfated HIV-1 envelope protein or immunogenic fragment thereof or a nucleic acid molecule encoding such molecule that can elicit an antibody response to HIV. Subjects may also be selected who are at risk of developing HIV for example, subjects exposed to HIV.

Subjects selected for treatment can be administered a therapeutic amount of the disclosed HIV neutralizing peptides or a sulfated HIV-1 envelope protein or immunogenic fragment thereof or a nucleic acid molecule encoding such molecule. The HIV neutralizing peptides or a sulfated HIV-1 envelope protein or immunogenic fragment thereof can be administered at doses of 1 µg/kg body weight to about 1 mg/kg body weight per dose, such as 1 µg/kg body weight-100 µg/kg body weight per dose, 100 µg/kg body weight-500 µg/kg body weight per dose, or 500 µg/kg body weight-1000 µg/kg body weight per dose. However, the particular dose can be determined by a skilled clinician. The HIV neutralizing peptide can be administered in one or several doses, for example continuously, daily, weekly, or monthly. When administered sequentially the time separating the administration of the antigen can be seconds, minutes, hours, days, or even weeks.

The mode of administration can be any used in the art. The amount of agent administered to the subject can be determined by a clinician, and may depend on the particular subject treated. Specific exemplary amounts are provided herein (but the disclosure is not limited to such doses).

It will be apparent that the precise details of the methods or compositions described may be varied or modified without departing from the spirit of the described embodiments. We claim all such modifications and variations that fall within the scope and spirit of the claims below.

---

We claim:

1. A method of making a sulfated HIV-1 envelope protein or immunogenic fragment thereof for use in stimulating an immune response against HIV-1 infection in a subject, the method comprising:

providing a plurality of HIV-1 envelope proteins or immunogenic fragments thereof comprising tyrosine residues at gp120 positions 173 or 177, or at both positions 173 and 177;

sulfating the tyrosine residues at gp120 positions 173 or 177, or at both positions 173 and 177 on at least 90% of the HIV-1 envelope proteins or immunogenic fragments in the plurality, wherein sulfating the tyrosine residues comprises (A) or (B):

(A) expressing a first heterologous nucleic acid molecule encoding the HIV-1 envelope protein or immunogenic fragment thereof and a second heterologous nucleic acid molecule encoding a tyrosine sulfotransferase or a variant thereof with tyrosine sulfation activity in a cell; or (B) incubating the plurality of HIV-1 envelope proteins or immunogenic fragments thereof with a purified tyrosine sulfotransferase or a variant thereof with tyrosine sulfation activity under conditions sufficient for tyrosine sulfation of gp120 positions 173 or 177, or both positions 173 and 177; and purifying the plurality of HIV-1 envelope proteins or immunogenic fragments, thereby making the sulfated HIV-1 envelope protein or immunogenic fragment thereof for use in stimulating an immune response against HIV-1 infection in a subject.

2. The method of claim 1, wherein sulfating the tyrosine residues comprises (A).

3. The method of claim 1, wherein sulfating the tyrosine residues comprises (B).

4. A method of making a sulfated HIV-1 envelope protein or immunogenic fragment thereof for use in stimulating an immune response against HIV-1 infection in a subject, the method comprising co-expressing in a cell in vitro:

a first heterologous nucleic acid molecule encoding a HIV-1 envelope protein or immunogenic fragment thereof in a mammalian cell line, wherein the HIV-1 envelope protein or immunogenic fragment thereof comprises tyrosine residues at gp120 positions 173 or 177, or at both positions 173 and 177; and a second heterologous nucleic acid molecule encoding a tyrosine sulfotransferase or a variant thereof with tyrosine sulfation activity;

under conditions sufficient for sulfation of the tyrosine residues at gp120 positions 173 or 177, or at both positions 173 and 177 by the tyrosine sulfotransferase or the variant, thereby making the sulfated HIV-1 envelope protein or immunogenic fragment thereof for use in stimulating an immune response against HIV-1 infection in a subject.

5. A method of making a sulfated HIV-1 envelope protein or immunogenic fragment thereof for use in stimulating an immune response against HIV-1 infection in a subject, the method comprising:

incubating a HIV-1 envelope protein or immunogenic fragment thereof comprising tyrosine residues at gp120 positions 173 or 177, or at both positions 173 and 177 with a purified tyrosine sulfotransferase or a variant thereof with tyrosine sulfation activity under conditions sufficient for sulfation of the tyrosine residues by the tyrosine sulfotransferase or the variant, thereby making the sulfated HIV-1 envelope protein or immunogenic fragment thereof for use in stimulating an immune response against HIV-1 infection in a subject.

6. The method of claim 1, wherein the HIV-1 envelope protein or immunogenic fragment comprises gp160, gp140, or gp120.

7. The method of claim 1, wherein the tyrosine sulfotransferase is TPST1 or TPST2 or a variant thereof with tyrosine sulfation activity.

8. The method of claim 1, wherein the cell is an immortalized T or B cell.

9. The method of claim 4, wherein the HIV-1 envelope protein or immunogenic fragment comprises gp160, gp140, or gp120.

10. The method of claim 5, wherein the HIV-1 envelope protein or immunogenic fragment comprises gp160, gp140, or gp120.

11. The method of claim 4, wherein the tyrosine sulfotransferase is TPST1 or TPST2 or a variant thereof with tyrosine sulfation activity.

12. The method of claim 5, wherein the tyrosine sulfotransferase is TPST1 or TPST2 or a variant thereof with tyrosine sulfation activity.

13. The method of claim 5, wherein the cell is an immortalized T or B cell.

* * * * *